(12) United States Patent
Davidson et al.

(10) Patent No.: US 12,424,023 B2
(45) Date of Patent: Sep. 23, 2025

(54) SYSTEM AND METHOD FOR AUTHENTICATION AND SYSTEM AND METHOD FOR AUTHENTICATION BASED PERSONAL SERVICE

(71) Applicant: Echo ID Ltd, Tel Aviv-Jaffa (IL)

(72) Inventors: Perry Davidson, Tel Aviv (IL); Ianiv Yosef Eisenscher, Tel Aviv (IL); Nimrod Reshef, Lehavim (IL); Binyamin Schwartz, Sede Eliezer (IL); Oren Harel, Ashdod (IL); Harel Gur, Tel-Aviv (IL); Or Averbuch, Petah Tikva (IL); Yakov Yury Rovniagin, Ness Ziona (IL)

(73) Assignee: Echo ID Ltd, Tel Aviv-Jaffa (IL)

( * ) Notice: Subject to any disclaimer, the term of this patent is extended or adjusted under 35 U.S.C. 154(b) by 742 days.

(21) Appl. No.: 17/437,790

(22) PCT Filed: Mar. 12, 2020

(86) PCT No.: PCT/IL2020/050301
§ 371 (c)(1),
(2) Date: Sep. 9, 2021

(87) PCT Pub. No.: WO2020/183476
PCT Pub. Date: Sep. 17, 2020

(65) Prior Publication Data
US 2022/0151300 A1    May 19, 2022

Related U.S. Application Data

(60) Provisional application No. 62/817,133, filed on Mar. 12, 2019, provisional application No. 62/871,254,
(Continued)

(51) Int. Cl.
*G06V 40/00* (2022.01)
*A24F 40/42* (2020.01)
(Continued)

(52) U.S. Cl.
CPC ............ *G06V 40/172* (2022.01); *A24F 40/42* (2020.01); *A24F 40/485* (2020.01); *A24F 40/51* (2020.01);
(Continued)

(58) Field of Classification Search
CPC ..... G06V 40/172; A24F 40/42; A24F 40/485; A24F 40/51; A24F 40/53; A24F 40/57;
(Continued)

(56) References Cited

U.S. PATENT DOCUMENTS

| 5,910,946 A | 6/1999 | Csapo |
| 8,021,356 B2 | 9/2011 | Uchiyama et al. |

(Continued)

FOREIGN PATENT DOCUMENTS

| CA | 2636115 | 7/2007 |
| CA | 2749077 | 2/2013 |

(Continued)

OTHER PUBLICATIONS

International Preliminary Report on Patentability Dated Sep. 23, 2021 From the International Bureau of WIPO Re. Application No. PCT/IL2020/050292. (8 Pages).

(Continued)

*Primary Examiner* — Jonathan S Lee

(57) ABSTRACT

A system and method are for authentication and a system and method are for authentication based personal service.

26 Claims, 23 Drawing Sheets

Related U.S. Application Data filed on Jul. 8, 2019, provisional application No. 62/958,444, filed on Jan. 8, 2020, provisional application No. 62/958,450, filed on Jan. 8, 2020, provisional application No. 62/958,454, filed on Jan. 8, 2020.

(51) Int. Cl.
| | |
|---|---|
| *A24F 40/485* | (2020.01) |
| *A24F 40/51* | (2020.01) |
| *A24F 40/53* | (2020.01) |
| *A24F 40/57* | (2020.01) |
| *A24F 40/65* | (2020.01) |
| *A61M 15/00* | (2006.01) |
| *G06T 7/70* | (2017.01) |
| *G06V 40/16* | (2022.01) |
| *G09B 21/00* | (2006.01) |
| *H04K 3/00* | (2006.01) |
| *G01K 13/20* | (2021.01) |
| *G01P 13/00* | (2006.01) |

(52) U.S. Cl.
CPC .............. *A24F 40/53* (2020.01); *A24F 40/57* (2020.01); *A24F 40/65* (2020.01); *A61M 15/0001* (2014.02); *A61M 15/002* (2014.02); *G06T 7/70* (2017.01); *G09B 21/00* (2013.01); *H04K 3/00* (2013.01); *A61M 2205/13* (2013.01); *A61M 2205/3327* (2013.01); *A61M 2205/3375* (2013.01); *A61M 2205/3569* (2013.01); *A61M 2205/36* (2013.01); *A61M 2205/609* (2013.01); *G01K 13/20* (2021.01); *G01P 13/00* (2013.01); *G06T 2207/30201* (2013.01)

(58) Field of Classification Search
CPC . A24F 40/65; A61M 15/0001; A61M 15/002; A61M 2205/13; A61M 2205/3327; A61M 2205/3375; A61M 2205/3569; A61M 2205/36; A61M 2205/609; G06T 7/70; G06T 2207/30201; G09B 21/00; H04K 3/00; G01K 13/20; G01P 13/00
USPC .................................................... 128/203.27
See application file for complete search history.

(56) References Cited

U.S. PATENT DOCUMENTS

| | | | |
|---|---|---|---|
| 9,763,478 | B2 | 9/2017 | Cameron et al. |
| 9,945,818 | B2 | 4/2018 | Ganti et al. |
| 9,999,250 | B2 | 6/2018 | Minskoff et al. |
| 10,467,460 | B2* | 11/2019 | Nienhouse ............... G06N 7/01 |
| 11,400,242 | B2 | 8/2022 | Ziegler et al. |
| 12,217,748 | B2 | 2/2025 | Hartung et al. |
| 2005/0148847 | A1 | 7/2005 | Uchiyama et al. |
| 2007/0102109 | A1 | 5/2007 | Katritzky et al. |
| 2010/0271218 | A1 | 10/2010 | Hoag et al. |
| 2011/0060448 | A1 | 3/2011 | Gotou et al. |
| 2011/0170837 | A1 | 7/2011 | Barnes, Jr. |
| 2012/0101840 | A1 | 4/2012 | Choi |
| 2015/0055444 | A1 | 2/2015 | Bacom et al. |
| 2015/0141079 | A1 | 5/2015 | Wang et al. |
| 2015/0181945 | A1 | 7/2015 | Tremblay |
| 2015/0257445 | A1 | 9/2015 | Henry, Jr. et al. |
| 2016/0104041 | A1 | 4/2016 | Bowers |
| 2016/0158782 | A1 | 6/2016 | Henry, Jr. et al. |
| 2016/0302488 | A1 | 10/2016 | Fernando et al. |
| 2017/0101006 | A1 | 4/2017 | DeVries et al. |
| 2017/0231273 | A1 | 8/2017 | Xiang |
| 2017/0333645 | A1 | 11/2017 | Alizoti et al. |
| 2018/0043114 | A1 | 2/2018 | Bowen et al. |
| 2018/0101721 | A1 | 4/2018 | Nienhouse |
| 2018/0110941 | A1 | 4/2018 | Smith et al. |
| 2018/0161531 | A1 | 6/2018 | Costella et al. |
| 2018/0263283 | A1 | 9/2018 | Popplewell et al. |
| 2018/0279918 | A1 | 10/2018 | Hagen et al. |
| 2018/0286208 | A1 | 10/2018 | Baker et al. |
| 2018/0353052 | A1 | 12/2018 | Hanina et al. |
| 2019/0160269 | A1* | 5/2019 | Skoda ................... A61M 31/00 |
| 2019/0387797 | A1* | 12/2019 | Christensen .......... A61M 15/06 |
| 2020/0038295 | A1 | 2/2020 | Rouse et al. |
| 2020/0061314 | A1* | 2/2020 | Hatamian ......... A61M 15/0083 |
| 2021/0011446 | A1 | 1/2021 | Anderson et al. |
| 2021/0401674 | A1 | 12/2021 | Guo et al. |
| 2022/0053836 | A1* | 2/2022 | Cazzoli ................... A24F 40/53 |
| 2022/0157079 | A1 | 5/2022 | Davidson |
| 2022/0160047 | A1 | 5/2022 | Davidson |
| 2023/0120935 | A1* | 4/2023 | Davidson ............... G06V 40/00 |
| 2023/0321353 | A1 | 10/2023 | Endo et al. |

FOREIGN PATENT DOCUMENTS

| | | |
|---|---|---|
| CA | 3025407 | 11/2017 |
| CN | 103585021 | 2/2014 |
| CN | 105792687 | 7/2016 |
| CN | 107744472 | 3/2018 |
| CN | 109288138 | 2/2019 |
| EP | 2360610 | 8/2011 |
| EP | 2360610 A2 | 8/2011 |
| EP | 3342442 | 7/2018 |
| EP | 3342442 A1 | 7/2018 |
| JP | H11-203479 | 7/1999 |
| JP | 2007-097787 | 4/2007 |
| JP | 2008-170395 | 7/2008 |
| JP | 2010-185813 | 8/2010 |
| JP | 2013-145500 | 7/2013 |
| JP | 2017-519257 | 7/2017 |
| JP | 2018-536513 | 12/2018 |
| TW | 201143825 | 12/2011 |
| WO | 2016/009202 A1 | 1/2016 |
| WO | WO 2016/009202 | 1/2016 |
| WO | WO 2019/126805 | 6/2019 |
| WO | WO 2020/183470 | 9/2020 |
| WO | WO 2020/183476 | 9/2020 |
| WO | WO 2020/183478 | 9/2020 |

OTHER PUBLICATIONS

International Preliminary Report on Patentability Dated Sep. 23, 2021 From the International Bureau of WIPO Re. Application No. PCT/IL2020/050301. (9 Pages).

International Preliminary Report on Patentability Dated Sep. 23, 2021 From the International Bureau of WIPO Re. Application No. PCT/IL2020/050304. (7 Pages).

International Search Report and the Written Opinion Dated Jul. 7, 2020 From the International Searching Authority Re. Application No. PCT/IL2020/050304. (12 Pages).

International Search Report and the Written Opinion Dated Jul. 14, 2020 From the International Searching Authority Re. Application No. PCT/IL2020/050301. (11 Pages).

International Search Report and the Written Opinion Dated May 19, 2020 From the International Searching Authority Re. Application No. PCT/IL2020/050292. (10 Pages).

Supplementary European Search Report and the European Search Opinion Dated May 26, 2023 From the European Patent Office Re. Application No. 20769742.6. (11 Pages).

Supplementary European Search Report and the European Search Opinion Dated May 25, 2023 From the European Patent Office Re. Application No. 20770417.2. (11 Pages).

Translation Dated Feb. 19, 2024 Decision of Rejection Dated Jan. 30, 2024 From the Intellectual Property Office, Ministry of Economic Affairs of the Republic of Taiwan, R.O.C. Re. Application No. 109108270. (8 Pages).

English Summary Dated May 3, 2023 of Request for Examination and Search Report Dated Apr. 20, 2023 From the Federal Government Institution, Federal Institute of Industrial Property of the

(56) References Cited

OTHER PUBLICATIONS

Federal Service of Intellectual Property, Patents and Trademarks of the Russian Federation, FIPS Re. Application No. 2021129551. (8 Pages).
Request for Examination and Search Report Dated Apr. 20, 2023 From the Federal Government Institution, Federal Institute of Industrial Property of the Federal Service of Intellectual Property, Patents and Trademarks of the Russian Federation, FIPS Re. Application No. 2021129551 (26 Pages).
International Search Report and Written Opinion for PCT/IL2020/050292 (May 19, 2020).
International Search Report and Written Opinion for PCT/IL2020/050301 (Jul. 14, 2020).
International Search Report and Written Opinion for PCT/IL2020/050304 (Jul. 7, 2020).
Translation Dated Aug. 4, 2023 of Decision of Examination Dated Jul. 7, 2023 From the Intellectual Property Office, Ministry of Economic Affairs of the Republic of Taiwan, R.O.C. Re. Application No. 109108270 . (8 Pages).
Notice of Reason(s) for Rejection Dated Jan. 9, 2024 From the Japan Patent Office Re. Application No. 2021-555086 and Its Translation Into English. (8 Pages).
Requisition by the Examiner Dated Feb. 28, 2024 From the Innovation, Science and Economic Development Canada, Canadian Intellectual Property Office Re. Application No. 3,132,948. (13 Pages).
Requisition by the Examiner Dated Sep. 27, 2023 From the Innovation, Science and Economic Development Canada, Canadian Intellectual Property Office Re. Application No. 3,132,930. (4 Pages).
Decision of Rejection Dated Jan. 30, 2024 From the Intellectual Property Office, Ministry of Economic Affairs of the Republic of Taiwan, R.O.C. Re. Application No. 109108270. (14 Pages).
Supplementary European Search Report and the European Search Opinion Dated Mar. 7, 2024 From the European Patent Office Re. Application No. 20771111.0. (9 Pages).
Lu et al. "Lip Reading-Based User Authentication Through Acoustic Sensing . on Smartphones", IEEE/ACM Transactions on Networking, XP011709607, 27(1 ):447-460, Published Jan. 23, 2019.
Decision of Examination Dated Jul. 7, 2023 From the Intellectual Property Office, Ministry of Economic Affairs of the Republic of Taiwan, R.O.C. Re. Application No. 109108270 and Its Summary Into English (18 Pages).
Request for Examination and Search Report Dated Jun. 13, 2024 From the (Rospatent), Federal Government Institution of Industrial Property of the Federal Service of Intellectual Property, Patents and Trademark of the Russian Federation Re. Application No. 2021129551. (13 Pages).
Translation Dated Jun. 18, 2024 of Request for Examination and Search Report Dated Jun. 13, 2024 From the (Rospatent), Federal Government Institution of Industrial Property of the Federal Service of Intellectual Property, Patents and Trademark of the Russian Federation Re. Application No. 2021129551. (11 Pages).
Examination Report Dated Oct. 8, 2024 From the Australian Government, IP Australia Re. Application No. 2020234110. (3 Pages).
Translation Dated Aug. 1, 2024 of Notification of Office Action and Search Report Dated Jul. 3, 2024 From the State Intellectual Property Office of the People's Republic of China Re. Application No. 202080035255.5. (12 Pages).
Translation Dated Aug. 2, 2024 of Notification of Office Action and Search Report Dated Jul. 3, 2024 From the State Intellectual Property Office of the People's Republic of China Re. Application No. 202080035282.2. (12 Pages).
Requisition by the Examiner Dated Aug. 15, 2024 From the Innovation, Science and Economic Development Canada, Canadian Intellectual Property Office Re. Application No. 3,132,930. (4 Pages).
Notice of Reason(s) for Rejection Dated Jun. 18, 2024 From the Japan Patent Office Re. Application No. 2021-555086 and Its Translation Into English. (6 Pages).
Official Action Dated Jun. 20, 2024 From the US Patent and Trademark Office Re. U.S. Appl. No. 17/437,789. (65 Pages).
Notification of Office Action and Search Report Dated Jul. 3, 2024 From the State Intellectual Property Office of the People's Republic of China Re. Application No. 202080035255.5. (9 Pages).
Notification of Office Action and Search Report Dated Jul. 3, 2024 From the State Intellectual Property Office of the People's Republic of China Re. Application No. 202080035282.2. (9 Pages).
Examination Report Dated Sep. 20, 2024 From the Australian Government, IP Australia Re. Application No. 2020234112. (3 Pages).
Decision of Examination Dated Dec. 11, 2024 From the Intellectual Property Office, Ministry of Economic Affairs of the Republic of Taiwan, R.O.C. Re. Application No. 109108270 and Its Translation Into English. (7 Pages).
Notification of Office Action and Search Report Dated Mar. 6, 2025 From the State Intellectual Property Office of the People's Republic of China Re. Application No. 202080035282.2 and Its Translation Into English. (15 Pages).
Notification of Office Action and Search Report Dated Mar. 19, 2025 From the State Intellectual Property Office of the People's Republic of China Re. Application No. 202080035255.5 and Its Translation in English. (12 Pages).
Official Action Dated Jan. 3, 2025 From the US Patent and Trademark Office Re. U.S. Appl. No. 17/437,795. (59 Pages).
Official Action Dated Jan. 28, 2025 From the US Patent and Trademark Office Re. U.S. Appl. No. 17/437,789. (45 Pages).
Office Action Dated Apr. 21, 2025 From the Israel Patent Office Re. Application No. 286278. (6 Pages).
Communication Pursuant to Article 94(3) EPC Dated Jul. 18, 2025 From the European Patent Office Re. Application No. 20770417.2 (9 Pages).
Official Action Dated May 19, 2025 From the US Patent and Trademark Office Re. U.S. Appl. No. 17/437,795. (16 Pages).

* cited by examiner

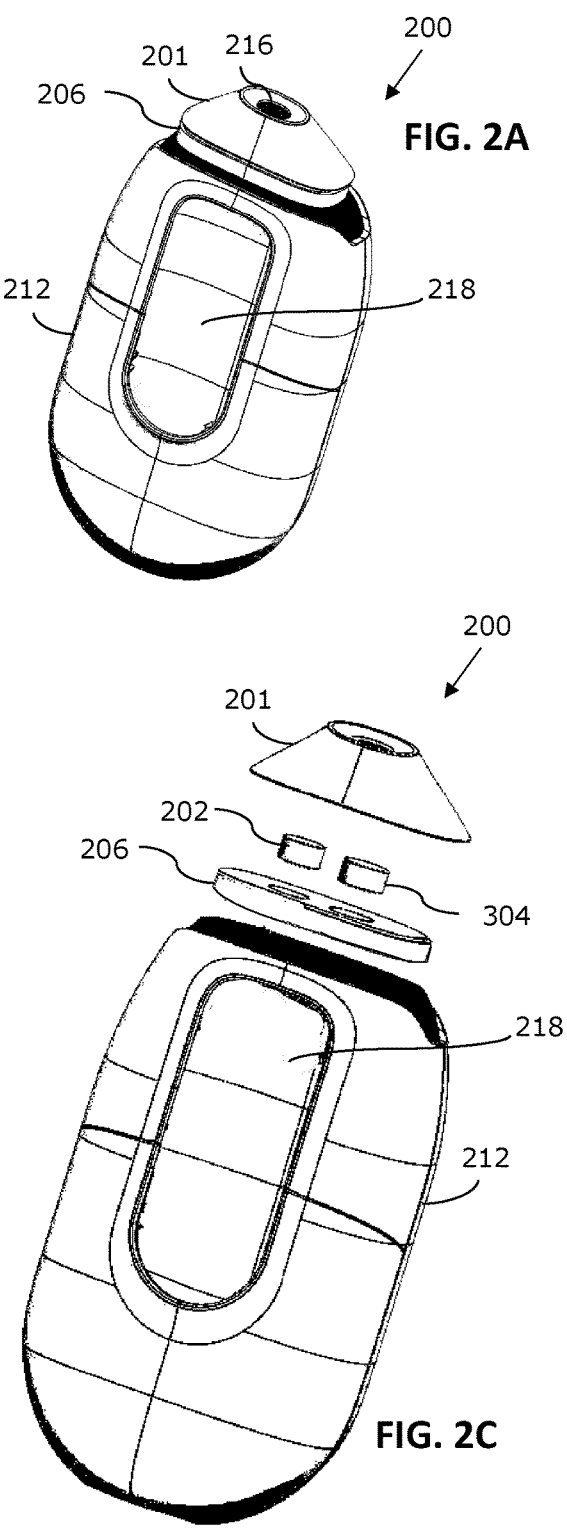

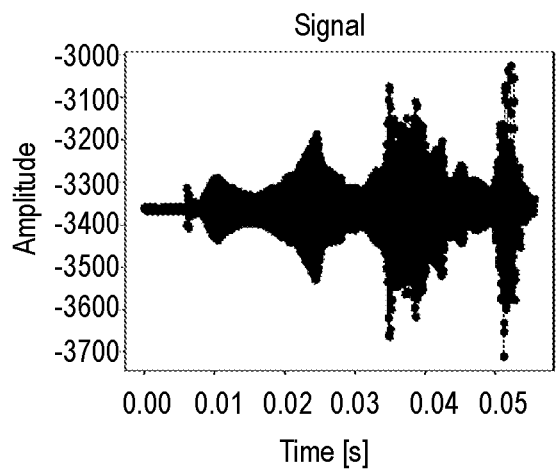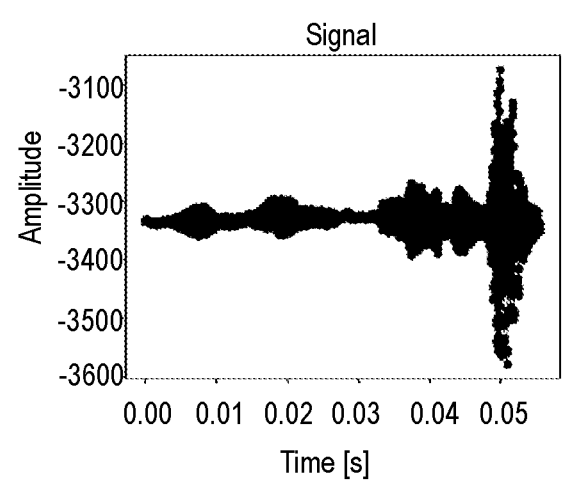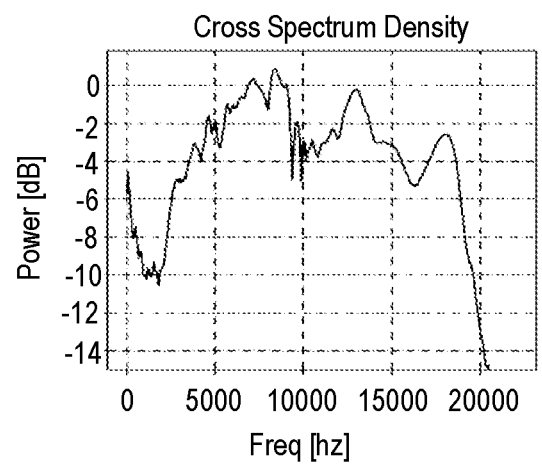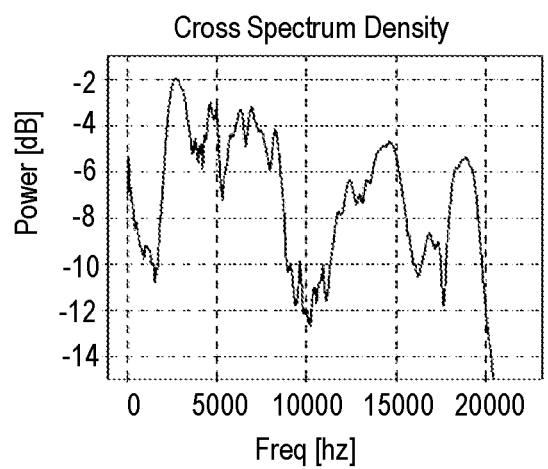
FIG. 3C  FIG. 3D

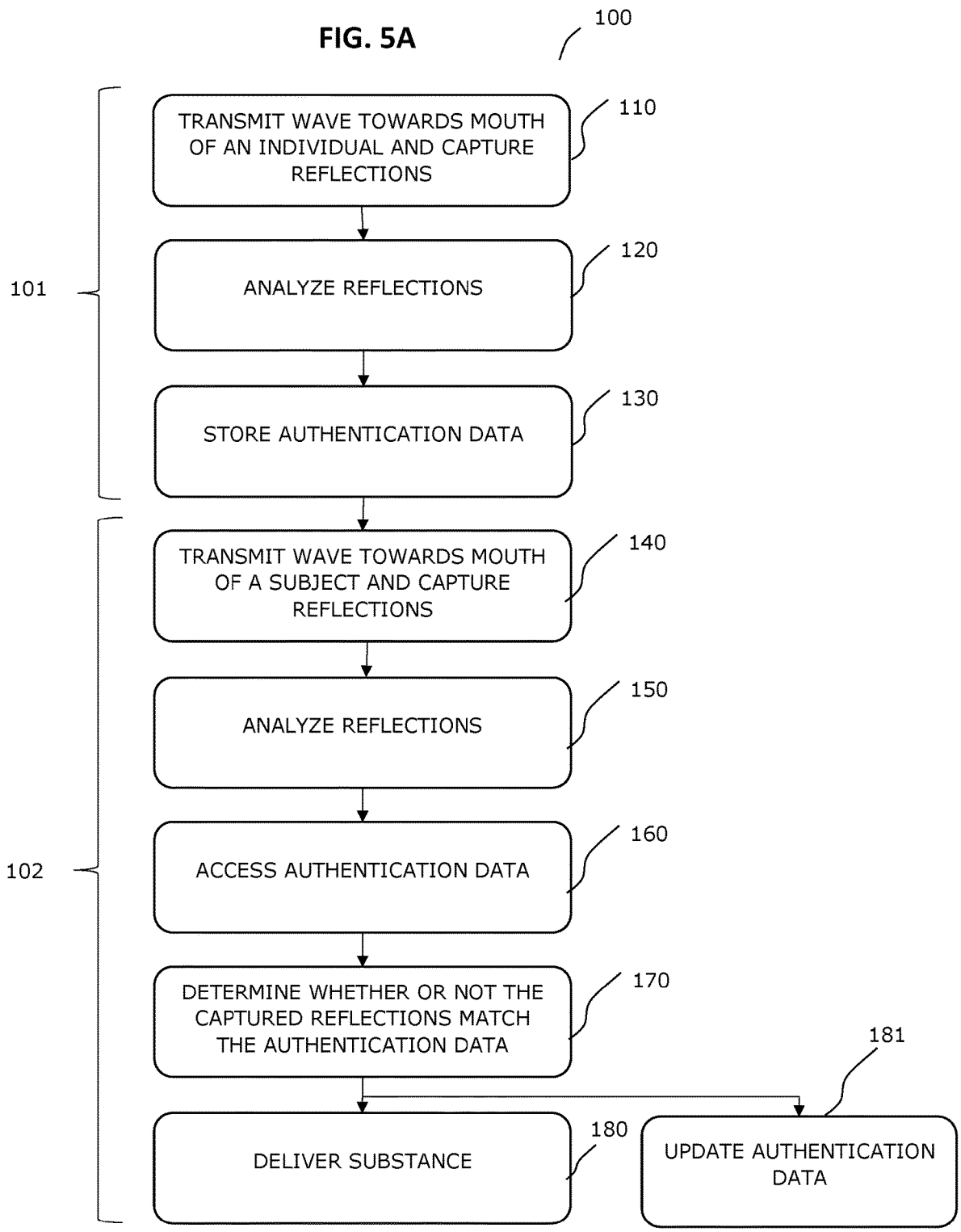

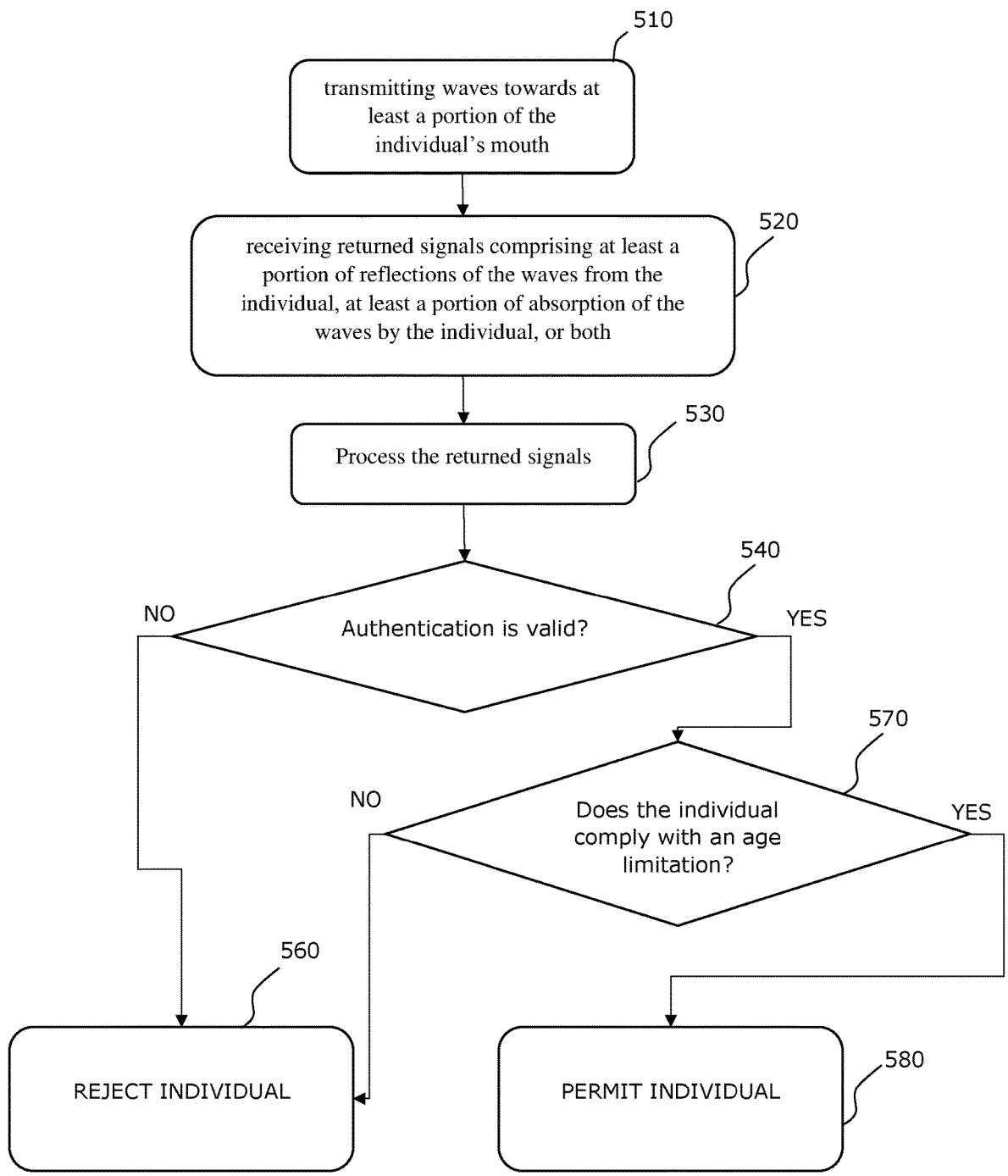

MFCC

Time

SYSTEM AND METHOD FOR AUTHENTICATION AND SYSTEM AND METHOD FOR AUTHENTICATION BASED PERSONAL SERVICE

This application is a National Stage of PCT/IL2020/050301, filed Mar. 12, 2020, which claims benefit of U.S. Provisional Application No. 62/817,133, filed Mar. 12, 2019, U.S. Provisional Application No. 62/871,254, filed Jul. 8, 2019, U.S. Provisional Application No. 62/958,444, filed Jan. 8, 2020, U.S. Provisional Application No. 62/958,450, filed Jan. 8, 2020 and U.S. Provisional Application No. 62/958,454, filed Jan. 8, 2020, which applications are incorporated herein by reference. To the extent appropriate, a claim of priority is made to each of the above-disclosed applications.

FIELD OF THE INVENTION

The invention relates to identification, authorization, registration and/or operation of a fluid delivery system for delivering substances to individuals.

BACKGROUND

Currently sale of fluid delivery devices (e.g., vaping devices or e-cigarettes) can be controlled to individuals based on the individual presenting acceptable identification to obtain the device. For example, a fluid delivery device of an e-cigarette that delivers nicotine (for example) can be sold to an individual in a store upon the individual showing a photo identification to prove that the individual is above a certain age.

Once an individual has a fluid delivery device in their possession, the individual can provide that fluid delivery device to any other individual or another individual can use the fluid delivery device without the permissions of the individual the device was sold/prescribed to. This can cause unauthorized individuals (e.g., children) to gain access to controlled substances.

Identification generally refers to a process of presenting one's identity to a system. It is typically part of an initial stage of accessing a system. An identification process usually involves presenting one's own personal identification data (e.g., providing a username during a login process or using ATM cards).

Authentication relates to validating an identity provided to a system and is often used to distinguish between authorized and unauthorized individuals or between individuals having different authorizations. Authentication may take place after identification is complete, or concurrently to the identification process. At times, authentication is performed without identification of a unique individual, for example by authenticating that an individual belongs to a defined group of individuals (e.g., one of a group of employees having the same user ID). This may also be considered identification, in the sense that the group is identified.

Among the known means of identification is the use of biometric identifiers, namely distinctive characteristics that can identify individuals or groups of individuals. Typical examples of biometric identifiers used to authenticate individual identities include fingerprints, face recognition, iris/retina recognition, and voice patterns. These biometric identifiers are vulnerable to duplication without the knowledge of the individual from whom the biometrics are remotely retrieved, for example by photography (for visible features) and recording (for voice).

SUMMARY OF THE INVENTION

Some embodiments may provide a method for biometric identifying property of an individual, the method may include: transmitting waves towards at least a portion of a mouth of an individual; sensing, by a device, at least a portion of reflections of the waves from the individual; deriving an oral signature based on the sensing; and storing an indication of the oral signature in a database.

In some embodiments, storing the oral signature includes storing the oral signature in association with at least one of a personal device, a characteristic associated with the individual, a personal property of the individual, data identifying the individual, an indication of restriction, an indication of permission, an indication of an action, or any combination thereof.

In some embodiments, the personal property includes an indication of age or date of birth of the individual.

In some embodiments, the data identifying the individual includes a name, a social security number, an identification number, a passport number, a license number, a facial image, or any combination thereof.

Some embodiments may provide a method for authenticating an individual, the method may include: receiving, using a sensor, reflected waves from the individual's mouth; and authenticating the individual based on the at least a portion of the reflected waves received by the sensor.

Some embodiments may provide a method for authenticating an individual, the method may include: transmitting waves towards at least a portion of the individual's mouth via at least one of the individual's mouth and nose; receiving, using a sensor, reflected waves comprising at least a portion of reflections of the waves from the individual; and authenticating the individual based on the at least a portion of the reflected waves received by the sensor.

In some embodiments, the transmitting waves includes generating the waves by at least one of: a wave generator device and airflow sound generated by at least one of inhalation and exhalation by the individual.

In some embodiments, the method may include delivering a substance to the individual upon successful authentication.

In some embodiments, the method may include performing authenticating and delivering within a single inhalation by the individual.

In some embodiments, the method may include transmitting the waves towards the individual further comprises transmitting towards at least a portion of a mouth of the individual.

In some embodiments, the mouth includes lips, tissue surrounding the lips, the oral cavity or any combination thereof.

In some embodiments, the authenticating comprises determining whether an age of the individual is at least one of above or below one or more age thresholds.

In some embodiments, the authenticating comprises determining whether an age of the individual is at least one of above a first age threshold and below a second age threshold, the second age threshold being lower than the first age threshold.

In some embodiments, the waves include sound waves.

In some embodiments, the sound waves are selected from the group consisting of sound waves that: have a frequency between 15 kilohertz to 20 kilohertz; have a frequency in the range of 2 hertz to 20 kilohertz; and have a frequency less than 17 kilohertz.

In some embodiments, the method may include transmitting the waves with a volume such that the individual can hear the sound waves and a second individual cannot hear the sound waves, the head of the second individual being at a distance of at least 30 centimeters from the head of the individual who can hear the sound waves.

In some embodiments, the distance between the head of the individual and the head of the second individual is at least 50 centimeters.

In some embodiments, the method may include transmitting the waves as a single pulse wave, a plurality of wave pulses, or any combination thereof.

In some embodiments, the method may include detecting, after a successful authentication of the individual, whether the sensor has moved beyond a predefined minimal range.

In some embodiments, the sensor is coupled to a fluid delivery device adapted to deliver a substance to the individual during inhalation by the individual, and wherein the predefined minimal range is based on an amount of movement that is typical during inhalation.

In some embodiments, the predefined minimal range is based on an amount of movement that is typical during inhalation for the individual.

In some embodiments, the method may include causing at least one of fluid delivery and substance delivery to be prevented or stopped upon detecting that the predefined minimal range was exceeded.

In some embodiments, the method may include at least one of: preventing substance delivery until the authentication is valid; permitting substance delivery only after the authentication is valid;

stopping substance delivery once the authentication is reset; and locking the device once authentication is invalid.

In some embodiments, the method may include at least one of: preventing a heating element used to heat the substance for delivery from heating above a predefined threshold until the authentication is performed; permitting the heating element to heat above a predefined threshold only after the authentication is successful; and reducing or stopping the heating element's heat emission once the authentication indication is reset.

In some embodiments, the method may include at least one of: preventing fluid from being delivered to the individual until the authentication is performed; controlling a flow path of the fluid to the individual such that the fluid reaching the individual will carry the substance only once the authentication indication is successful.

In some embodiments, the method may include determining if the individual is a child based on the reflected waves received by the sensor.

In some embodiments, the method may include determining if the individual is an adult based on the reflected waves received by the sensor.

In some embodiments, the authentication is based on biometric data entered to the system.

In some embodiments, the biometric data includes at least one of gender, ethnicity, geographical origin, or any combination thereof.

In some embodiments, the method may include comparing the reflected waves with a signature of at least one registered individual to determine whether the individual is a registered individual.

In some embodiments, the method may include identifying the individual based on the reflected waves.

In some embodiments, the method may include: transmitting the waves periodically for a predefined period of time or for a predefined number of transmissions, and analyzing at least some reflected waves over the predefined period of time or after the predefined number of transmissions to authenticate the individual.

In some embodiments, the method may include authenticating the individual at a predetermined time interval.

In some embodiments, the method may include administering the substance to the individual only if the individual is identified as an authenticated individual.

In some embodiments, the substance includes a substance selected from a group of substances consisting of substances derived from cannabis, substances derived from tobacco, cannabinoids, nicotine, pharmaceuticals, and controlled substances.

In some embodiments, the method may include regulating fluid flow during inhalation, and controlling the flow based on the authentication.

In some embodiments, the method may include delivering a substance to the individual, wherein the flow of the substance is controlled based on authentication.

In some embodiments, the method may include preventing the delivery of a substance to the individual if the authentication indicates that the individual is a child.

In some embodiments, the method may include preventing the release of a substance to the individual if the authentication does not indicate that the individual is an adult.

In some embodiments, the method may include controlling a pressure dependent flow valve such that flow through the valve occurs during inhalation only when a generated pressure exceeds a threshold and wherein transmitting of waves performed partially or only as long as the valve is closed.

In some embodiments, the method may include detecting inhalation of the individual.

In some embodiments, the method may include authenticating each time an inhalation is performed by the individual.

In some embodiments, the method may include delivering a substance to the individual and authenticating at least once before delivering of a substance to the individual and at least once during delivering of the substance to the individual.

In some embodiments, the method may include preventing a substance from being delivered to the individual if the individual is not successfully authenticated in the authentication step.

In some embodiments, the method may include outputting an alarm based on authentication, wherein the alarm is an audio alarm or a visual alarm.

In some embodiments, the method may include issuing a notification based on the authentication, wherein the notification is output by the fluid delivery device, by a remote device, or both.

In some embodiments, the method may include operating in accordance with an operation scheme associated with the individual.

In some embodiments, the method may include authenticating a predetermined number of times before activating the device and/or during device operation.

In some embodiments, the method may include storing usage information, authentication information, registration information, or any combination thereof on a memory.

In some embodiments, the method may include registering the individual.

In some embodiments, the registering comprises: extracting from the detected waves at least one signature, associating the at least one signature with the individual, and registering the individual with the at least one signature.

In some embodiments, the method may include requiring a security token for registering.

In some embodiments, the method may include performing the registration process only once per individual and/or per substance regime.

In some embodiments, the method may include transmitting the waves by a speaker.

In some embodiments, the method may include authenticating upon receiving an indication that the individual is inhaling via the opening.

In some embodiments, a duration between the individual inhaling and analysis of whether the individual is authentic or not is 10-100 ms.

In some embodiments, the method may include: releasing the substance upon the indication that the individual is inhaling and simultaneously authenticating the individual, and stopping the releasing if the authentication is unsuccessful.

In some embodiments, the method may include using machine learning to determine authentication.

In some embodiments, the method may include normalizing one or more of the detected waves with respect to a predetermined reference wave signal of the sound of the environment.

In some embodiments, the method may include determining and cancelling environmental noise.

In some embodiments, the method may include filtering the detected waves that are below a predefined threshold.

In some embodiments, the method may include setting the predefined threshold below −6, −7, or −8 Decibels.

In some embodiments, the method may include: positioning a fluid delivery device in the individual's mouth; and transmitting the waves by the fluid delivery device.

In some embodiments, the method may include detecting that the fluid delivery device is positioned according to a groove in a structure of the fluid delivery device.

In some embodiments, authenticating includes at least one of determining an identify of the individual and determining that the individual is an adult. In some embodiments, the method may include determining whether the individual is positioned according to a predetermined initial position and alerting the individual to return to the predetermined initial position if the individual is not within the predetermined initial position.

In some embodiments, the method may include authenticating the individual via a second authentication method.

In some embodiments, the second authentication method is requested if authenticating the individual returns inconclusive results.

In some embodiments, the second authentication method includes inputting data into a user interface.

In some embodiments, the method may include upon successful authentication, restricting delivery of the substance to the individual based on a permitted total amount of the substance for a defined period.

Some embodiments may provide an authentication device for authenticating an individual, the authentication device may include: a wave generator for transmitting waves towards a mouth of the individual; a sensor to detect at least a portion of reflections of the waves from the individual; a memory for storing at least one oral signature; and a processor coupled to the sensor and configured to: authenticate the individual by analyzing the at least portion of reflections of the waves from the individual; derive an oral signature of the individual; and compare the derived oral signature to at least one oral signature stored in the memory.

In some embodiments, the authentication device may include a mouthpiece structured for insertion into the mouth of the individual such that waves generated by the wave generator are transmitted from the mouthpiece directly into at least one of the lips and oral cavity of the individual.

In some embodiments, the authentication device may include a sensor for detecting at least one substance exhaled by the individual.

In some embodiments, the at least one substance includes ethanol, and the device is configured to issue an indication of a blood alcohol level of the individual.

In some embodiments, the authentication device is associated with a controller configured to enable use of a second device based at least partially on the authentication of the individual in combination with the indication of a blood alcohol level of the individual.

In some embodiments, the second device is a motor vehicle and the controller is configured to enable use of the motor vehicle by enabling the ignition of the motor vehicle.

In some embodiments, the authentication device may include an oral thermometer.

Some embodiments may provide a device for obtaining an oral signature of an individual, may include: a housing comprising a wave generator and a wave sensor; and at least one conduit coupled to the housing configured to allow a user to inhale or exhale via the conduit; wherein the at least one conduit, the wave sensor and the wave generator are positioned and configured to allow waves generated by the wave generator to be transmitted towards at least a portion of a mouth of an individual and reflections of the waves to be sensed by the sensor during inhalation or exhalation by the individual via the conduit.

Some embodiments may provide a fluid delivery device for delivery of a substance to an individual, the fluid delivery device may include: a reservoir region configured to house a reservoir of the substance within the fluid delivery device; a wave generator configured to transmit waves; a sensor configured to detect at least a portion of reflections of the waves transmitted by the wave generator; and a processor coupled to the sensor and configured to authenticate the individual based on the at least portion of reflections of the waves from the individual.

In some embodiments, the fluid delivery device may include an actuator associated with the reservoir, the actuator being configured to control at least one of: release of the substance from the reservoir, delivery of the substance to the individual, based on the authentication of the individual by the processor.

In some embodiments, the fluid delivery device may include a mouthpiece configured to direct waves transmitted by the wave generator towards at least a portion of a mouth of the individual.

In some embodiments, the mouthpiece is configured to direct the waves into at least one of the individual's lips, tissue surrounding the lips, the oral cavity, nose cavity, nasal tissue, or any combination thereof.

In some embodiments, the mouthpiece is configured to allow delivery of the fluid to the individual.

In some embodiments, the processor is configured to authenticate the individual by determining at least whether an age of the individual is above or below an age threshold, based on analysis of the at least portion of reflection of the waves.

In some embodiments, the waves include sound waves.

In some embodiments, the sound waves have a frequency between 15 kilohertz to 20 kilohertz.

In some embodiments, the sound waves have a frequency in the range of 20 hertz to 20 kilohertz.

In some embodiments, the sound waves have a frequency in the range of 20 hertz to 15 kilohertz.

In some embodiments, the sound waves have a frequency less than 17 kilohertz.

In some embodiments, the wave generator is configured to transmit the sound waves with such volume that the individual can hear the sound waves and a second individual cannot hear the sound waves.

In some embodiments, the wave generator is configured to output a single pulse wave or a plurality of pulses wave.

In some embodiments, the fluid delivery device may include a motion detection sensor configured to detect movement of the fluid delivery device and wherein the processor is configured to: determine, after a successful authentication, whether the fluid delivery device has moved beyond a predefined minimal range.

In some embodiments, the predefined minimal range is based on an amount of movement that is typical during inhalation.

In some embodiments, the minimal amount of movement is typical during inhalation for the authenticated individual.

In some embodiments, the processor is configured to control fluid delivery and to cause fluid delivery to be prevented or stopped, reset authentication, or both if the predefined minimal range is exceeded.

In some embodiments, the processor is configured to perform at least one of: prevent substance delivery until the authentication is valid; permit substance delivery only after the authentication is valid; stop substance delivery once the authentication is reset; and lock the device once authentication is invalid.

In some embodiments, the fluid delivery device may include a heating element positioned to heat the substance within the reservoir, wherein the processor is configured to perform at least one of: prevent the heating element from heating above a predefined threshold until the authentication is performed; and permit the heating element to heat above a predefined threshold only after the authentication is successful; and reduce or stop the heating element's heat emission once the authentication indication is reset.

In some embodiments, the fluid delivery device may include electric contacts for engaging electric contacts associated with the reservoir and positioned to deliver an electric current to a heating element associated with the reservoir and configured to heat the substance within the reservoir, wherein the processor is configured to control the delivery of the electric current to cause at least one of: prevent the heating element from heating above a predefined threshold until the authentication is performed; and permit the heating element to heat above a predefined threshold only after the authentication is successful; and reduce or stop the heating element's heat emission once the authentication indication is reset.

In some embodiments, the processor is configured to analyze the waves to determine if the individual is below a threshold age.

In some embodiments, the processor is configured to analyze the waves to determine if the individual is above a threshold age.

In some embodiments, the analysis is based on biometric data input to the processor.

In some embodiments, the biometric data includes at least one of gender, ethnicity, geographical origin, or any combination thereof.

In some embodiments, the processor is configured to: compare the detected waves or a result of analysis of the detected waves with an oral signature of one or more of a plurality of registered individuals, and determine whether the individual is one of the plurality of registered individuals, wherein the oral signature comprises a wave reflection data or a result of analysis thereof indicative of an individual or an individual's property.

In some embodiments, the processor is configured to derive an oral signature of the individual, using the detected waves.

In some embodiments, the processor is configured to: retrieve, from a database associated with the fluid delivery device, a stored oral signature, and identify the individual based on a comparison between the oral signature of the individual and the stored oral signature.

In some embodiments, the processor is configured to identify the individual based on the detected waves.

In some embodiments, the processor is configured to: cause the wave generator to transmit periodically for a predefined period of time or for a predefined number of transmissions, and analyze all waves received from the sensor for the predefined period of time or after the predefined number of transmissions to authenticate the individual.

In some embodiments, the processor is configured to repeat authentication at a predetermined interval.

In some embodiments, the fluid delivery device is a substance administration device configured to administer the substance to an authorized individual, and wherein the processor is configured, only if the individual is identified as an authorized individual, to permit the substance administration device to administer the substance.

In some embodiments, the substance includes a substance selected from a group of substances consisting of substances derived from cannabis, substances derived from tobacco, cannabinoids, nicotine, pharmaceuticals, and controlled substances.

In some embodiments, the fluid delivery device is an electronic fluid delivery device.

In some embodiments, the fluid delivery device is a substance delivery device.

In some embodiments, the fluid includes ambient air and the device is configured to deliver the substance carried by the air.

In some embodiments, the fluid delivery device may include a flow valve that regulates fluid flow during inhalation by the individual of the fluid delivery device, wherein the processor is configured to control the flow valve based on the authentication.

In some embodiments, if the authentication indicates that the individual is a child, then the processor is configured to prevent the electronic fluid delivery device from flowing the substance through the opening.

In some embodiments, the processor is configured to prevent the electronic fluid delivery device from flowing the substance through the opening if the authentication does not indicate that the individual is an adult.

In some embodiments, the fluid delivery device may include a pressure dependent flow valve such that flow through the valve occurs during inhalation via the fluid deliver device only when a generated pressure within the fluid delivery device exceeds a threshold and wherein the wave generator transmits waves partially or only as long as the valve is closed.

In some embodiments, the fluid delivery device may include a sensor configured to detect inhalation of the individual via the fluid delivery device.

In some embodiments, the processor is configured to authenticate each time an inhalation via the fluid delivery device is performed by the individual.

In some embodiments, the processor is configured to authenticate at least once before delivery of the substance and at least once during delivery of the substance.

In some embodiments, the processor is configured to prevent the substance from flowing through the opening if the individual is not successfully authenticated In some embodiments, the fluid delivery device may include an alarm output device that outputs an alarm based on authentication, wherein the alarm is an audio alarm or a visual alarm.

In some embodiments, the processor is configured to issue a notification based on authentication, wherein the notification is output by the fluid delivery device, by a remote device, or both.

In some embodiments, the processor is configured to authenticate a predetermined number of times before activating the device and/or during device operation.

In some embodiments, the fluid delivery device may include a memory for storing usage information, authentication information, registration information, or any combination thereof.

In some embodiments, the processor is configured to perform a registration process in which the individual is registered.

In some embodiments, for the registration process the processor is configured to extract and record from the received at least portion of reflections of the waves at least one oral signature and register the at least one signature.

In some embodiments, the processor is configured to require a security token when performing the registration process.

In some embodiments, the token includes an oral signature of an authorized individual and an indication of the authorization.

In some embodiments, the processor is configured to perform the registration process only once per individual and/or per substance regime.

In some embodiments, the wave generator and the sensor are embedded jointly on a common hardware element.

In some embodiments, the wave generator is a speaker.

In some embodiments, the at least one of the wave generator and the sensor is housed within a covering.

In some embodiments, the fluid delivery device may include a structure for positioning the fluid delivery device onto nose, lips, and/or teeth of the individual such that the wave generator and the opening are in a desired position.

In some embodiments, desired position comprises positioning a portion of the housing, through which waves generated by the wave generator are released, within the mouth of the individual to contact a lip of the individual or not contact the lips of the individual.

In some embodiments, the structure includes a plurality of structures, each configured to allow the fluid delivery device to have a distinct position within an oral cavity of the individual.

In some embodiments, the processor authenticates only when the fluid delivery device is positioned according to a groove in the structure.

In some embodiments, the processor authenticates only when the fluid delivery device is positioned according to the groove in the structure which correlates with authentication data available to the fluid delivery device.

In some embodiments, the processor authenticates upon receiving an indication that the individual is inhaling via the opening.

In some embodiments, a duration between the individual inhaling and analysis of whether the individual is authenticated or not is 10-100 ms.

In some embodiments, the authentication and substance delivery are performed within a single inhalation of the individual.

In some embodiments, the processor is configured to authenticate and to control the substance delivery based thereon in a single inhalation of the individual.

In some embodiments, the processor uses machine learning to determine authentication.

In some embodiments, the processor is configured to normalize one or more of the detected waves with respect to a predetermined reference wave signal of the sound of the environment.

In some embodiments, the processor is configured to determine and cancel environmental noise.

In some embodiments, the processor is configured to filter the detected waves that are below a predefined threshold.

In some embodiments, the predefined threshold is below $-6$, $-7$, or $-8$ Decibels.

In some embodiments, the fluid delivery device is selected from the group consisting of a medical inhaler, a vaporizer, an e-cigarette, and a nasal applicator.

Some embodiments may provide a substance delivery device for delivery of a substance to an individual, the substance delivery device may include: a reservoir region for housing a reservoir of the substance within the substance delivery device; a wave generator for transmitting waves towards the mouth of the individual or a portion thereof; a sensor to detect at least a portion of reflections of the waves transmitted by the wave generator; and a processor coupled to the sensor and configured to: receive waves from the sensor; authenticate the individual based on at least a portion of the detected waves; and control the delivery of the substance to the individual based on the authentication.

In some embodiments, the substance delivery device may include a conduit for delivery of the substance to or through the mouth of the individual In some embodiments, the substance includes nicotine.

In some embodiments, the reservoir includes tobacco.

In some embodiments, the reservoir of nicotine includes a liquid containing nicotine.

Some embodiments may provide a fluid delivery device for delivery of a substance to an individual, the fluid delivery device may include: a reservoir region configured to house a reservoir of the substance within the fluid delivery device; a sensor configured to detect at least a portion of reflections of soundwaves from the individual; and a processor coupled to the sensor configured to authenticate the individual based on the at least portion of reflections of the soundwaves, wherein the reflections are reflection of soundwaves produced by the individual by inhalation causing airflow in the direction of the oral cavity of the individual via at least one of the individual's nose and the fluid delivery device.

In some embodiments, the fluid delivery device may include at least two sensors positioned to detect at least a portion of reflections of the soundwaves from the individual.

In some embodiments, the reflections are reflections of soundwaves produced by the individual without making a voice.

Some embodiments may provide a device for obtaining an oral signature of an individual, the device may include: a housing for positioning at least a portion of the device within a mouth of the individual; and a sensor connected to the housing configured to receive reflected waves from the mouth of the individual, the reflected waves being reflected from one or more of: airflow soundwaves generated by inhalation or exhalation of the individual; and waves generated by a wave generator; wherein the device is associated with a processor, configured to generate an oral signature of the individual using the reflected waves and with a database configured to store at least oral signature.

Some embodiments may provide a device for obtaining an oral signature of an individual, may include: a housing for positioning at least a portion of the device within a mouth of the individual, the housing comprising a wave exit; and at least one of: a wave generator connected to the housing and positioned relative to the wave exit to cause waves generated by the wave generator to transmit through the wave exit during operation, and a connector for connecting a wave generator to the housing and positioned relative to the wave exit to cause waves generated by the wave generator to transmit through the wave exit during operation, wherein positioning the at least a portion of the device within at least a portion of a mouth of the individual causes the wave exit to be at a predetermined position with respect to the mouth of the individual.

In some embodiments, the device may include at least one waveguide for guiding waves from the wave generator to the wave exit.

In some embodiments, the wave guide is a sound guide.

Some embodiments may provide a mouthpiece for a fluid delivery device, the mouthpiece may include: a housing having at least one opening to allow a fluid to flow between the mouthpiece and the oral cavity of an individual; and at least one structure for associating at least one of a wave generator component and a wave sensor component to the mouthpiece, the wave generator component for transmitting waves toward the individual and the wave sensor component for receiving at least a portion of reflections of the waves from the individual.

In some embodiments, the mouthpiece may include at least one groove to direct positioning of the mouthpiece in a mouth of the individual.

In some embodiments, the mouthpiece may include a reservoir, coupled to the housing, for holding a substance for delivery by the fluid delivery device.

Some embodiments may provide an e-cigarette for delivery of nicotine to an individual, the e-cigarette may include: a reservoir position for housing a reservoir of nicotine within the e-cigarette; a wave generator for transmitting waves towards the individual; a wave sensor to detect at least a portion of reflections of the waves from the individual; and a processor coupled to the wave sensor to: authenticate the individual based on the at least portion of the reflections of the waves, compare the at least portion of the reflection of the waves with a signature of one or more of a plurality of registered individuals, to determine whether the individual is one of the plurality of registered individuals, and determine whether an age of the individual is above or below an age threshold.

Some embodiments of the systems and methods that are described herein may relate to authentication in general. Such systems and methods can be used whenever authentication of one of more individuals or classes of individuals is required in order to access or provide access to one or more of a location, data, services, locations (physical or electronic, such as a website), a device, a system, and/or a service.

Some benefits relating to embodiments disclosed herein, are with respect to substance delivery devices, which are used to deliver a substance into or via an individual's mouth. Examples for such devices include pulmonary delivery devices (for example, inhalation devices, electronic cigarettes, and vaping products).

In some embodiments use of such devices may be controlled, for example according to a property (for example age), prescription, and/or license. In such cases, authentication during or in proximity with the usage of the device may serve to prevent or significantly reduce abuse by non-authorized individuals and/or for non-authorized uses. For example, authentication of an individual during use may control substance (e.g., drug) delivery via an inhalation device, or limit smoking of an electronic cigarette by children.

One advantage of some embodiments of the invention includes having biometric identification that is difficult or impossible be copied remotely.

Another advantage of some embodiments of the invention includes restricting access to fluid delivery devices to the authorized individual after that individual has been authorized to use the device. This may serve, for example, to prevent an unauthorized individual from accessing the device after the authorized individual. In some embodiments, biometric data is obtained during the use of the device, which can allow for repeatedly authenticating the authorized individual.

Another advantage of some embodiments of the invention includes performing biometric identification with oral devices. Another advantage can include performing biometric identification that is directly linked to device use to, for example, prevent use by an unauthorized individual during operation. For example, if an authorized individual continues to provide biometric data during use but is not the actual individual using the device (e.g., authorized person provides a fingerprint while unauthorized person inhales), the invention can advantageously prevent this unauthorized use.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate correspond ding, analogous or similar elements, and in which:

FIG. 2A, FIG. 2B and FIG. 2C are schematic diagrams of a fluid delivery device according to some embodiments of the invention.

FIG. 3C are graphs showing an example of a received wave without a cover on the wave sensor and FIG. 3D are graphs shown an example of the same received waves with a cover on the wave sensor, according to some embodiments of the invention.

FIG. 5A is a flow chart of a method for registering an individual and for delivery of a substance to the individual, according to some embodiments of the invention.

FIG. 5C is a flow chart of a method for authenticating an individual for delivery of a substance to the individual, according to some embodiments of the invention.

FIGS. 8A and 8B are a T-distributed Stochastic Neighbor Embedding (t-SNE) graph visualizing a possible distinction between adults and children according to received wave reflections, wherein FIG. 8B is an enlarged portion marked by a dashed rectangle of FIG. 8A.

It will be appreciated that for simplicity and clarity of illustration, elements shown in the figures have not necessarily been drawn accurately or to scale. For example, the dimensions of some of the elements can be exaggerated relative to other elements for clarity, or several physical components can be included in one functional block or element.

DETAILED DESCRIPTION

Figure 1A:
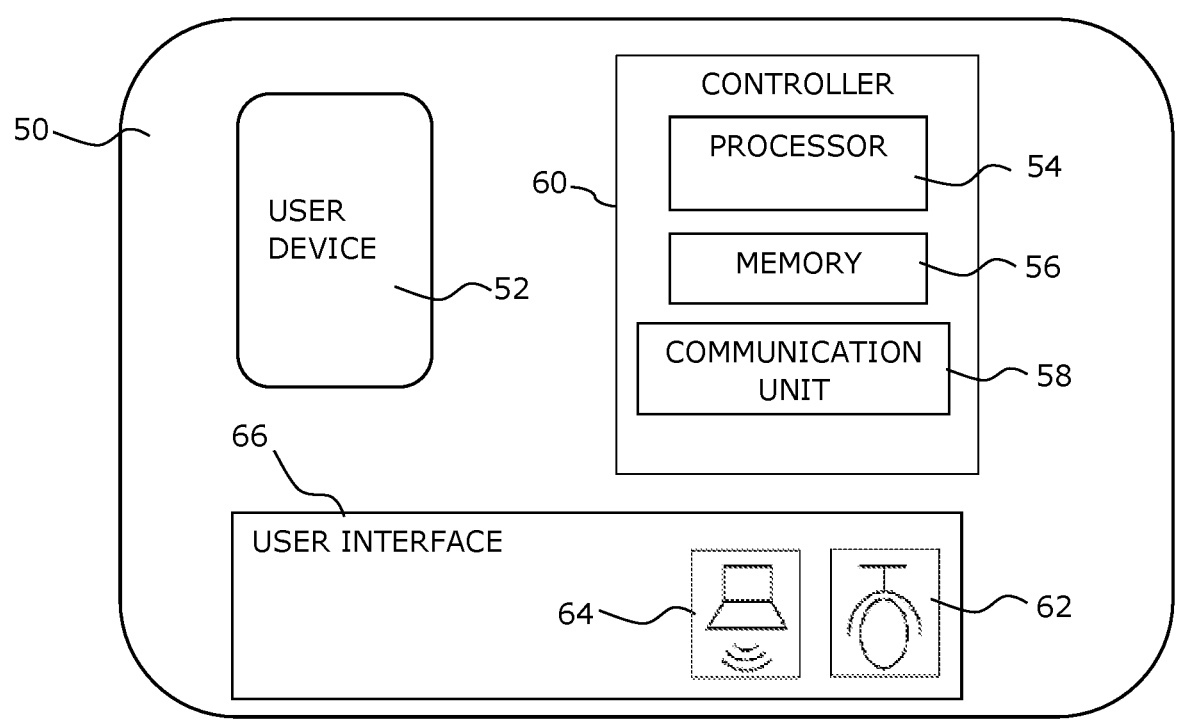
FIG. 1A is a block diagram of a system for obtaining an oral signature of an individual, according to some embodiments of the invention.

FIG. 1A is a block diagram showing an individual authentication system 50, that may be used in conjunction with some embodiments of authentication method. In accordance with some embodiments, an authentication of an individual may be required, for example, in order to provide the individual with access to a device, a location and/or a service.

In some embodiments, the system 50 disclosed herein allows registration of an individual, by transmitting a wave towards the individual's mouth, recording a reflected wave and associating the reflected wave as a signature associated to any of: the individual's identity; at least one property of the individual, such as age, allergies, disorders; and an authorization indication.

Some embodiments of the individual authentication system may combine wave information with additional specific information of that individual that is provided without direct control by the user in the determination of identity of the individual. Such additional information may increase the precision and/or specificity of detection. For example, a biometric property (e.g., fingerprint), detection of an RFID element, a typical inhalation profile of an individual, typical timing of inhalation, a typical exhalation profile of an individual, typical timing of exhalation, and/or typical positioning of an inhalation device during inhalation or exhalation (as sensed for example by pressure sensor for the inhalation/exhalation profile, accelerometer for the inhalation device position during inhalation/exhalation).

In accordance of some embodiments, device 52 operation (e.g., activation, deactivation and/or enablement of a given function) is controlled by authentication system 50. Authentication system 50 comprises user interface unit 66 and a controller unit 60. User interface unit 66 and controller unit 60 may both be components of the same device, optionally device 52, or alternatively be distributed in one or more distinct devices.

Controller unit 60 may include a processor 54, a memory 56 and optionally a communication unit 58. Processor 54 may be, for example, a chip or any suitable computing or computational device. Memory 56 may include a double data rate (DDR) memory chip, a flash memory, a volatile memory, a non-volatile memory, a cache memory, or any other suitable memory unit or storage unit. Memory 56 may store any executable code, e.g., an application, a program, a process, task or script. The executable code may include instructions for controlling at least some of the components of a device 52 according to embodiments of the invention or any other codes or instruction for executing methods according to embodiments of the present invention. The executable code may be executed by processor 54.

In some embodiments, controller 60 includes a communication unit 58. Communication unit 58 may include any communication module configured to communicate wirelessly (or wired) with an external computing device, for example, an external server or a personal electronic device. The sever may be any computing and storing platform, for example, a cloud-based computing service and a cloud-based storage that is configured to communicate with controller 60. The server may include data related to the operation of the device 52. For example, the server may store authentication data of plurality of individuals. A personal electronic device may be for example, a personal computer, a desktop computer, a mobile computer, a laptop computer, a notebook computer, a tablet, a smartphone, a smartwatch and the like.

In some embodiments, authentication system 50 may operate without connectivity to an external device, hence authentication may be performed independently in device 52 without any external communication.

In some embodiments, device 52 is an inhaler device. In these embodiments, memory 56 may store executable code, which may include instructions for controlling at least some of the components of the inhaler device e.g., airflow system, heating operator, dosage information, substance delivery regimen, etc. The inhaler may for example be configured to provide medical treatment, wellbeing and/or for non-medical purposes.

Communication unit 58 may communicate with a server. Server may also store a plurality of operation profiles each being associated with the delivery of different amounts of one or more substances from a source material associated with an authenticated individual. In some embodiments, communication unit is operative for automatically adapting a replacement inhaler device to the personal usage patterns of at least one individual defined during the usage in an original inhaler device.

In some embodiments, user authentication system 50 may include a user interface 66 configured to generate and/or record personal data of an individual. In some embodiments, such personal data can relate to waves reflected in the mouth of an individual. In some embodiments such personal data can relate to or include waves reflected in other body cavities of an individual, such as nasal or tympanic cavities.

In some embodiments, the wave includes a sound wave. In some embodiments, the wave includes an electromagnetic wave, including for example one or more of visible light, ultra-violet light, infra-red light, and radiofrequency. The energy transmitted to the individual by the wave is such that will be below perception and will not cause harm or damage. Optionally combinations of waves, including sound waves and electromagnetic waves can be used.

In some embodiments, user interface may include a wave generator 64 and a wave sensor 62 (e.g., a recorder).

In some embodiments, wave generator 64 may be programmed by a frequency generator to send a wave (e.g. a sound wave) with predefined amplitude, frequency, duration and offset parameters. Optionally, the wave frequency of any transmitted sound waves may be external to the human hearing frequency range, e.g., lower than 20 [Hz] or higher than 20 [kHz]. In some embodiments, the transmitted soundwaves have a frequency below 500 Hz. In some embodiments, the transmitted sound waves are or include waves in the ultrasound frequency range. In some embodiments, the transmitted waves are or include waves at a range of 20 kilohertz to 1 gigahertz. In some embodiments, the transmitted waves are or include waves at a range of 1 gigahertz to 3 gigahertz, or higher. Optionally, wave generator 64 generates sound waves only at a frequency range that is typically heard by minors or children but not by adults (such as 15-20 [kHz]). A potential benefit of such frequency range is that a system configured to identify and reject usage by minors or children, may also cause them discomfort and deter additional attempts.

In some embodiments, wave generator 64 includes a passive wave generator producing white noise. In some such embodiments, at least two wave sensors 62 (e.g., microphones) are used. Optionally, at least one wave sensor 62 is configured (e.g., positioned or being directionally restricted) for detecting the transmitted waves in real time (thus identifying properties of the transmitted waves) and at least one other wave sensor 62 is configured (e.g. positioned or being directionally restricted) for receiving reflections. In some such embodiments, white noise is produced continuously during use of the fluid delivery device, including after authentication was completed.

Once wave generator 64 generates a wave and for a predetermined time, a wave, including the wave generated by wave generator 64, the reflected wave is translated by wave sensor 62 to electronic signals and stored. Optionally, the data is translated to electric voltage analog signal. The electric voltage analog signal is captured and saved by an oscilloscope, in some embodiments. Optionally transmission by wave generator 64 and capturing of reflected waves via wave sensor 62 are sequential. In some embodiments, wave generator 64 transmission partially or completely overlaps capture. In some embodiments, wave generator 64 transmits continuously and capturing via wave sensor 62 is performed intermittently.

In some embodiments, authentication system 50 is designed to prevent recording background noise during the wave transmittal. Optionally, controller 60 may essentially prevent operation which produces noise. Optionally, heating or airflow during the wave transmittal. Optionally, controller 60 may cause preventing significant airflow although inhalation or exhalation are attempted by an individual. Optionally by a pressure sensitive valve that would open at a given pressure while the sensing is performed earlier and/or by a controlled valve that is opened once sensing is complete or even only after the individual was authenticated. Additionally, or alternatively, the system may improve the quality of the recorded sound by enclosing at least one of the wave generator 64 and the wave sensor 62 by an intermediate enclosure. Covering the wave generator 64, and/or the wave sensor 62 from being exposed to the mouth of the individual. The wave generator 64, and/or the wave sensor 62 can be disposed in miscellaneous media, including gas and/or liquid to improve wave propagation properties.

Figure 1B:
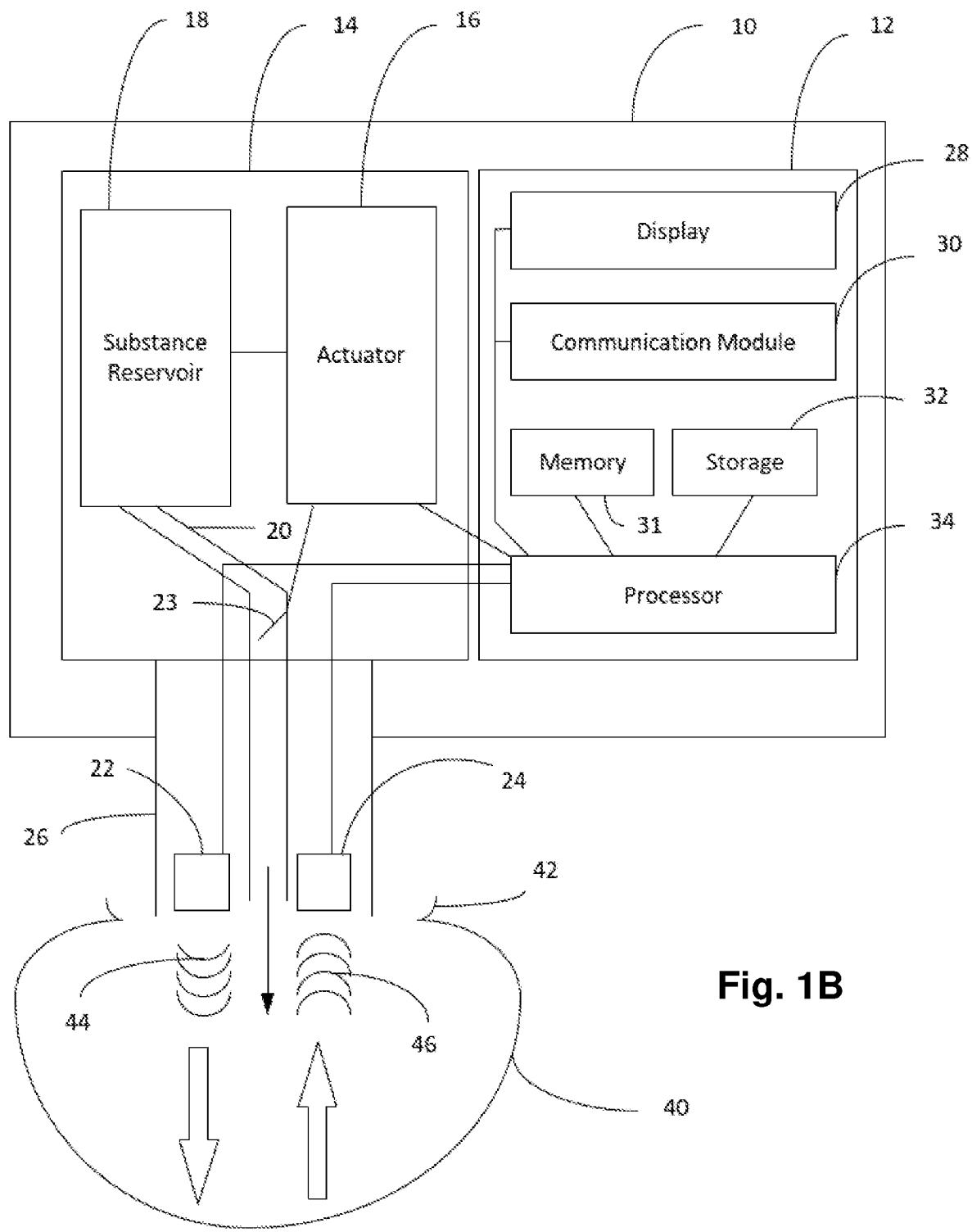
FIG. 1B is a block diagram of a fluid delivery device including the system of FIG. 1A for delivering a substance to an individual, according to some embodiments of the invention.

FIG. 1B is a block diagram of a fluid delivery device 10 for delivery of a substance to an individual including the system of FIG. 1A, according to some embodiments of the invention.

In some embodiments, fluid delivery device 10 includes a reservoir region for holding a reservoir 18 of a substance to be delivered to an individual. Optionally, a reservoir 18 is included in the reservoir region. In some embodiments, fluid delivery device 10 further includes a wave generator 22 configured to transmit waves, a sensor 24 configured to detect at least a portion of reflections of the waves transmitted by the wave generator 18, and a processor 34 configured to authenticate the individual based on the at least portion of reflections of the waves from the individual. Optionally, processor 34 is configured to control the delivery of the substance based on the authentication.

In various embodiments, device 10 is an authentication device for authenticating an individual. In such embodiments, the device can comprise wave generator 62, sensor 64 and memory 56 on which at least one oral signature is stored, and a processor 34 that is operable to authenticate an individual by comparing an oral signature taken from the individual using wave generator 62, sensor 64 and comparing it with the oral signature stored in the memory. The authentication device may include a mouthpiece structured for insertion into the mouth of the individual such that waves generated by wave generator 62 are transmitted from the mouthpiece directly into at least one of the lips and oral cavity of the individual. In some embodiments, authentication device is couple to or included in a fluid delivery device, a substance delivery device, or a device for detecting at least one substance exhaled by the individual. In some embodiments authentication device is used to authenticate individuals and transmit the authentication result by wired and/or wireless communication to one or more separate database, system and/or device.

In some embodiments, fluid delivery device 10 includes a substance delivery portion 14, an authentication module 12, an opening 26, a wave generator 22 and a wave sensor 24. In some embodiments, the fluid delivery device is a device that may deliver to an individual a fluid (e.g., a gas, such as air and/or a liquid), optionally via the individual's mouth. In some embodiments, the fluid delivery device 10 may deliver a fluid into an individual's lungs. The delivered fluid may serve as a carrier of a substance. In the case of pulmonary delivery, the gas (optionally air) can serve as a carrier for the substance. The substance may be inhaled in any form, including, for example, vapor, powder and/or aerosol. Optionally, the devices may be electronically controlled. In some embodiments, the fluid delivery device 10 may be a medical device. Examples for fluid delivery devices for pulmonary delivery may include e-cigarettes, vaping devices and inhalers, used for medical and/or non-medical purposes. Optionally, the fluid delivery device 10 is an inhalation actuated device. In some embodiments, the fluid delivery device may be a device though which an individual may inhale air solely for the operation of authentication module 12.

The substance delivery portion 14 includes a reservoir 18, an actuator 16, conduit 20 (e.g., dispensing duct) and a valve 23. The authentication module 12 includes a processor 34, memory 31, storage 32, communication module 30 and a display 28.

The reservoir 18 can be coupled to the actuator 16 and the opening 26 via a conduit 20 (e.g., a dispensing duct). The actuator 16 can be coupled to the valve 23 positioned within the conduit 20 or at any position that can regulate flow of the fluid within the fluid delivery device. The actuator 16 may include a valve configured to direct the fluid within the device between alternative conduits based on the authentication. The processor 34 can be coupled to the wave generator 22, the wave sensor 24, the memory 31, the storage 32, the communication module 30, and/or the display 28.

The wave generator 22 can be an air pressure wave generator (e.g., generating sound waves, ultrasound waves). The wave generator 22 can be a low frequency buzzer. The wave generator 22 may be a passive noise generator. The wave generator 22 may be a device such that the sound transmitted includes a sound generated as a byproduct of use and/or operation of the device. For example, airflow through the device 10 (e.g. due to inhalation and/or exhalation by an individual using the device) may generate a sound. The wave generator 22 can be a MEMS based component. The wave generator 22 can transmit sound waves or electromagnetic waves. The wave generator 22 can transmit a single pulse wave and/or a plurality of pulsed waves. The wave generator 22 can include a plurality of wave generators, generating different waves.

In some embodiments, the fluid delivery device 10 may operate based on reflections of soundwaves produced by the individual. The soundwaves produced by the individual may, for example, be soundwaves caused by inhalation causing airflow in the direction of the oral cavity of the individual via at least one of the individual's nose and the fluid delivery device or sounds of inhalation or exhalation or any other non-vocal sounds transmitted in the direction of the individual's mouth, optionally excluding speech and other vocalizations. In some embodiments, fluid delivery device 10 includes a reservoir region configured to house a reservoir of the substance within the fluid delivery device 10 and a sensor configured to detect at least a portion of reflections of soundwaves from the individual, and a processor coupled to the sensor configured to authenticate the individual based on the at least portion of reflections of the soundwaves. For example, the reflections may be reflections of soundwaves produced by the individual without making a voice. Examples include the airflow sounds of one or more of inhalation via the mouth, nose and/or via the fluid delivery device 10 and/or exhalation. In some embodiments, the fluid delivery device 10 includes at least two sensors positioned to detect at least a portion of reflections of the soundwaves from the individual, especially if the generated sound is uncontrolled or unpredictable. In various embodiments, the fluid delivery device 10 may operate based solely on reflections of soundwaves produced by the individual, based solely on reflections of waves produced by the wave generator 22 or both.

The wave generator 22 may generate waves of any type of form, including soundwaves and electromagnetic waves. The sound waves can include or consist of controlled and/or random uncontrolled white noise. In some embodiments, the generated waves have a predefined pattern over time. The pattern may, for example, include different frequencies transmitted in sequences and/or in parallel, each having predefined timing, duration and/or power and/or different types (e.g. a combination of soundwaves and electromagnetic waves) in any pattern.

In some embodiments, a transmitted wave pattern is adjusted (e.g., twisted) to conform with inhalation dynamics of the inhaling individual. For example, the transmission may commence based on sensing inhalation (e.g., possibly timed with a predefined delay). In some examples, transmission may commence once essentially stable inhalation is detected.

In some embodiments, the wave generator 22 may by a speaker. In some embodiments wave generator 22 is a or includes a passive structure positioned in a fluid delivery device such that it produces noise as air flows through or next to it (e.g. plurality of flapping sheets or a fan). In some embodiment a passive wave generator is breath actuated.

In some embodiments, the wave generator 22 transmits electromagnetic waves having one or more frequencies of visible light, ultra-violet light, infra-red light, and radiofrequency. In some embodiments, other ranges of electromagnetic waves may also be applicable. In some embodiments, the wave generator 22 transmits sound waves. In some embodiments, the transmitted sound waves are in the ultrasound frequency range. In some embodiments, the transmitted waves are or include waves at a range of 20 kilohertz to 1 gigahertz. In some embodiments, the transmitted waves are or include waves at a range of 1 gigahertz to 3 gigahertz, or higher. In some embodiments, the transmitted sound waves are in the frequency range of human hearing, e.g., have a frequency between 20 hertz to 20 kilohertz. In some embodiments, transmitted soundwaves have a frequency below 500 Hz. In some embodiments, the sound waves have a frequency range that may be annoying for individuals below a threshold age but inaudible for older ones. For example, sound waves between 15-20 kilohertz are typically only heard by children. Thus, the device can transmit sound waves in this range to cause children to be unable and/or reluctant to use the fluid delivery device 10. In some embodiments, the sound waves are inaudible to the human ear (e.g., to avoid causing mental or physical harm).

The wave sensor 24 can be a sound sensor (e.g., e.g., microphone, directional microphone array). The sensor 24 can be a piezoelectric microphone. The sensor 24 can be a MEMS based component. The sensor 24 can include a noise dumper, in order to reduce the recorded background noise and increase the portion of recorded data typical to the individual. The sensor 24 can include a transducer, operative to convert received waves into electrical signals. Alternatively (not shown) the sensor and the converter can be separate components, each of them may be either analog or digital.

The authentication module 12 (or processor 34) can be configured to communicate with a remote device (e.g., a network server, a cloud based server, etc., medical service provider, etc.), for example, to update an operating system, to obtain and/or update, authentication data relating to an authorized individual or individuals, a list with details of one or more authorized individuals, and/or administration scheme or schemes associated with the authorized individual or individuals. Authentication module 12 may be distributed in more than one location. For example, the display 28 and/or storage 32 may be in a smartphone. In various embodiments, one or more elements of the authentication module 12 are housed on a computing device that is in wired or wireless communication with the fluid delivery device 10.

In various embodiments, wave sensor 24 and/or wave generator 22 are incorporated in fluid delivery device 10. In various embodiments, wave sensor 24 and/or wave generator 22 are incorporated in a mouthpiece of fluid delivery device 10. In various embodiments, wave sensor 24 and/or wave generator 22 are incorporated in a probe (not shown), operative to be coupled to the device and/or to authentication unit 12. In some embodiments the probe includes any of wave sensor 24, wave generator 22, and any of the components of authentication unit 12. In some embodiments, the probe includes, or have access to, registration data of the individual, and operative to serve as an identification object. Optionally, the identification object may be coupled to one or more devices in order to perform authentication and receive access to the device.

The display 28 can display information relating to the use of fluid delivery device 10 and/or to the individuals, or to a care worker, or others. The memory 31 can store usage information, authentication information, registration information or any combination thereof. In various embodiments, the fluid delivery device 10 includes a plurality of wave generators and/or a plurality of sensors. In various embodiments, one or more wave generators and one or more sensors are in the same housing.

In some embodiments, the valve 23 is a pressure dependent flow valve such that the substance only flows through the valve during inhalation, for example, when a generated inhalation pressure exceeds a threshold. In some embodiments, the wave generator 22 transmits only partially or only as long as the valve 23 is closed. In various embodiments, the valve is electrical and/or mechanical.

In some embodiments, the fluid delivery device 10 does not include the authentication module 12 and only includes a processor. In some embodiments, the fluid delivery device 10 does not include the valve 23. In various embodiments, one or more of the elements of the authentication module 12 are excluded from the fluid delivery device 10.

The components of the fluid delivery device 10 as shown in FIG. 1A can be housed in a single housing or in multiple housings. In various embodiments, reservoir 18 can house one or more substances of one or more cannabis derived substances, cannabinoids, prescribed drugs, medicine, pharmaceuticals, nicotine, tobacco, any substance known for smoking or smoking alternative, substances to cause various flavors and/or scents, controlled substances and substances derived from cannabis, substances derived from tobacco, or any substance as is known in the art.

The fluid delivery device 10 can be an electronic fluid delivery device and/or be battery/solar powered.

In some embodiments, the fluid delivery device 10 includes a notification module (e.g., an alarm). The notification module can be issue audio notification, a visual notification or both (one or more of which may include an alarm). The notification can be triggered if the individual is identified as being below an age threshold and/or is identified as not being an authorized individual. In some embodiments, the alarm is located on a remote device (e.g., a smartphone and/or other computer in communication with the authentication module).

During operation the authentication module 12 can instruct the wave generator 22 to transmit waves when the opening 26 (e.g., mouthpiece) is positioned towards a mouth 42 (e.g., lips, tissue surrounding the lips, and/or oral cavity) of an individual, and the wave generator can transmit waves 44 towards the individual. This can take place, for example, upon request (e.g., pressing on a button, inhaling through a fluid delivery device, placing the mouthpiece in one's mouth, providing an activation authorization, for example via software or by inputting a code etc.) and/or upon use (first use and/or other uses). As shown in FIG. 1A, the opening 26 is positioned within the oral cavity 40, however, the opening 26 can be positioned in any position that allows the waves generated by the wave generator to impinge upon the mouth 42. In various embodiments, the waves are transmitted and/or received when towards the individual when the wave generator 22 is in direct physical contact with the mouth 42, when the sensor 24 is in direct physical contact with the mouth 42, or any combination thereof.

At least a portion of the waves can reflect from the mouth 42 of the individual causing reflections 46 that are detected by the sensor 24. In some embodiments, at least a portion of the waves 44 are absorbed by the oral cavity 40. In some embodiments, a sensor (not shown) is positioned a location that allows the sensor to detect absorption of the waves by the oral cavity 40 and/or mouth 42.

In some embodiments at least one of wave generator 22 and sensor 24 is positioned in direct physical contact with the mouth during the wave transmittal. In some embodiments, at least one of wave generator 22 and sensor 24 is positioned between the lips and in direct physical contact with one or both of the lips. In some embodiments at least one of wave generator 22 and sensor 24 is positioned in direct physical contact with one or more teeth. In some embodiments at least one of wave generator 22 and sensor 24 is positioned in direct physical contact with one or more of the tongues, and/or inner part of the mouth. In some embodiments wave generator 22 and sensor 24 are positioned within the individual's oral cavity and are not in contact with any organs (e.g. lips, teeth, inner part of mouth, and/or tongue).

In some of the embodiments where at least one of wave generator 22 and sensor 24 is enclosed within an enclosure, at least one enclosure is positioned in direct physical contact with a part of the mouth during the wave transmittal. In some embodiments, at least one enclosure is positioned between the lips and in direct physical contact with one or both of the lips. In some embodiments at least one enclosure is positioned in direct physical contact with one or more teeth. In some embodiments at least one enclosure is positioned in direct physical contact with one or more of the tongues, and/or inner part of the mouth. In some embodiments wave all enclosures are positioned within the individual's oral cavity and are not in contact with any organs (e.g. lips, teeth, inner part of mouth, and/or tongue).

The wave sensor 24 can transmit the detected reflections to the processor 34. The processor 34 can process the detected reflections to determine whether the individual has permission to use the fluid delivery device 10. If the individual has permission to use the fluid delivery device 10, the individual can be authenticated.

In some embodiments, a portion of the reflections is used for analysis, and the portion is selected to conform with the inhalation dynamics of the inhaling individual. For example, the selected portion may commence based on sensing inhalation (possibly timed with a predefined delay). In some examples, the selected portion may commence once essentially stable inhalation is detected (e.g., when a variation in pressure over time as measured within the fluid delivery device 10 is within a predefined range).

In some embodiments, the transmission of waves is modified according to sensed inhalation dynamics of the inhaling individual. For example, the transmission of waves may be modified according to one or more of a rate of change in pressure within the fluid delivery device 10 and a rate of airflow through the fluid delivery device 10. For example, in cases of relatively rapid or strong inhalation, the duration of a transmission patten may correlate inversely to one of these rates. The faster pressure buildup occurs, the shorter the duration of transmission or the earlier the commencement of transmission. To adjust the duration of a patten, the transmission may be adjusted by removing or adding one or more of transmitted frequencies, by changing a duration of transmission of one or more frequencies and/or the duration of one or more periods between transmissions, and/or by allowing, adjusting, and/or preventing overlaps between one or more transmitted waves and any combination thereof.

Optionally, adjusting is performed more than once during an authentication event in response to the sensed changes, such that a patten or portions thereof may be shortened and/or lengthened any number of times during the authentication event. As a result, the precise transmitted signal may vary between individuals and/or between inhalations of the same individual. The adjusting may be performed in real time and/or be based on accumulated data from one or more previous authentication/registration events.

Upon a successful authentication of the individual, the actuator 16 can activate the delivery of a substance housed within the reservoir 18 and/or control the valve 23 to a particular position, for example, fully open or partially open. The actuator 16 can activate a heating element (not shown) that heats the substance housed within the reservoir 18. The heated substance can flow through the conduit 20 into the oral cavity 40 of the individual. Optionally, the heated substance can undergo a chemical and/or structural change as a result of temperature its heating and/or cooling. Optionally, the substance in the reservoir is liquid form and is optionally released by one or more of heating and pressure release. In some embodiments, the substance in the reservoir is in powder form and is released by heating and/or by extracting (or dispensing) powder away from the reservoir. In some embodiments the substance is in plant material is optionally released by heating or vaporization. In some embodiments, the substance is association with an air permeable structure (e.g., a pallet) from which it is extracted by allowing airflow through the structure and/or heating the structure. In some embodiments, the processor 34 controls the valve 23.

As is understood in the art, the fluid delivery device 10 can have a reservoir that is empty and filled/refilled with one or more substances. Optionally, the reservoir is replaceable. For example, in some embodiments the reservoir is in the form of distinct substance carrying units each configured for one or several substance deliveries events (e.g., capsules, chips, cannister, etc.). Such reservoirs can be stored in a magazine for automatic replacing by the fluid delivery device, or are replaceable manually.

In some embodiments, the fluid delivery device 10 can require once or several (n number) authentications prior to delivering the substance, where n is an integer value. In various embodiments, during operation, the individual is repeatedly authenticated during use of the fluid delivery device 10. The repeated authentication can occur by the processor 34 causing the wave generator 22 to transmit waves according to the desired authentication. The authentication can occur at a predefined time interval, after a triggering event, once or a predetermined number of times, with a periodicity over a predefined duration, or any combination thereof. The predefined duration and/or the periodicity can be input by an individual and/or be based on a type of the fluid delivery device 10 and/or the type of substance to be delivered. For example, for a fluid delivery device of a tobacco or nicotine e-cigarette the predefined interval can be 3-5 pulses per second. In some embodiments, for a fluid delivery device of a pharmaceutical or controlled substance, the predefined interval can be 5-10 pulses per second. The predetermined time interval can be constant (e.g., every predetermined number of milliseconds, for example, in any of the following ranges: 5-50 milliseconds, 50-200 milliseconds, 200-1000 milliseconds, every 1 second, every 5 seconds or every 10 seconds). In some embodiments, the predetermined time interval varies. For example, as substance delivery or inhalation (or exhalation) progresses, the periodicity may drop (e.g., from a periodicity of reiterating the authentication module every 30 milliseconds to reiterating it every 60 milliseconds, etc.). Optionally, for authentication that barely passes (e.g., a very young adult is identified) periodicity of the authentication process can increase (e.g., from a periodicity of reiterating the authentication module every 30 milliseconds to reiterating it every 10 milliseconds, etc.).

In some embodiments, the fluid delivery device 10 can require several (n number) transmissions to authenticate, where n is an integer value. For example, the fluid delivery device 10 can require that the wave generator transmit the wave 5 times and receive the signal 5 times, before making a determination of authentication. The determination can then be based on combined analysis of the received waves. In this manner, the authentication of an individual can be more accurate.

Authentication can involve transmitting waves, receiving at least a portion of the transmitted waves reflected from the individual, and analysis of at least a portion of the received waves. In some embodiments, analysis is performed after the waves had been received. The transmission of the waves can be continuous or sporadic or periodical. The receipt of the reflections can be continuous or sporadic or periodical. The portion of received waves selected for analysis can be continuous or sporadic in correspondence timeline of the received reflections. The selection of the portion may be in correlation to a process of inhalation by the individual. Authentication can be valid when the reflections are analyzed.

In various embodiments, the duration for transmission, receipt of reflections and analysis of the reflections is between 10-100 ms, or 30-70 ms. In some embodiments, the waves are transmitted cyclically, with waves being transmitted for 50 ms (e.g., chirp) and a then no transmission for 50 ms in order to allow waves to fade before transmitting the next wave (e.g., break). In some embodiments, the transmit/no transmit cycle occurs 3-5 times for one authentication attempt. In various embodiments, the chirp and break have different durations. In various embodiments, the chirps are the same duration while the breaks have different durations.

In various embodiments, a duration between the first wave being transmitted and/or received and the authentication being complete (e.g., first inhalation) is 100 ms-500 ms, 250 ms-300 ms, and/or 50-300 ms.

In various embodiments, the transmission of waves begins upon air flow, for example via inhalation by an individual using the device. In some embodiments, the transmission of waves begins within 1 ms from the commencement of airflow. In some embodiments, reception begins with transmission of waves. In some embodiments, reception begins at a duration d after the beginning of the transmission of waves. In various embodiments, transmission and/or reception and/or the received waves are selected for analysis at a period of time beginning between 10-75 ms from the onset of inhalation. In some embodiments, transmission and/or reception and/or the received waves are selected for analysis at a period of time beginning between 30-60 ms from the onset of inhalation. In some embodiments, transmission and/or reception and/or the received waves are selected for analysis at a period of time beginning between 20-50 ms from the onset of inhalation.

The triggering event can be actuation of the device by an individual. For example, by turning the device on, by releasing a substance from a storage location (reservoir or magazine holding reservoirs) into a use location, and/or by sensing that inhalation through the device has commenced (e.g., sensing a drop in air pressure by a sensor in the device, such as in breath actuated inhalers or by sensing a change in temperature, such as a thermometer being put in a patient's mouth).

The triggering event can be that the fluid delivery device 10 has changed its position or moved a distance greater than a predefined minimal range from a location or position where an authorization occurred. For example, an individual, during a single inhalation is typically not supposed to move more than a minimal range of movement typical of inhalation (e.g., unless an inhalation device is passed on to another individual after authentication, which it may be desired to prevent). After the individual is authenticated, if the authentication module 12 determines that the fluid delivery device has changed its position significantly (e.g., vertical displacement from a mouth elevation of the authorized individual to a waist elevation, or horizontal displacement, and/or tilting by more than 30 degrees, indicative of passing the inhalation device to another individual) delivery of the substance can stop.

The fluid delivery device 10 can include a motion detection sensor (not shown). The motion detection sensor can detect movement of the fluid delivery device 10. In some embodiments, the motion detection sensor includes a processor to process waves detected by the sensor and transmit to the processor 34 if the predefined minimal range is exceeded. In some embodiments, the motion detection sensor can be in communication with the processor 34 and the processor 34 can determine if the predefined minimal range is exceeded.

In some embodiments, exceeding the predefined minimal range can cause the fluid delivery device 10 to cease delivery of the substance (e.g., by closing the valve 23, shutting off power and/or causing a heating element to cool down) and/or cause the fluid delivery device 10 to reset authentication (e.g., behave as if the individual had not been previously authenticated).

The authentication module 12 can be preprogrammed with one or more threshold values defining predefined minimal range. Optionally, once a person is registered and uses a fluid delivery device, the threshold values are updated in view of the specific individual's typical motion in use. The authentication may be repeated for each inhalation. This can prevent transfer of the fluid delivery device from an authorized individual to one who is not authorized after the first inhalation while allowing the authorized individual to be in ordinary motion during use (e.g. taking a series of inhalations from an e-cigarette).

In some embodiments, the triggering event is inhalation of the individual. In some embodiments, each time inhalation of the individual is sensed, the fluid delivery device 10 authenticates the individual.

In some embodiments, the fluid delivery device 10 authenticates an individual at least once before delivery and at least once during delivery of the substance. In some embodiments authentication by the fluid delivery device 10 begins before delivery and overlaps a part of delivery.

The predefined minimal range can be an amount of movement that is typical during inhalation/exhalation. The predefined minimal range can be input by an individual. The predetermined number of times can be input by an individual. The predefined period of time can be based on an amount of time that the fluid delivery device 10 typically takes to deliver the substance. One or more of the predefined period of time, the predefined minimal range, and the predetermined number of times can be based on substance type.

In various embodiments, when the fluid delivery device 10 includes a heating element, the heating element can be prevented from heating above a predefined threshold until authentication is performed. The predefined threshold can be a temperature slightly (e.g., 5-50 deg. C) lower than the substance vaporization temperature, to speed up the delivery time in the event that the individual is authenticated. In some embodiments heating commences only after the individual is authenticated.

In some embodiments, the wave generator 22 may be triggered to transmit waves in a specific manner For example, wave transmission may be triggered upon initiation of inhalation by a current individual. Such initiation may be supervised, for example by an authorized individual (e.g., a medical doctor or a medical care worker, a seller at a point of sale, verifying authorization for a transaction, a welfare officer, a policeman, a pharmacist, a parent, etc.). Supervision may be most useful for wave transmission during a process of registration.

In some embodiments, for example during registration and/or authentication, feedback may be provided to the individual regarding success and/or failure of the process. The feedback can be of any type, including one or more of visual, audio and tactile signaling. In some embodiments, the feedback includes feedback provided by the fluid deliver device 10 itself (e.g. a light indication and/or a sound and/or vibration and/or written notification). In some embodiments, the instructions include an indication provided on a screen (e.g., on a PDA and/or computer). In some embodiments, written instructions and/or feedback graphics are provided.

In some embodiments, the feedback includes a recommendation for action/inaction/modification of action by the user, which may improve the result and/or allow successful authentication/registration. For example, a recorded message may be played advising the individual that he had prematurely positioned or removed the fluid delivery device 10 (e.g., from between his lips), moved it excessively during operation, positioned it at a wrong position, inhaled too fast or too slow, etc.

In some embodiments, registration and/or authentication is performed according to notifications from the fluid delivery device 10 (e.g., recorded vocal instructions on steps and/or feedback on performance). Examples can include an instruction on the beginning of the process (e.g., such as how and/or where to position the fluid deliver device 10, how to position the individual, avoiding factors that might affect the process, such as, for example, excessive motion or excessive loud noise, and/or finding a location that is positive such as a quiet relaxing comfortable location etc.).

In some embodiments, for example in a registration event, the individual may be instructed to repeat transmission/reception stages until sufficient information is obtained to register a signature. The instructions may include an instruction to repeat and/or an instruction to repeat with variation.

The fluid delivery device 10 can be a medical inhaler, a vaporizer, or an e-cigarette.

Turning to FIGS. 2A, 2B and 2C, FIG. 2A, FIG. 2B and FIG. 2C are schematic diagrams of a fluid delivery device 200 (e.g., fluid delivery device 10 as described above in FIG. 1A) according to some embodiments of the invention.

The fluid delivery device 200 includes a housing 212, a mouthpiece 201, a wave generator 202, a sensor 204, an adaptor 206, and a button 218. The housing 212 can house a reservoir, an actuator, a processor (not shown). For example, the housing 212 can house reservoir 18, actuator 16, and processor 34, as described above in FIG. 1A. In some embodiments, the fluid delivery device 200 includes a conduit (not shown) that leads from an interior of the housing (e.g., the reservoir) to the mouthpiece 201. The substance can enter the mouthpiece via an opening of fluid delivery device 200 (not shown) and exit the mouthpiece 201 at an exit aperture 216.

The button 218 can be pressed to turn the fluid delivery device 200 on and off. In some embodiments, when the button 218 is pressed a fingerprint of the individual pressing the button can be recorded.

The mouthpiece 201 can be coupled to the housing 212 via adaptor 206. The wave generator 202 and the sensor 204 can be positioned within the adaptor 206.

The housing 212 can include I/O ports that can mate with the adaptor 206 and/or the wave generator 202 and the sensor 204. The I/O ports can create electrical connection between the processor and the wave generator 202 and the sensor 204 to electrically connect the elements. The adaptor 206 can structurally mate with the housing 212 and the mouthpiece 201 to insure the respective I/O line up to cause structure and electrical connection between the components.

In some embodiments, the mouthpiece 201 can be translucent, as shown in FIG. 2B.

In some embodiments, the mouthpiece 201 includes a groove. The groove can direct an individual to position the mouthpiece on a particular part of the individual's lips, or a particular position with respect to the individual's teeth or oral cavity or any other part of the mouth. In some embodiments the device is configured to alerting the individual to return to a predefined position.

Figure 2D:
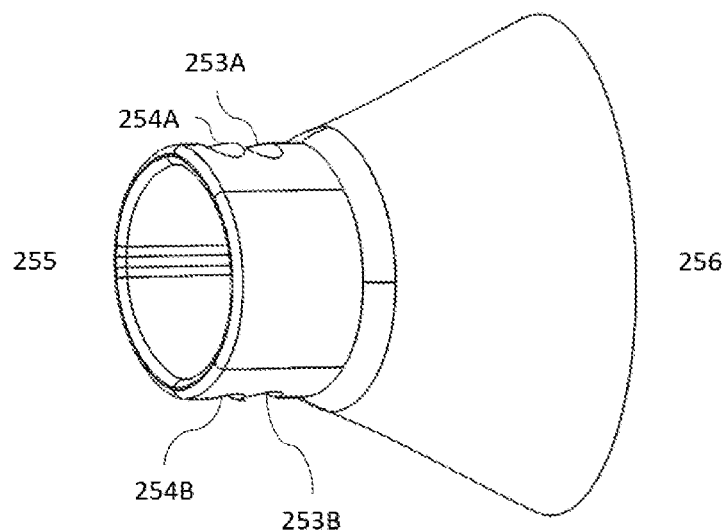
FIGS. 2D and 2E are schematic diagrams of mouthpieces for fluid delivery devices, according to various embodiments of the invention.
Figure 2E:
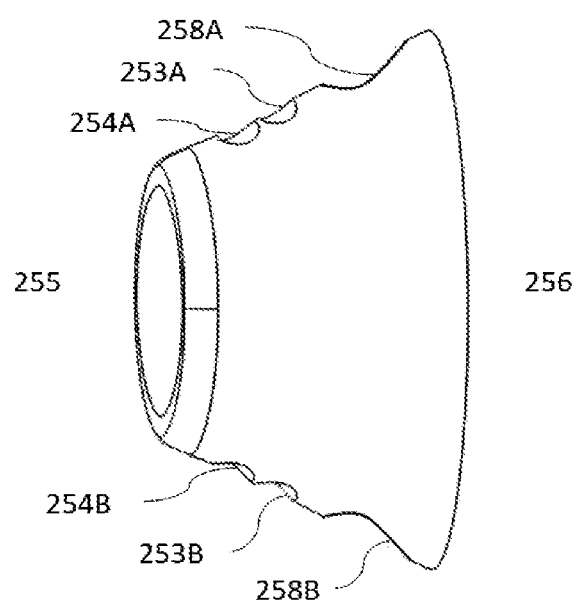

FIGS. 2D and 2E are schematic diagrams of mouthpieces 250 and 252, respectively, for fluid delivery devices, according to various embodiments of the invention.

FIG. 2D shows a mouthpiece 250 that can be coupled to a fluid delivery device (e.g., fluid delivery device 200 as shown above in FIG. 2A). The mouthpiece 250 includes four grooves for teeth 253A, 253B, 254A, and 254B, a portion that connects to the fluid delivery device 256, and a portion that is inserted into an individual's mouth 255. The four grooves produce two teeth positions for the individual. During use, an individual inserts the mouthpiece 250 into their mouth and positions their top teeth on either of grooves 253A or 254A and/or bottom teeth either on grooves 253B and 254B. In this manner, the individuals position relative to the wave generator and sensor(s) can be selectable and repeatable. In some embodiments the triggering event, which causes commencement of authentication process, is the return of an individual to their predefined position, as determined for example via a sensor (e.g., for humidity, conductivity and/or pressure) embedded in one or more of the grooves.

FIG. 2E shows a mouthpiece 252 that can be coupled to a fluid delivery device (e.g., fluid delivery device 200 as shown above in FIG. 2A). The mouthpiece 252 includes the four grooves for teeth 253A, 253B, 254A, and 254B, the portion that connects to the fluid delivery device 256, the portion that is inserted into an individual's mouth 255 and two lip grooves 258A and 258B. During use, individuals can insert the mouthpiece 250 into their mouths and positions their top and bottom lips on grooves 258A and 258B, respectively. Optionally, they may also position their top teeth on either of grooves 253A or 254A and/or bottom teeth either on grooves 253B and 254B. In this manner, the individuals position relative to the wave generator and sensor(s) can be selectable and repeatable. In some embodiments the triggering event, which causes commencement of authentication process, is the return of an individual to their predefined position, as determined for example via a sensor (e.g., for humidity, conductivity and/or pressure) embedded in one or more of the grooves.

Figure 3A:
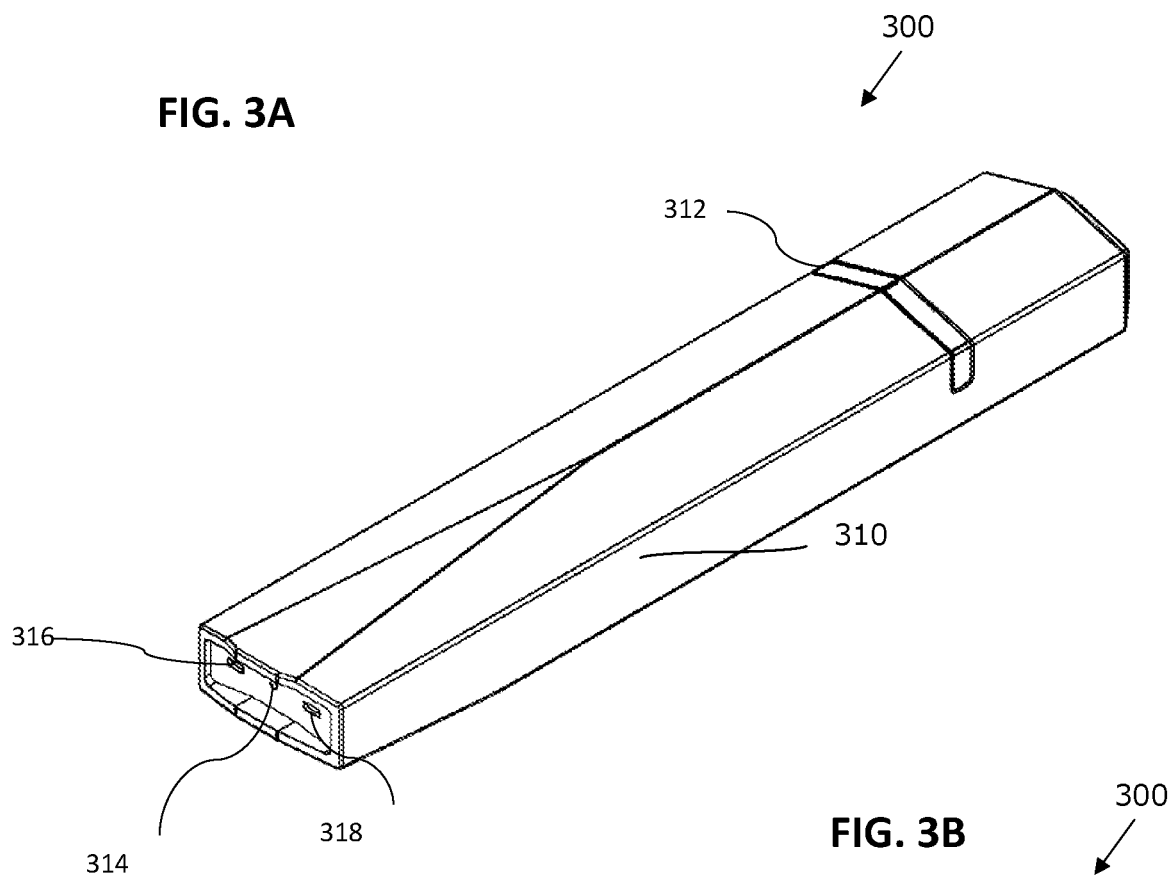
FIG. 3A and FIG. 3B are schematic diagrams of a fluid delivery device according to some embodiments of the invention.
Figure 3B:
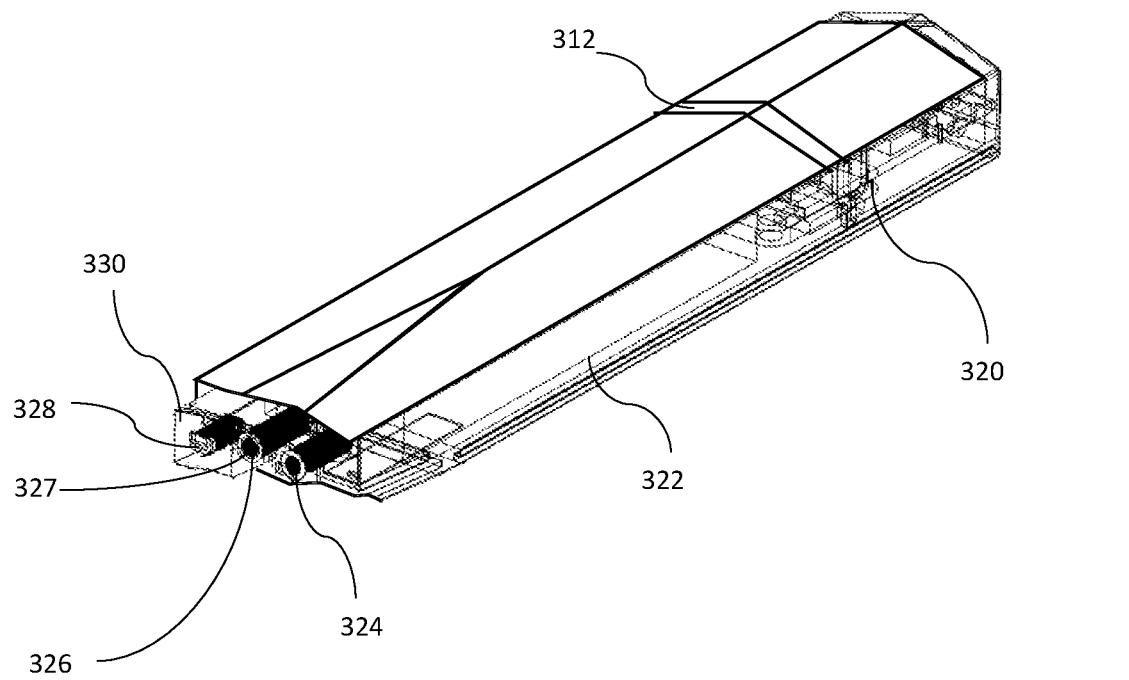

FIG. 3A and FIG. 3B are schematic diagrams of a fluid delivery device 300 (e.g., fluid delivery device 10 as described above in FIG. 1A) according to some embodiments of the invention.

The fluid delivery device 300 includes a housing 310. The housing 310 includes a LED light 312, an airflow aperture 314, a wave sensor entrance 316 and a wave generator exit 318. During operation, waves exit the wave generator exit 318, the wave sensor entrance 316 can detect reflection waves, and the airflow aperture 314 can permit a fluid to flow out of the device.

FIG. 3B shows some of the elements housed within the housing 310 of the fluid delivery device 300. Electronics and control panel 320, a power unit 322, a wave sensor enclosure 324, an airflow conduit 326, a wave generator enclosure 328, a flexible seal 330 are shown positioned within the housing 310. Flexible seal 330 can be made of a flexible material, such as silicon rubber, rubber of other kind, or flexible polymer material. In some embodiments the flexible seal is being in direct contact with the wave generator without having an enclosure therebetween. In some embodiments wave generator enclosure is made of a flexible material, such as silicon rubber or rubber of other kind or flexible polymer material. In some embodiments the wave generator is exposed to the sampled space (e.g., the mouth) via conduit. In some embodiments wave generator is a sound generator, e.g., a speaker, or buzzer and wave sensor is sound wave sensor, e.g., a microphone. In some embodiments, the sound wave sensor can comprise a noise dumper, in order to reduce the recorded background noise and increase the portion of recorded data typical to the individual. In some embodiments, the sound wave sensor is contact microphone, such as a piezoceramic microphone, which can be less sensitive to air vibrations than an air microphone. Each of the wave sensor enclosure 324 and wave generator enclosure 328 can have an open end in the direction of the individual's mouth. The shape of each of enclosures 324, 328 may be tubular, have a conical tube shape, or otherwise cylindrical or irregular. Each of the enclosures 324, 328 can be hollow and have substantially the wave generator or the wave sensor completely enclosed therein. In some embodiments, each of the enclosures 324, 328 may contain a medium, within which the wave generator and/or the wave sensor are disposed.

The wave sensor enclosure 324 houses a wave sensor and has an end that terminates at or near the wave sensor entrance 316. The airflow conduit 326 connected to an interior portion of the fluid delivery device 300 associated with a reservoir (e.g., the reservoir 18 as described above in FIG. 1A) that supplies a substance (e.g. a powder, a vapor and/or an aerosol) to the fluid (e.g. to the air flowing through the device). The fluid carrying the substance is delivered to the user through an opening 327 of airflow conduit 326. The wave generator enclosure 328 houses a wave generator (e.g., generator 24 as described above in FIG. 1A) and terminates at wave generator cover 330 (e.g., a flexible seal). The flexible seal 330 can cover the wave sensor positioned within the wave generator enclosure 328 to prevent or reduce acoustic interruptions (e.g., noise) caused by friction. In some embodiments, the flexible seal 330 is not present. In some embodiments, the wave generator enclosure 328 and thus the wave sensor is positioned at a distance away from the wave sensor entrance 316 to, for example, prevent or minimize noise. The distance can be determined based on noise level, sensor sensitivity and wave generator power.

In various embodiments, the fluid delivery device 300 includes a plurality of wave generators and/or a plurality of wave sensors. The plurality of wave generators can include or be an array of wave generators. The plurality of wave sensors can include or be an array of wave sensors. In various embodiments, some of the plurality of wave generators or all of the plurality of wave generators are enclosed. In various embodiments, the plurality of wave generators that are enclosed are in a single enclosure or multiple enclosures. In various embodiments, some of the plurality of wave sensors or all of the plurality of wave sensors are enclosed. In various embodiments, the plurality of wave sensors that are enclosed are in a single enclosure or multiple enclosures.

In some embodiments, each enclosure has the same media or different media. In some embodiments, the enclosures have a medium of air.

During operation, in some embodiments, with a plurality of wave generators, the plurality wave generators can be used simultaneous, sequentially or any combination thereof. In some embodiments, the plurality of wave generators transmit the same waves, different waves, or any combination thereof. In some embodiments, the plurality of wave sensors receive the same waves, different waves, or any combination thereof.

Turning to FIG. 3C and FIG. 3D, FIG. 3C are graphs showing an example of a received wave without a cover on the wave sensor and FIG. 3D are graphs shown an example of the same received waves with a cover on the wave sensor. As can be seen, the received waves in FIG. 3C have noise that is not present in the received waves in FIG. 3D.

The electronics and control panel 320 can include any of the elements as described above in FIG. 1A.

Figure 4A:
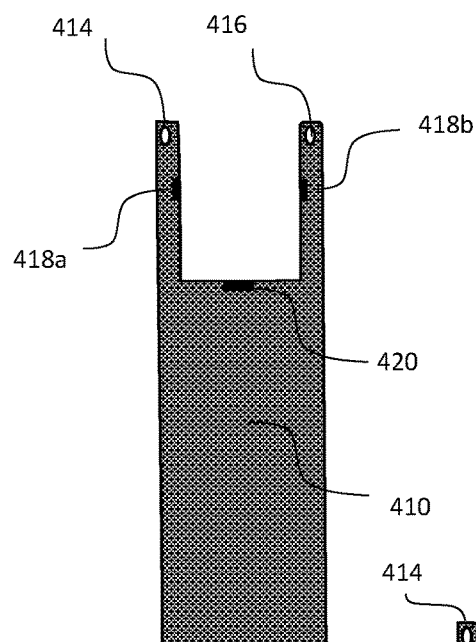
FIG. 4A, FIG. 4B and FIG. 4C are schematic diagrams of a fluid delivery device according to some embodiments of the invention.
Figure 4B:
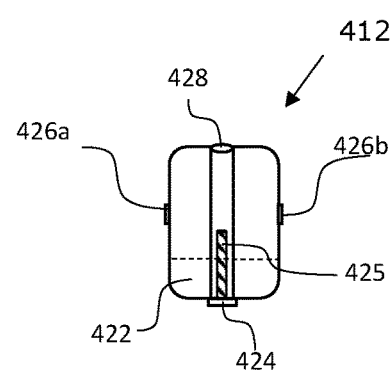
Figure 4C:
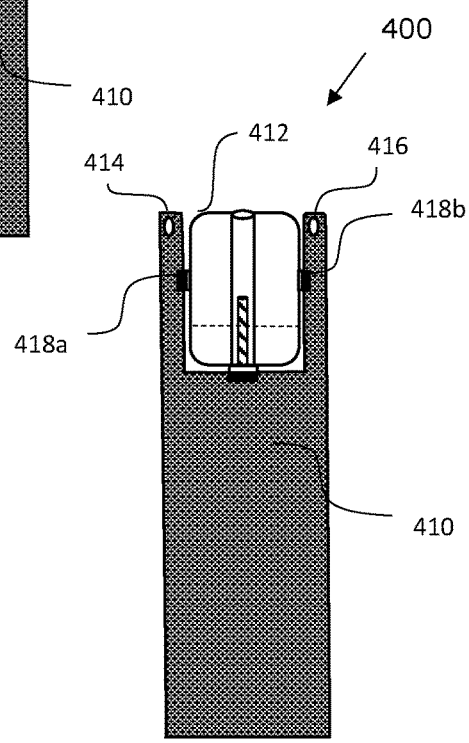

FIG. 4A, FIG. 4B and FIG. 4C are schematic diagrams of a fluid delivery device 400 (e.g., fluid delivery device 10 as described above in FIG. 1A) according to some embodiments of the invention. The fluid delivery device 400 includes a housing 410 and a mouthpiece 412. The housing includes a wave generator exit 414, a wave sensor entrance 416, two connectors 418a and 418b, an electrical connector 420. The mouthpiece 412 includes a substance repository 422, an electric connector 424, a wick 425, two connectors 426a and 426b, and an airflow conduit 428.

The mouthpiece 412 can be inserted and removed from the housing 410. When the mouthpiece 412 is inserted into the housing 410, the two connectors 426a and 426b connect with the two connectors 418a and 418b respectively, the electrical connector 420 connects with the electrical connector 424.

Figure 4D:
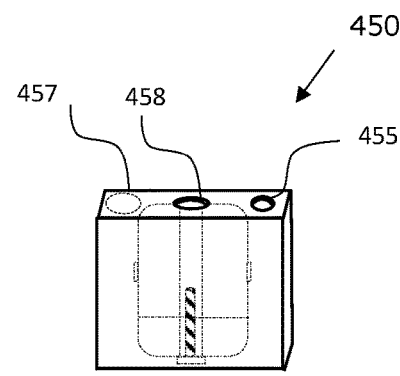
FIG. 4D is an example of a mouthpiece for a fluid delivery device, according to some embodiments of the invention.

Turning to FIG. 4D, FIG. 4D is an example a mouthpiece 450 for a fluid delivery device, according to some embodiments of the invention. The mouthpiece 450 for a fluid delivery device in FIG. 4D is similar to FIG. 4C, except that the mouthpiece 450 includes a wave generator exit 455 and wave sensor entrance 457 are within one housing, and the housing also includes an airflow conduit 458. The connection of the mouthpiece 450 to the fluid delivery device can be electrical. In some embodiments, the connection of the mouthpiece 450 is a USB connection or any connection as is known in the art. In some embodiments, the fluid delivery device can provide power to the mouthpiece 450.

In some embodiments, wave sensor and/or wave generator are incorporated in fluid delivery device 410. In some embodiments, wave sensor 24 and/or wave generator 22 are incorporated in mouthpiece 450 of fluid delivery device 410. In some embodiments, the wave sensor and/or wave generator are incorporated in a probe (not shown), operative to be coupled to the fluid delivery device 410. In some embodiments, the probe includes any of the wave sensor, the wave generator, and any of the components of authentication unit, such as described in FIG. 1B, element 12. In some embodiments, the probe includes, or have access to registration data of an individual, and is operative to serve as an identification object. Optionally, the identification object may be coupled to one or more devices in order to perform authentication and receive access to the fluid delivery device 410 and/or to other devices.

Figure 4E:
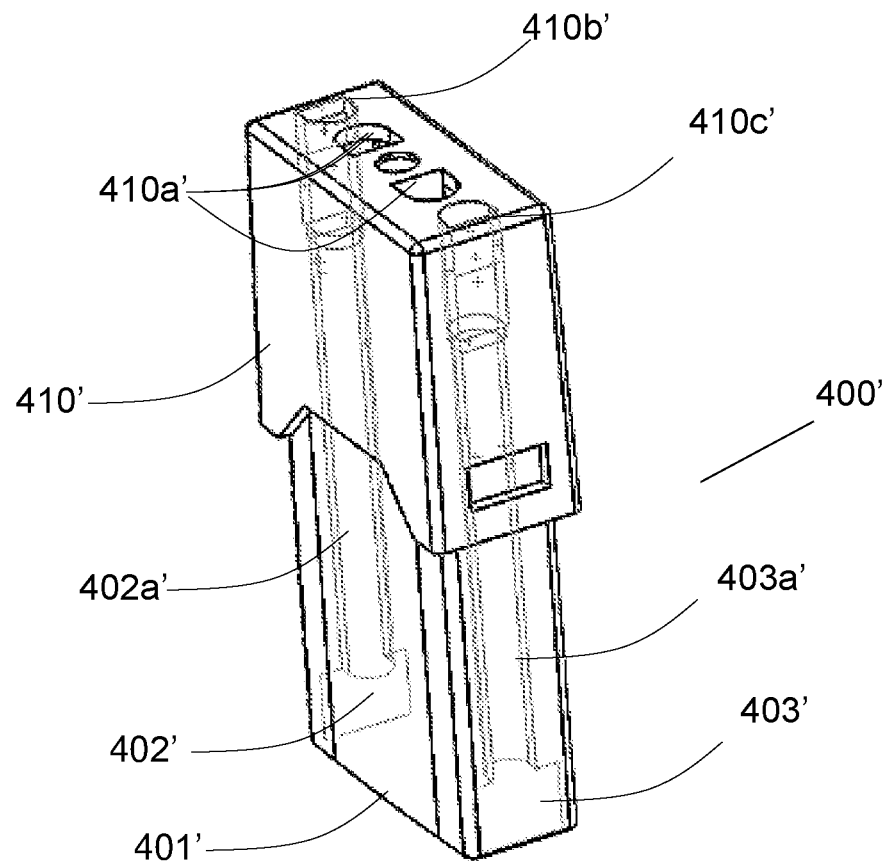
FIG. 4E and FIG. 4F are, respectively, schematic diagrams of a perspective view (FIG. 4E) and a top view (FIG. 4F) of a fluid delivery device (e-cigarette) having a mouthpiece, according to some embodiments of the invention.

FIG. 4E is a schematic diagram of an isometric view of a mouthpiece 410' (possibly replaceable) for coupling to a fluid delivery device, e-cigarette, being a variation of the mouthpiece 450 of FIG. 4D. In some embodiments, a reservoir or a reservoir region is present within mouthpiece 400', essentially as depicted in FIG. 4D.

Figure 4F:
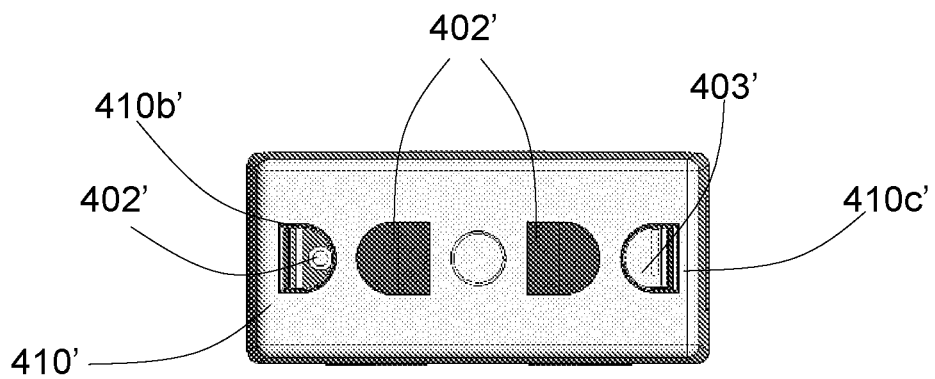

FIG. 4F is a schematic diagram of a top view of a fluid delivery device, e-cigarette 400', having a mouthpiece 410' coupled thereon, according to some embodiments of the invention.

The e-cigarette 400' includes a housing 401'. The housing 401' includes a wave generator tube 402a', a wave generator 402', a wave sensor tube 403a' and a wave sensor 403'. The mouthpiece 410' can include one or more substance delivery apertures 410a' through which a substance can be delivered into user's oral cavity. The mouthpiece 410' can include a wave generator tube exit 410b' in fluid communication with wave generator tube 402a' and wave generator 402 and a wave sensor tube entrance 410c' in fluid communication with wave sensor tube 403a' and wave sensor 403'. In some embodiments, wave generator 402' and wave sensor 403' can be observed through wave generator tube exit 410b' and wave sensor entrance 410c', respectively.

In some embodiments, a device for obtaining an oral signature of an individual, includes a mouthpiece for positioning at least a portion of the device within a mouth of the individual. The mouthpiece may have a wave exit for allowing transmission of waves into the mouth of an individual. In some embodiments, the mouthpiece or device includes a wave generator connected to the housing of the device or mouthpiece and positioned relative to a wave exit in the mouthpiece to cause waves generated by the wave generator to transmit through the wave exit during operation. In some embodiments, the mouthpiece is provided with a connector for connecting to a wave generator that is included in the device to which the mouthpiece is attached. In some embodiments, the mouthpiece, and possibly the device to which it is attached, includes at least one waveguide (for example a sound guide) for guiding waves from the wave generator to the wave exit. Accordingly, wave generators may be placed in any location within the device and/or mouthpiece as long as a waveguide is positioned to guide waves the sound exit for transmitting by the device.

The position of the wave exit in relative to the structure of the mouthpiece is such that positioning the at least a portion of the mouthpiece within at least a portion of a mouth of the individual causes the wave exit to be at a predetermined position with respect to the mouth of the individual.

FIG. 5A is a simplified block diagram of an authentication process 100, which occur in some embodiments of an individual authentication system, for example, for a personal device. In accordance with these embodiments, authentication process 100 comprises an optional registration module 101 and a testing module 102. Personal device may include any one of a personal device, and/or a substance delivery device (e.g. an inhaler, an e-cigarette, a liquid dispenser, a spray dispenser, or the like. A personal device may be configured to deliver a non-controlled or controlled substance, including one or more of a medication, a drug, cannabis, nicotine, and/or tobacco.

In registration module 101, classification rules are defined according to data obtained. At 110 a wave is transmitted towards the mouth of an individual and the reflection of the wave is captured. Optionally wave is transmitted into the oral cavity of the individual. Optionally, wave 110 is transmitted in following or in response to a triggering event. The triggering event may comprise one or more stages in operation of a device. For example, beginning of inhalation (in an inhaler device), motion sensing, reaching a predefined operation status within a device (for example constant airflow, air pressure falling below a given threshold, the commencement of heating, reaching a predefined temperature) and/or a period of time passing after a predefined triggering event. Optionally, triggering is performed manually by the individual or another operator.

Optionally, 110 includes positioning a mouthpiece of an inhaler device is in the mouth of the individual. The mouthpiece may include a wave generator and/or a wave sensor, with which the wave is transmitted, and a reflection is captured. Optionally, either of wave generator and/or a wave sensor are located in a part in the inhaler other than the mouthpiece. Optionally, a single component can generate and capture waves, or comprise both the wave generator and the wave sensor.

Optionally, a soundwave generator is programmed by a frequency generator to send a repetitive sound wave with predefined amplitude, frequency, duration and offset parameters. Optionally, similar sound wave can be generated by a digital component controlled by a microcontroller unit. Optionally, in order to expand the authentication data, wave is transmitted and/or captured in a plurality of locations and angles inside the mouth of the individual. Optionally, captured reflections may be converted to electric voltage analog signals. The electric voltage analog signals may be captured and saved by an oscilloscope. Optionally, captured reflections may be converted to digital data signals and captured by microcontroller unit.

At 120 captured reflections, or selected portions thereof, are analyzed by the authentication system. Classification rules for the wave data samples captured in 110 may be generated. In some embodiments, analysis is based on a binary classification method. For example, an authentication system may be trained to activate a substance delivery device (for example an inhaler device) upon detecting a specific authorized individual. In other embodiments, such analysis is done by a multi-class classification method wherein the authentication system is trained to activate the substance delivery device at a determined pattern or mode for each authenticated individual.

At 130, the received authentication data and/or the analysis product(s) thereof are stored in the authentication system database. The stored data define the classification rules of the system. This oral signature may now be associated with the individual. Additionally or alternatively data may now be associated with an authorization indication. The data may be stored locally, for example in a system or device now associated with the individual. Additionally or alternatively, the data may be stored in a remote location or in a cloud server, and be used for one or more devices, possibly being different than the device used for registration 101. Additionally or alternatively, the data may be stored in a personal identification object, such as RFID tag or biometric ID card. The identification object may be coupled to one or more devices during authorization. Additionally or alternatively, the identifying object may be coupled to a new device, i.e., a device which was never registered to the individual. Once coupled to the new device, the individual may upload the data saved in the identifying object and to and save it in the memory of the new device as a local registration data.

In some embodiments, registration may be performed without being followed by later testing. Transmitting waves towards at least a portion of a mouth of an individual and sensing by a device at least a portion of reflections of the waves from the individual may be followed by deriving an oral signature based on the sensing and storing an indication of the oral signature in a database for any use that may or may not be performed after registration is completed. For example, a person may become registered to a database and/or a device and the save oral signature may be later transferred for use by a different device and/or system and/or be transferred to an additional database. Storing an oral signature may include, for example, storing data indicative of the received reflections of waves or an analysis result thereof.

In testing module 102, authentication is performed by the system based on stored authentication data and the classification rules. At 140, a sample wave is transmitted towards the mouth of the individual by a wave generator and the reflection of the sample wave is captured by a wave sensor, essentially as described in 110. Optionally wave is transmitted into the oral cavity of the individual. Optionally, transmitting waves towards the individual's mouth does not generally include transmitting waves towards the individual's ear canal. Optionally, capturing the reflections does not generally include receiving waves reflected from the individual's ear canal. Optionally, transmitting waves towards the individual's mouth is not done by using the individual's voice.

At 150, the sample reflection is analyzed by the authentication system. Data obtained in 140 is associated with an individual and/or with a property of an individual. At 160, the authentication system accesses stored authentication data.

At 170, the system compares sample wave data to the classification database and determines whether or not the captured reflections match the authentication data. Optionally, if the analysis is based on a multi-class classification method, the system additionally determines the identity of a specific individual. Optionally, the analysis is based on a binary classification method, and the system determines whether or not the individual matches the stored data. Optionally any of 150, 160 and 170 may be performed locally in a single device (e.g. a personal device), or in one or more distinct devices being in communication therewith.

At 180, in embodiments where authentication system is associated to an inhaler device or other substance delivery device, substance is delivered to an authenticated individual. In various embodiments, once authentication is successful in 170, the system updates the authentication data of the individual in 181. Such updating may be performed occasionally, periodically or at every successful authentication. Optionally, 181 is performed based on a degree of similarity between the analysis of 150 and stored authentication data.

Optionally, wave transmission, capturing and analysis are repeated, for example in order to improve the performance of the system. Specifically, 140, 150 and 160 may be repeated more than once, in order to decrease a likelihood of a false determination in 170.

In some embodiments of authentication process, none of the items described shall include using the individual's inhalation pattern as authentication data.

In some embodiments of authentication process, none of the items described shall include using electrical resistance properties of the individual's bones and/or the tissues as authentication data.

Figure 5B:
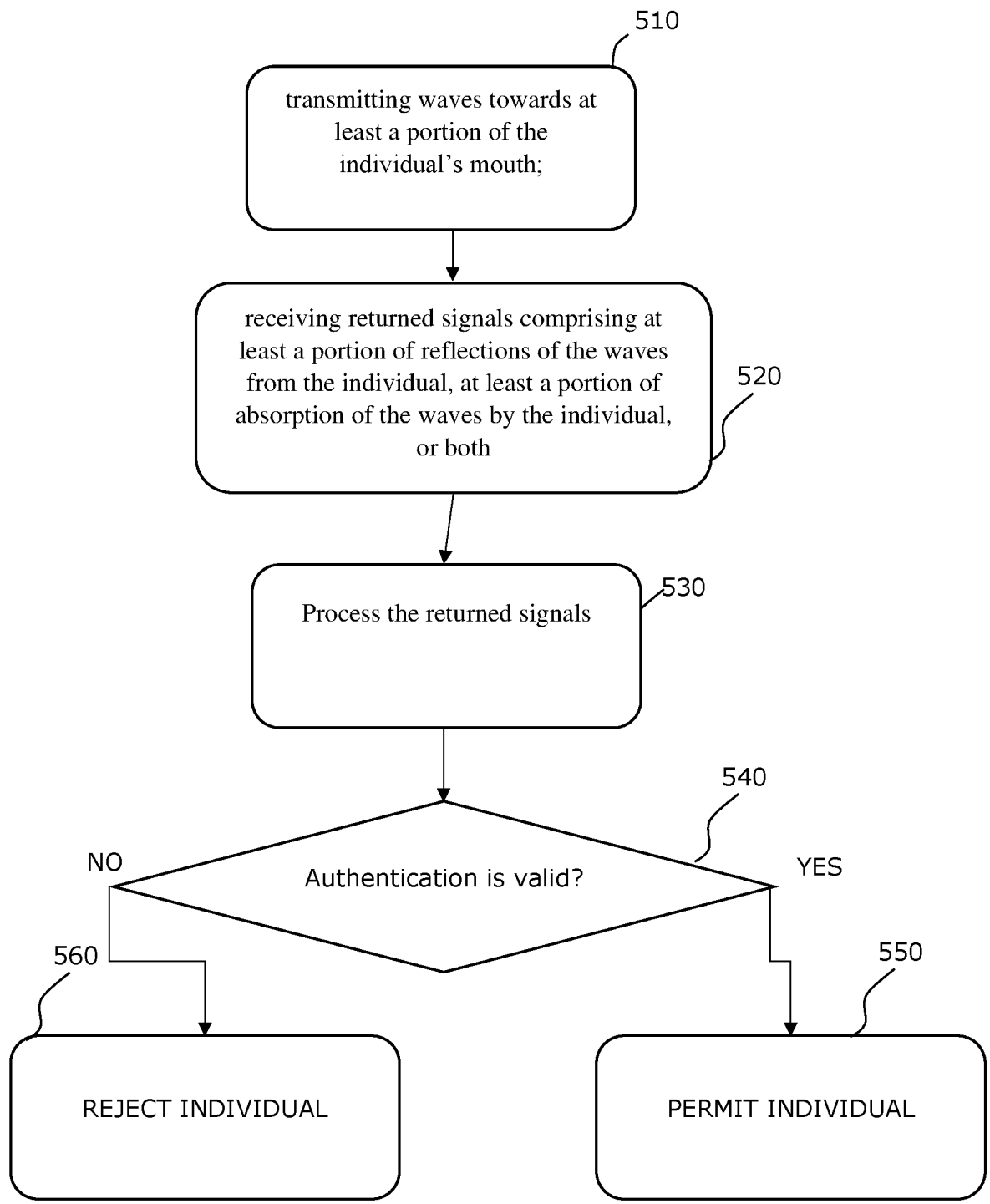
FIG. 5B is a flow chart of a method for authenticating an individual for delivery of a substance to the individual, according to some embodiments of the invention.

FIG. 5B is a flow chart of a method for authenticating an individual for delivery of a substance to the individual, according to some embodiments of the invention. The method involves transmitting waves (e.g., generated via wave generator 22 as described above in FIG. 1A) towards at least a portion of the individual's mouth (510).

The method also involves receiving reflected waves (e.g., via sensor 24 as described above in FIG. 1A) that include at least a portion of reflections of the waves from the individual, or both (520). For example, transmitting (510) may be continuous, with receiving (520) being performed intermittently for only a portion of the received waves. In some such embodiments, transmitting may include repeated transmission of the same wave pattern a plurality of times, and optionally, receiving is timed to occur at the same time in each repetition.

The method also involves processing the reflected waves (530). In some embodiments all of the waves received in 520 are used in the processing. In some embodiments only a portion of the waves received in 520 are used in the processing. For example, transmitting (510) and receiving (520) may be continuous, with processing (53) being performed intermittently for only a portion of the received waves. In some such embodiments, transmitting may include repeated transmission of the same wave pattern a plurality of times, and optionally, processing is performed only for waves that were received at the same time in each repetition.

Processing the reflected waves can involve determining a signature of the individual and/or personal data associated with the individual (e.g., identification of nasal or tympanic cavity). In some embodiments, the processed waves can be analyzed by comparison against stored signatures of individuals who were previously registered and/or or registered as authorized to receive the substance (e.g., registered at a pharmacy database after a physician transmits a prescription to the pharmacy and/or age of date of birth previously verified, identification information stored in a database of individual).

In some embodiments, the reflected waves are analyzed to determine if the individual is a child or adult. For example, the child may be an individual below 10, 12, 14, 16, 18 or 21. The adult may be, for example, an individual above 16, 18, 21, 25, 30. In these embodiments, an erroneous determination can be made, namely that an adult is identified by the system as a child (or not identified as an adult) or vice versa—a child is identified as an adult (or is not identified as a child). In such cases, if misidentification prevents use by an individual that should have been authorized (e.g., an adult prevented from smoking tobacco as he is not identified as being an adult) the individual may revert to alternative methods of identification. For example, the individual may be registered on his device in such conditions that allow overriding the child/adult identification, for example, at a point of sale by showing valid identification documentation and proof of age. In such cases the seller can have the authority and/or tools (software, hardware, and/or password) required to enable registration of any individual. In some embodiments, the individual's age and/or authorization and his oral signature are recorded on a mobile device (e.g., a token) that can be used for registration on devices as an override of child/adult identification, for example by way of wireless transfer of information (e.g., Bluetooth, WiFi and/or RFID, etc.) between the mobile device and a controller associated with the device or purpose for which age identification is required. Storing these data and/or the communication can be encrypted to prevent ease of unauthorized override of the age identification.

The wave signature may be obtained in advance in a registration process, in which the authorized individual uses an authentication module (such as authentication module 12 of FIG. 1B) and data indicative of the wave reflection is saved as a signature for future comparison with obtained wave reflections during use of a device associated with the stored data or having access to the data. During the registration, the wave signature of the individual may be associated with an authorization indication and/or with an identity of the authorized individual, and recorded in a memory. In some embodiments, a security token is required during the registration process. In some embodiments, the registration process only occurs once. In various embodiments, the reflected waves can be influenced by one or more features of the current individual's parts of the mouth (e.g., oral cavity, larynx, pharynx, vocal cords, throat, tongue and/or other part of the oral cavity, as well as instantaneous conditions, such as, for example, having something in the mouth, such as a chewing gum, food leftover, retainer, throat lozenge and/or candy). The reflected waves can be influenced by the position of the tongue, or the position and orientation of the fluid delivery device, and in particular the wave generator and/or the wave sensor, the current individual's current activity (e.g. inhalation, exhalation, physical activity, rest, etc.). When used during inhalation, acquired reflections can be associated with specific points of time during the inhalation, which can correlate with changes within the oral cavity that normally occur during use of an inhalation device, and the analysis can take such timing into account. When used during exhalation, acquired reflections can be associated with specific points of time during the exhalation, which can correlate with changes within the oral cavity that normally occur during exhalation, and the analysis can take such timing into account.

In some embodiments, the reflected waves are normalized with respect to a predetermined reference wave signal of the sound of the environment. In some embodiments, noise is filtered (or substantially filtered), canceled (or substantially cancelled) or any combination thereof from the reflected waves. In some embodiments, the noise is environmental noise. In some embodiments, the portions of the received waves that are below a predefined threshold are filtered out. In some embodiments, the predefined threshold is between −6 and −14 Decibels. In some embodiments, the predefined threshold is between −7 and −12 Decibels and even between −9 and −12. In some embodiments, the predefined threshold is between −6 and −8 Decibels.

In some embodiments, the reference wave signal is measured at a factory (and used thereafter as described above). In some embodiments, the reference wave signal is measured by the individual on occasion (e.g., when turning the fluid delivery device on) before use, outside individual's mouth and/or in individual's mouth.

In some embodiments, the reference wave signal is measured in real time during use of the fluid delivery device. For example, two wave sensors (e.g. microphones) may be used to sense the reflections and then the difference between the sensed reflections caused by their different physical locations are sufficient to clean the noise. In some embodiments, the reference wave signal is measured in real time with a wave pattern that is not defined in advance (e.g. white noise, airflow sound, etc.) by having two wave sensors (e.g. microphones). In some embodiments, the reference wave signal is predefined and the information regarding the transmission is used in cleaning the reflection data. In some embodiments, one wave sensor is configured to receive the transmission and another wave sensor is configured to receive the reflections (e.g., when the waves are electromagnetic waves).

The method also involves determining if the individual is an authorized individual (540). In some embodiments the individual is determined to be an authorized based on the processed reflected waves. In some embodiments, additional identification data is used along with the received waves to determine if the individual is an authorized individual. For example, fingerprints, inhalation pattern, voice, retinal scan, breathing pattern, face recognition, and/or any biometric data. The biometric data can include gender, ethnicity, geographical origin, or any combination thereof. In some embodiments, the additional identification information includes historical use of the individual, a password and/or response to one or more security questions. In some embodiments, a likely age of the individual is determined based on the received waves to determine if the individual is authorized. For example, it can be desirable to restrict access of the fluid delivery device to individuals above an age threshold. The determination can, for example, include determining that the individual is above a first threshold and/or that the individual is not below a second threshold. In some embodiments the first threshold and the second threshold are the same. In some embodiments, machine learning algorithms are used for authentication. In some embodiments, machine learning sorting algorithms are used for age determination.

If the individual is authorized, the authentication is successful (e.g., valid) and the individual can be delivered the substance (560). If the individual is not authorized, the authentication is unsuccessful (e.g., invalid) and the individual is not delivered the substance (570).

In some embodiments, if the authentication is invalid the fluid delivery device 10 locks for a period of time and/or until the device is unlocked (for example, at a point of sale). For example, a plurality of failed authentications (e.g., 3 or more or 5 or more) causes the device to lock down for a period of time. In some embodiments, a plurality of failed authentications (e.g., 3 or more or 5 or more) causes the device to lock down for a period of time only if they take place within a predefined period of time (e.g. within a 1 minute or within 30 seconds).

Locking the device can involve turning off the power supply, closing the air flow valve, disconnect the heating electrical circuit, and/or closing a barrier (e.g. plug or valve) that arrests the mechanism of dose units supply into the delivery tract.

In various embodiments, denying supply can involve refraining from turning the power supply on, refraining from opening the air flow valve, refraining from switching the heating electrical circuit into a closed circuit, and/or opening a barrier (e.g. plug or valve) that allows the mechanism of dose units supply into the delivery tract.

In some embodiments, once an individual is authorized, an age sorter can confirm an age of the individual. In some embodiments, confirming the age is limited to confirming that the individual is above a first age threshold and/or not below a second age threshold, with the second age threshold being optionally lower than the first.

For example, turning to FIG. 5C which is a flow chart of a method for authenticating an individual for delivery of a substance to the individual, according to some embodiments of the invention. As shown in FIG. 5C, 510 through 540 and 560 are the same as FIG. 5B, however, 550 in FIG. 5B is replaced with 570 and 580 as shown in FIG. 5C. In these embodiments, if the authentication is valid, then the method involves determining if the individual complies with an age limitation based on the analysis of the reflected waves (570). The age limitation can be input by a user, set by a pharmacist, set by a manufacturer, determined based on a type of the device that is used or otherwise set.

If the individual doesn't comply with the age limitation, then the method involves rejecting the individual (560). If the individual does comply with the age limitation, then the method involves permitting the individual (580). Each of the authentication of this method may occur more than once during a usage event, for example in order to increase the protection and/or prevent passing the device subsequent to authentication to a non-authorized user.

In some embodiments, the method shown in FIG. 5C provides an additional layer of protection, against age related abuse of the device. Accordingly, even if a false identity authorization is issued, the individual is checked again for their age, and an individual who does not meet the age limitation is rejected or stopped.

In some embodiments of an authentication method, a wave reflection data sampled from the mouth of an individual is analyzed compared to a database comprising data of restricted individuals. The individual can be permitted only if they were found non-restricted.

In some embodiments, determining if the individual is a restricted individual is done subsequent to authenticating their identity. In some embodiments the determination whether an individual is restricted can be additional to the identity authentication. Once an individual is authorized, the system analyses their wave reflection data compared to the restricted individuals' database. If the individual was found non-restricted, they are being permitted.

In some embodiments the determination whether an individual is restricted can be alternative to the identity authentication. In some embodiments, the system may determine that the identity of an individual is not authenticated. An alternative permission path may be checking whether or not this individual is restricted, and if they were found not restricted, the individual is permitted.

In some embodiments, an authorized individual of age (570) may have blocked such that only the method of FIG. 5B is used to authenticate the user's identity. A potential advantage of doing so is that less energy is used by the fluid delivery device for authentication. Another potential advantage is for individuals who are of age but are misidentified by the age sorter and for young individuals who the age sorter should reject. In both such cases, age confirmation may be undesired.

Figure 5D:
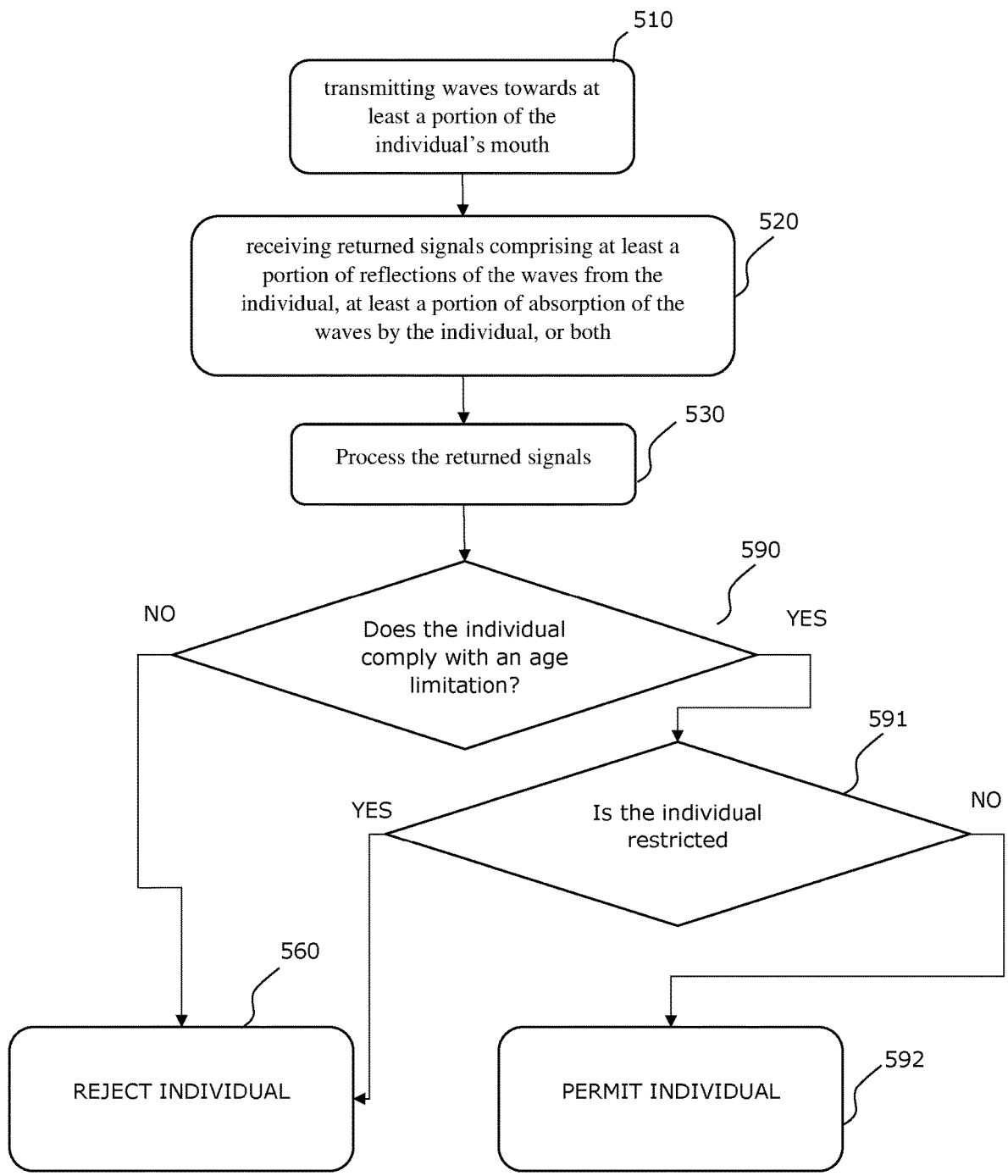
FIG. 5D is a flow chart of a method for authenticating an individual for delivery of a substance to the individual, according to some embodiments of the invention.

In some embodiments the determination whether an individual is restricted can be additional to age identification and/or to individual authorization. For example, in FIG. 5D, instead of authorizing a registered individual, the age of an individual is checked and if the individual passes the age check (or authorization check), whether or not the individual is on a restricted list is also checked. For example, turning to FIG. 5D, FIG. 5D is a flow chart of a method for authenticating an individual for delivery of a substance to the individual, according to some embodiments of the invention. As shown in FIG. 5D, 510 through 530 are the same as FIG. 5B, however, 540 and 550 in FIG. 5B are replaced with 590, 591, and 592 as shown in FIG. 5D. In these embodiments, the method involves determining whether the individual complies with one or more age limitations based on analysis of the reflected waves (590). If the individual does not comply with the age limitation (or if he is not identified as an authorized user), then the individual is rejected (560).

If the individual does comply with the age limitation (or if he is identified as an authorized user), then the individual is also checked to determine if the individual is on a restricted access list (591). The restricted access list can be input/updated by a user, can be based on past fraudulent activity, can be input by a pharmacist, a manufacturer or a doctor or any combination thereof or otherwise.

If the individual is on the restricted access list, then the individual is rejected (560). If the individual is not on the restricted access list, then the individual is permitted (592).

In some embodiments, the method of FIG. 5D provides an additional layer of protection, abuse of the device. Accordingly, even if a false identity authorization or age confirmation is issued, the individual is checked again for not being listed as a restricted individual, and a restricted individual is rejected or stopped.

Optionally, a database of restricted and/or permitted users is created by collecting oral signatures of individuals and storing them in association with restriction and/or permission data, respectively. For example, a parent may have their child's oral signature stored on the parent's fluid delivery device as a restricted individual to ensure that the child will not be able to use the parent's device, even if the child is misidentified as an adult. In some embodiments, young adults may opt to register as being of age on a database so that in the event that their oral signatures will not be properly identified by age authentication, they will be identified as permitted individuals via the data base and their presence in the database will override an oral authentication of age. In some embodiments, a young adult may register as such by presenting proof of age at a point of sale.

In some embodiments a device, such as device 52 in FIG. 1A, includes a communication unit for retrieving data from a permitted and/or restricted individual database. In some embodiments, a database, or a part thereof (e.g. based on geographic relevance), is stored locally, in the device. In any method such as exemplified in FIGS. 5A, 5B and 5C, the database may be used to override any other form of authentication.

Figure 6A:
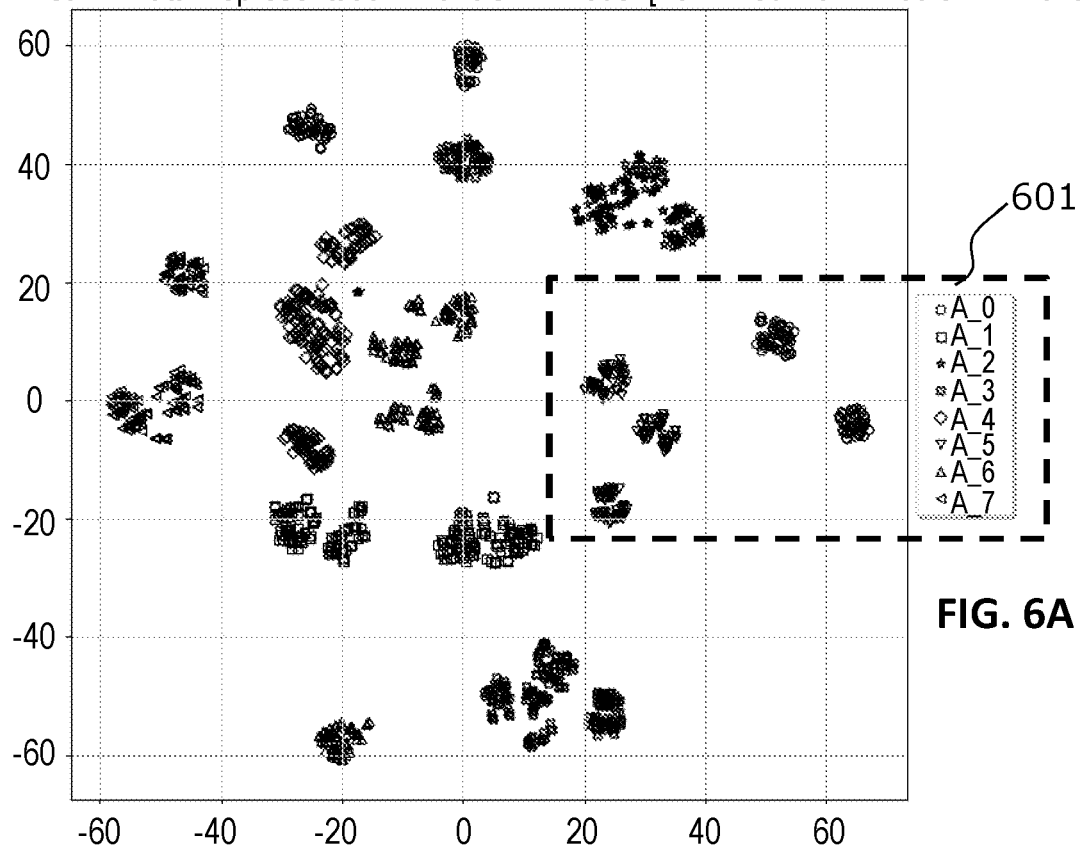
FIG. 6A is a T-distributed Stochastic Neighbor Embedding (t-SNE) graph visualizing a possible distinction between received waves from eight different individuals, according to some embodiments of an authentication system and method.

FIG. 6A is a T-distributed Stochastic Neighbor Embedding (t-SNE) graph visualizing a possible distinction between received waves from eight different individuals. The results were collected in an experiment that was conducted in order to test some embodiments of an authentication system.

Sound wave signal samples were taken from eight (8) different individuals. The individuals were told to insert a probe into their mouth and avoid movement. The probe included a wave generator and a wave sensor, which received the reflected waves. The wave generator was 46 Ohms Receiver, Balanced Armature Speaker 20 Hz ~8.8 kHz Top Round 105 dB. The wave sensor was I2S MEMS Microphone, Omnidirectional, −26 dB@94 dB SPL.

A chirp of 3200-9200 Hz Linear Frequency Modulated (LFM) sound waves was transmitted into the mouth of the individuals. The chirp included three wave samples, each of which lasted 50 milliseconds with breaks of 50 milliseconds each therebetween. the entire chirp was therefore 250 milliseconds. 20 chirps, hence 60 samples were taken from each of the eight individuals.

A processor recorded the received wave reflections and encoded the received weaves by Digital Signal Processing (DSP) algorithm and stored in a database. A reference chirp of 3200-9200 Hz LFM sound wave samples was transmitted to the surrounding and recorded adjacent to and at the same location of the sampling of the individuals. The chirp included three wave samples, each of which lasted 50 milliseconds with breaks of 50 milliseconds each therebetween. One of the three reference samples is shown in plots 6C and 6D, and represents the ambient sound.

During processing the data, samples were cleaned and normalized with respect to the reference wave. The data was entered to an artificial intelligence (AI) algorithm of the Random Tree kind. The system analyzed the data, compared between the samples and gave each sample a multi-dimensional value that reflects the sample's difference degree with respect to the other samples. The algorithm visualized its analysis using T-distributed Stochastic Neighbor Embedding (t-SNE) on the graph shown in FIG. 6A.

Figure 6B:
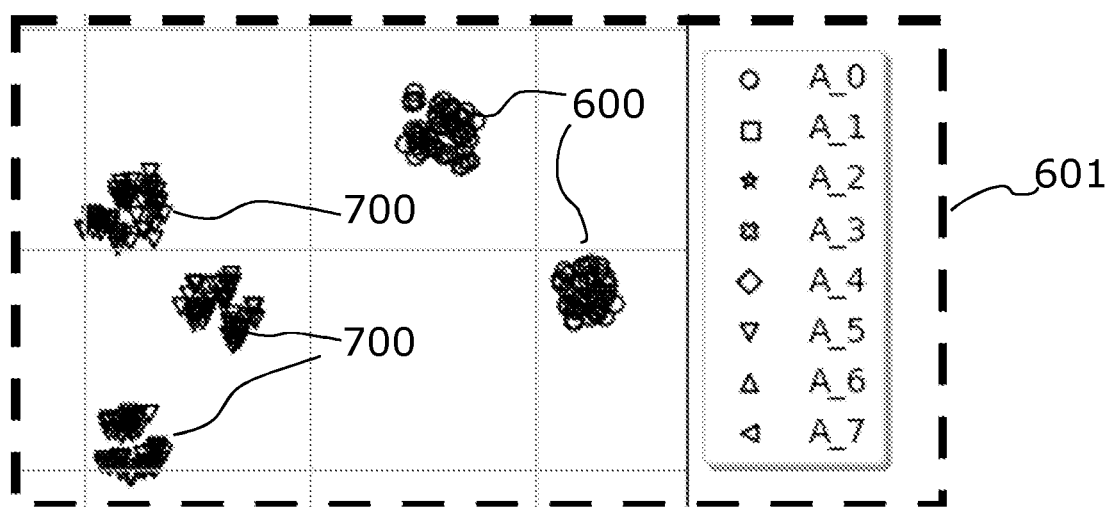
FIG. 6B is an enlarged portion of FIG. 6A depicting T-distributed Stochastic Neighbor Embedding (t-SNE) graph visualizing a possible distinction between received waves from two different individuals, according to some embodiments of an authentication system and method.

Each of the symbols shown on the graph of FIG. 6A represent a single sample. after receiving the result, each sample on the graph was given a symbol with respect to the individual to whom it belongs. For example, the circled symbols represent wave reflections that was received during transmission to the mouth of individual A_0, the square symbols represent wave reflections received from individual A_1, and so forth. As can be seen in FIG. 6A, the AI algorithm arranged the received waves in distinct clusters, each of which comprising samples of the same individual. The results show that the system can distinguish between individuals based on wave reflections received from their mouth. An enlarged portion of FIG. 6A, marked by dashed line 601 is depicted in FIG. 6B to show part of the results at higher resolution. As seen, two clusters 600 of circle symbols represent wave reflections taken from the mouth of individual A_0 and three clusters 700 of inverted triangles represent wave reflections that were taken from the mouth of individual A_5. This two-dimensional representation represents a portion of the data points that were analyzed by the system in this example and shows that different individuals manifest differently one from the other to a degree significantly greater than the variation between samples taken from the same individual.

Figure 7:
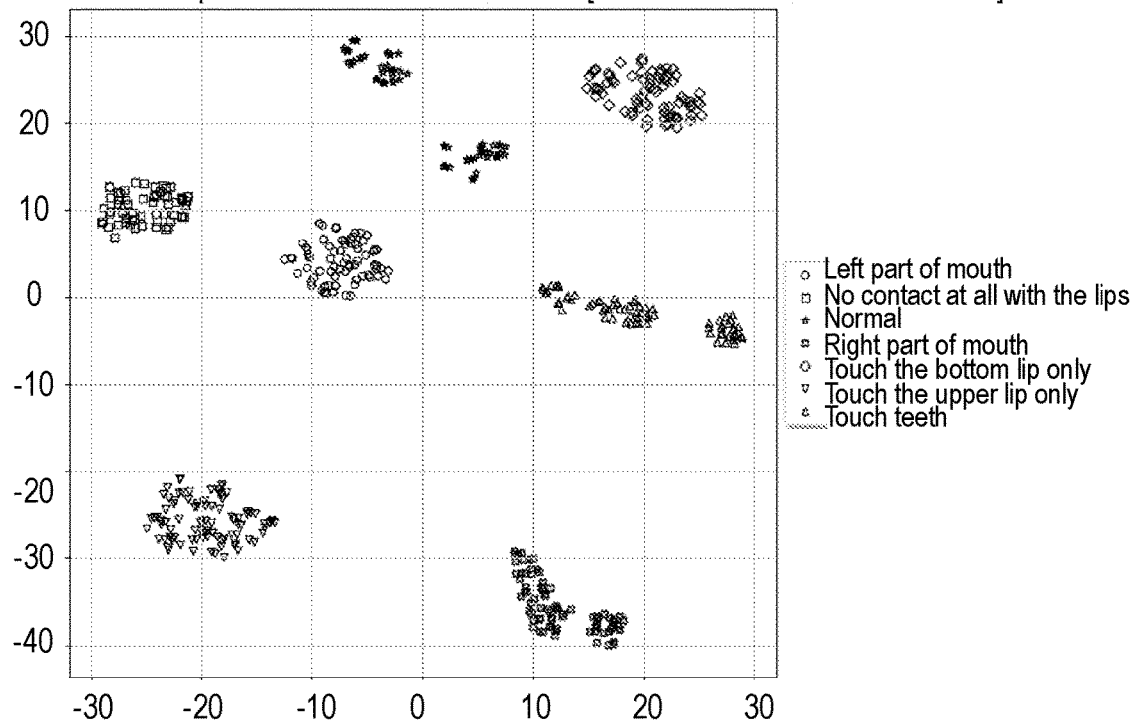
FIG. 7 is a T-distributed Stochastic Neighbor Embedding (t-SNE) graph visualizing a possible distinction between received waves from different positions of a mouth of an individual, according to some embodiments of the invention.

FIG. 7 is a T-distributed Stochastic Neighbor Embedding (t-SNE) graph visualizing a possible distinction between waves received from an individual's mouth, while the probe is positioned at various different positions with respect to the mouth of an individual, according to some embodiments of authentication system and method.

The results were collected in an experiment that was conducted in order to test the way that sampling the mouth of the individual with the probe in different positions affects the analysis of the data.

Sound wave signal samples were taken from a single individual in different positions. The individual was told to insert a probe into their mouth in different positions, as detailed in the legend of the graph of FIG. 7 and avoid movement during sampling.

The probe included a sound wave generator and a sensor that received the reflected waves. The wave generator was 46 Ohms Receiver, Balanced Armature Speaker 20 Hz ~8.8 kHz Top Round 105 dB. The wave sensor was I2S MEMS Microphone, Omnidirectional, −26 dB@94 dB SPL.

A chirp of 3200-9200 Hz Linear Frequency Modulated (LFM) sound waves was transmitted into the mouth of the individual. The chirp included three wave samples, each of which lasted 50 milliseconds with breaks of 50 milliseconds each therebetween. the entire chirp was therefore 250 milliseconds. 20 chirps, hence 60 samples were taken during each of the tested positions.

Figure 6C:
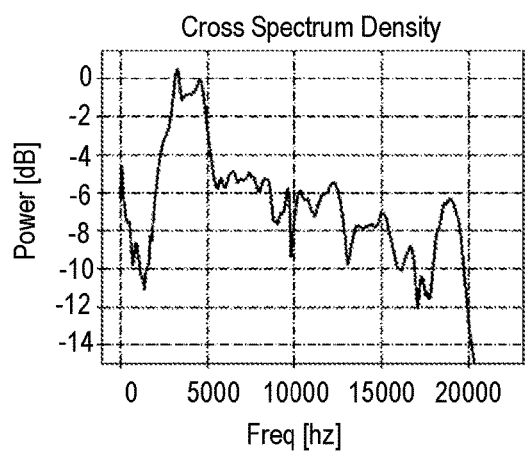
FIG. 6C and FIG. 6D are graphs showing a reference wave used in determining the values of wave samples shown in graph of FIG. 6A, according to some embodiments of an authentication system and method.
Figure 6D:
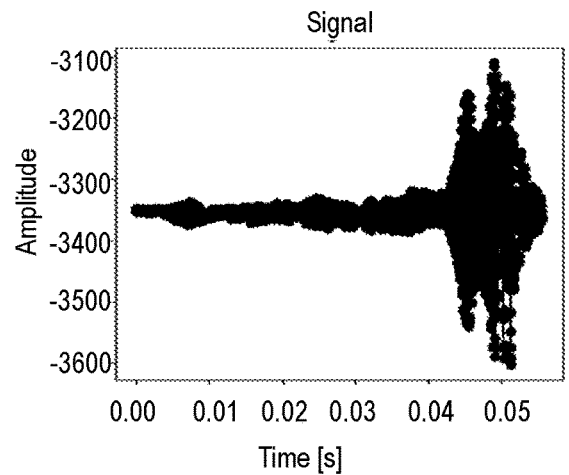

A processor recorded the received wave reflections and encoded the received weaves by Digital Signal Processing (DSP) algorithm and stored in a database. A reference wave represents the ambient sound and was recorded adjacent to sampling the mouth of the individual, in a manner similar to recording the reference chirp as detailed in the description of the experiment of FIGS. 6A, 6C and 6D.

During processing the data, samples were cleaned and normalized with respect to the reference wave. The data was entered to an artificial intelligence (AI) algorithm of the Random Tree kind. The system analyzed the data, compared between the samples and gave each sample a multi-dimensional value that reflects the sample's difference degree with respect to the other samples. The algorithm visualized its analysis using T-distributed Stochastic Neighbor Embedding (t-SNE) on the graph shown in FIG. 7.

Each of the dots shown on the graph of FIG. 7 represent a single sample. after receiving the result, each sample on the graph was given a symbol with respect according to the position of the probe, during which it was taken, in the mouth of the individual. For example, the plus shaped symbols represent wave reflections that were received during positioning the probe in the left side of the individual's mouth, the squared symbols represent wave reflections that were received during positioning the probe in the individual's mouth with no contact at all with the lips, and so forth.

As can be seen in FIG. 7, the AI algorithm arranged the received waves in distinct clusters, each of which comprising samples of the same probe position. The results show that the position of the probe effects the analysis of the sample and way it is classified by the algorithm.

Figure 8A:
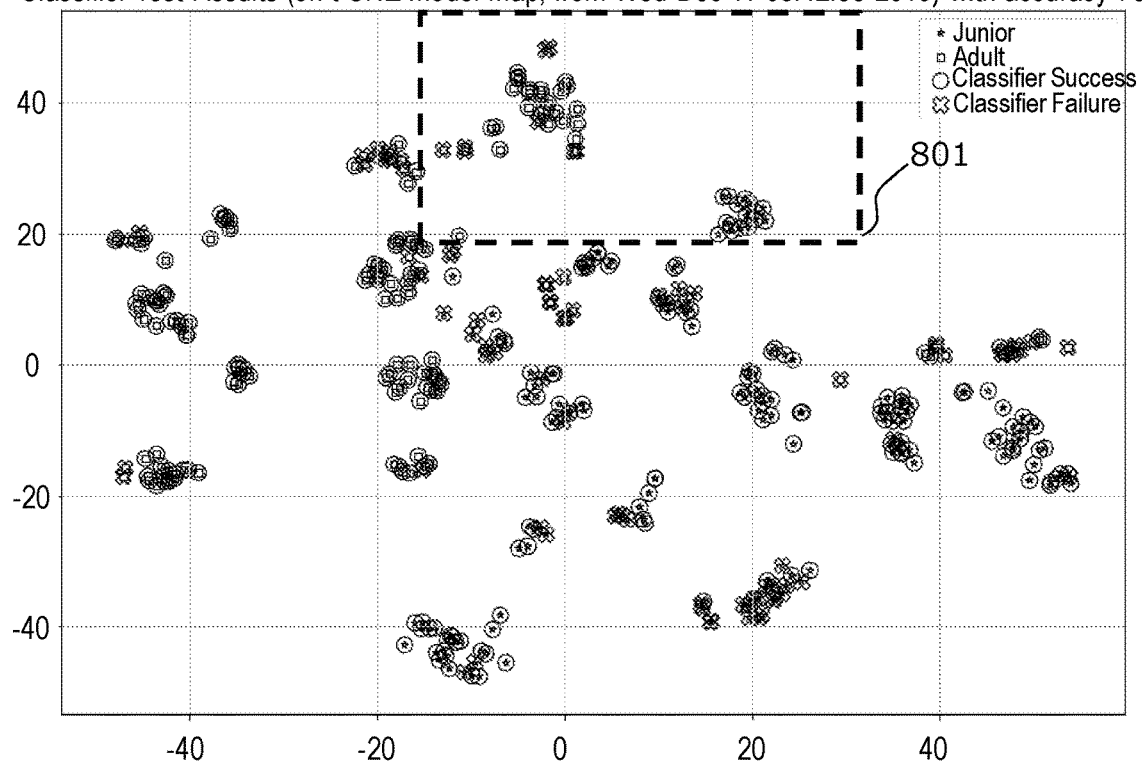
Figure 8B:
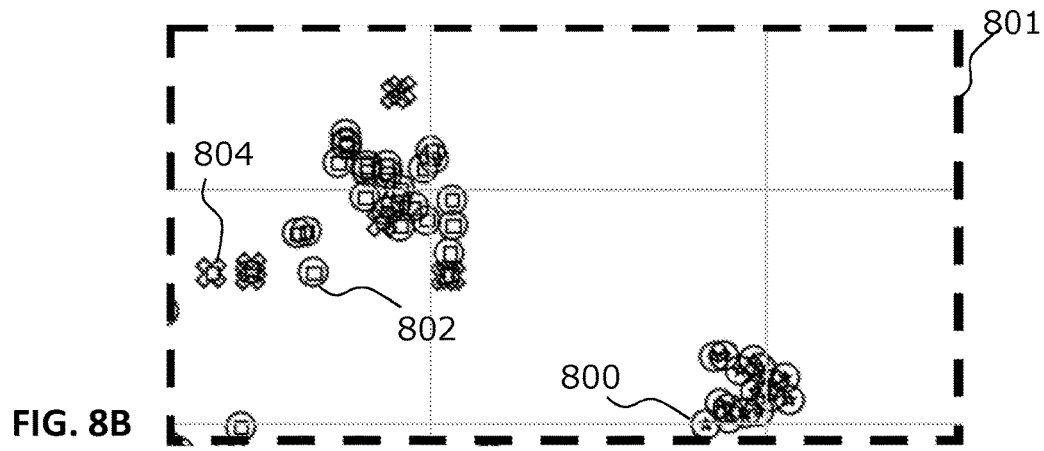

FIGS. 8A and 8B are a T-distributed Stochastic Neighbor Embedding (t-SNE) graph visualizing a possible distinction between adults and children according to received wave reflections, wherein FIG. 8B is an enlarged portion marked by dashed rectangle 801 of FIG. 8A. The results shown were collected in an experiment that was conducted in order to test some embodiments of an authentication system, and its ability to distinguish between adults and children based on reflections of waves transmitted to their mouth.

Sound wave signal samples were taken from 66 subjects, that included 28 adults and 38 children. Adults were defined by ages above 25. Children were defined by ages of below 15. The subjects were told to insert a probe into their mouth and avoid movement during sampling.

The probe included a sound wave generator and a sensor that received the reflected waves. The wave generator was 46 Ohms Receiver, Balanced Armature Speaker 20 Hz ~8.8 kHz Top Round 105 dB. The wave sensor was I2S MEMS Microphone, Omnidirectional, −26 dB@94 dB SPL.

A chirp of 3200-9200 Hz Linear Frequency Modulated (LFM) sound waves was transmitted into the mouth of the individuals. The chirp included three wave samples, each of which lasted 50 milliseconds with breaks of 50 milliseconds each therebetween. the entire chirp was therefore 250 milliseconds. 5 chirps, hence 15 samples were taken from each of the individuals.

A processor recorded the received wave reflections and encoded the received weaves by Digital Signal Processing (DSP) algorithm and stored in a database. A reference wave represents the ambient sound and was recorded adjacent to sampling the mouth of the individual, in a manner similar to recording the reference chirp as detailed in the description of the experiment of FIGS. 6A, 6C and 6D.

During processing the data, samples were cleaned and normalized with respect to the reference wave. As an initial training phase, data relating to 49 of the subjects that were randomly selected was entered to the system. Each of the subject was indicated to the system as an adult/child.

At a next phase, the system analyzed the remaining 17 samples, which were not given an indication. The algorithm was set to determine whether each of the samples belong to an adult or a child. The system analyzed the data, compared between the samples and gave each sample a multi-dimensional value that reflects the sample's difference degree with respect to the other samples. The algorithm visualized its analysis using T-distributed Stochastic Neighbor Embedding (t-SNE) on the graph shown in FIG. 8A.

Each of the marks shown on the graph of FIG. 8A represents a single sample. the algorithm classified each of the samples as an adult or a junior (child). Sample was marked twice. The a star was used to mark reflections taken from a junior (child) and a square for an adult. The performance symbols were marked around the classification symbols. A circle marked for a success, i.e., the algorithm classified a child as a child or an adult as an adult. An X shaped symbol marked for failure, i.e., the algorithm classified a child as an adult or an adult as a child. A portion of FIG. 8A shows the region marked by dashed rectangle a at higher resolution in FIG. 8B. As seen, 800 marks a sample taken from a junior (star) that was correctly identified as such (circled) and 900 marks a sample taken from an adult (square) that was correctly identified as such (circled). A misidentification by the algorithm is depicted at 804, where an adult (square) was not identified as an adult (marked by an X). In the example shown in FIG. 8A, the model was able to distinguish between a child and an adult with an accuracy of 76.3%. When using a learning algorithm, as the number of samples will increase so the accuracy expected to increase. In addition, by changing the cutoff value, it is possible to decrease the number of false positives at the expense of an increase in false negatives, and vice versa.

As described above, in some embodiments, the determination of an adult or child can be provided by a likelihood of accuracy, for example, the determination of the system can be that a subject is a child by a likelihood of 75%, according to the percentage level (%) of wave trends and properties that are recorded in the system as characterizing a child or an adult.

In some embodiments, a machine learning algorithm can be trained to increase accuracy and efficiency of age and/or other identity criteria recognition. Useful examples of age restriction criteria may be helpful in prevention of tobacco, nicotine, cannabis and/or cannabinoid smoking or vaping by children, as well as prevention of minors or children making use of a medical device.

In some embodiments, a group of people can be allowed to use the same device (e.g., a fluid delivery device such as fluid delivery device 10 as described above in FIG. 1A) or a set of devices (e.g., patients' devices in a hospital setting or a few members of the same family). A processor can be configured to allow monitoring of each individual's usage. In some embodiments, the same device, based on input from the device can establish a use regime (e.g., substance administration) associated with each authorized individual. In some embodiments the same device may be configured, based on input from the authentication module, to facilitate administration of the same or different substance(s) to a group of authorized individuals, in parallel or at different times and/or dosages. In some embodiments the same device may be used by a group of people, for example by a few members of a family; in a hospital by a few patients.

Figure 9A:
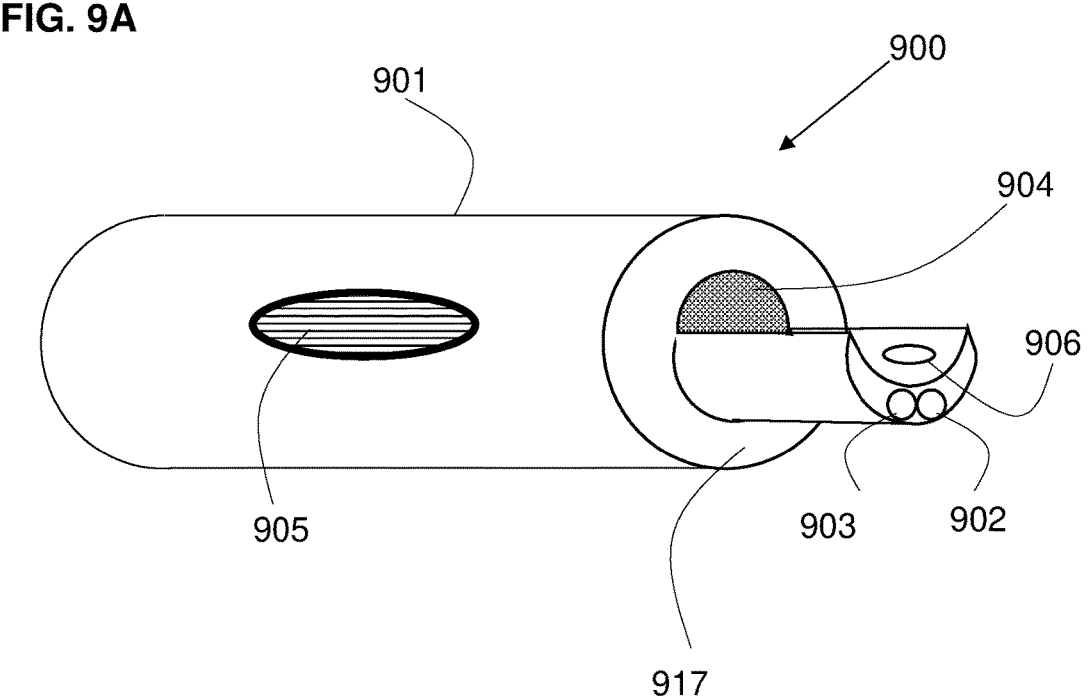
FIG. 9A, FIG. 9B and FIG. 9C are, respectively, schematic diagrams of a fluid delivery device, a mouthpiece, and the fluid delivery device with the mouthpiece positioned on the fluid delivery device for use, according to some embodiments of the invention.
Figure 9B:
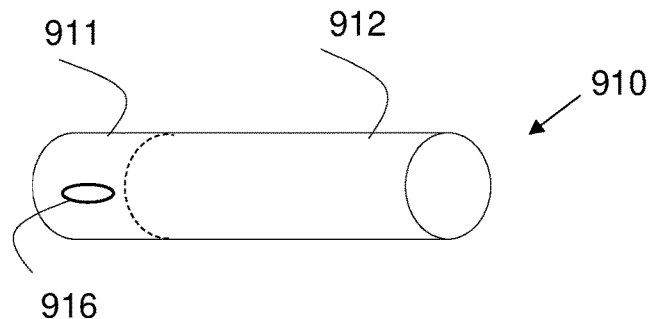
Figure 9C:
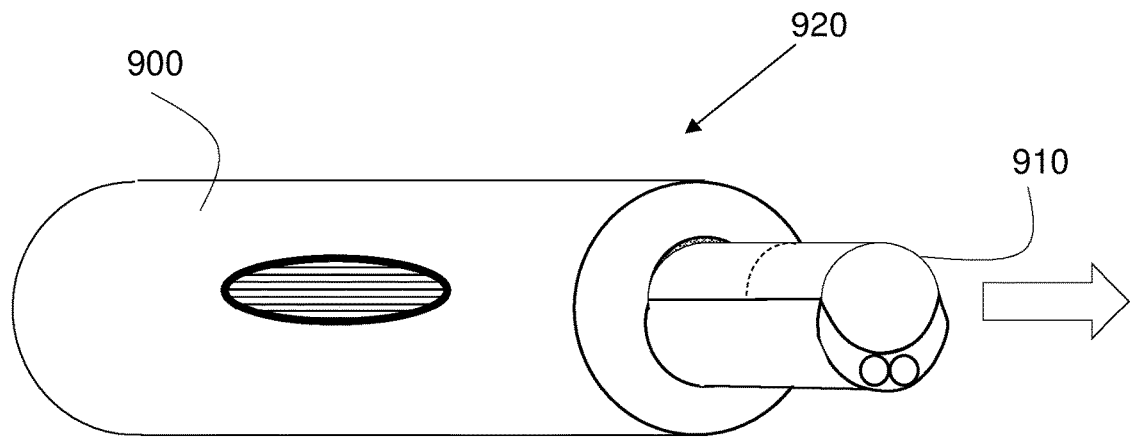

FIG. 9A, FIG. 9B and FIG. 9C are, respectively, schematic diagrams of a fluid delivery device, e-cigarette 900, a mouthpiece 910, and the fluid delivery device with the mouthpiece positioned in the fluid delivery device for use, according to some embodiments of the invention. Optionally, mouthpiece 910 is replaceable.

The e-cigarette 900 includes a housing 901 having a protrusion 917, and is configured to accept a mouthpiece 910. The housing 901 includes an on/off switch 905 and a cavity 904. The protrusion 917 of housing 901 includes a wave generator exit 902, a wave sensor entrance 903 and a sensor 906. Wave generator exit 902, a wave sensor entrance 903, respectively, are connected to a wave generator and a wave sensor in e-cigarette 900 (not shown). In some embodiments, the wave generator and/or wave sensor include wave generator exit 902, a wave sensor entrance 903, respectively. The mouthpiece 910 includes a filter 911, a reservoir 912 and an activator 916.

The e-cigarette 900 can also include one or more processors, wave generators/wave sensors, to allow the e-cigarette to perform the methods as described above (e.g., communicate with the internet, transmit sensor data, process sensor data, make authentication determination, and other method/method steps as described above, for example, in FIGS. 5A through 5D).

During operation the mouthpiece 910 is inserted into cavity 904 and positioned in contact with the protrusion 917 such that the reservoir is at least partially skewered on a heating blade (not shown) positioned within the cavity 904. In some embodiments, when mouthpiece 910 is in position, sensor 906 on protrusion 917 comes into contact with activator 916 on the mouthpiece. This contact can be a prerequisite for operation of e-cigarette 900.

During use the individual can turn e-cigarette 900 on by pressing on/off switch 905 thereby to provide power to the heating blade as well as the wave generator associated with exit 902 and/or wave sensor associated with entrance 903. The individual can position the protrusion 917 along with the filter 911 of mouthpiece 910 in or near their mouth to allow the e-cigarette 900 to proceed to one or more of the registration/authentication/age sorting/access granting essentially as described above. Once access is granted, heating of the reservoir (e.g., tobacco), for example via the blade, can be allowed to pass a threshold temperature and/or substance may be allowed to flow to the individual carried by inhaled air.

FIG. 10A, FIG. 10B, FIG. 10C, FIG. 10D and FIG. 10E are, respectively, schematic diagrams of a fluid delivery device, e-cigarette 1000, a mouthpiece 1100 (optionally a replaceable mouthpiece) and the fluid delivery device with the mouthpiece positioned on the fluid delivery device for use and a longitudinal cross section in the fluid delivery device, according to some embodiments of the invention.

The e-cigarette 1000 includes a housing 1010, and is configured to accept a mouthpiece 1100. The housing 1010 includes an on/off switch 905, a cavity 1040 and a protrusion which includes a wave generator exit 902, a wave sensor entrance 903, a sensor 1060, and a heating blade 1012. Wave generator exit 902, a wave sensor entrance 903, respectively, are connected to a wave generator and a wave sensor in e-cigarette 900 (not shown). In some embodiments, the wave generator and/or wave sensor include wave generator exit 902, a wave sensor entrance 903, respectively. The mouthpiece 1100 includes a filter 1101, a reservoir 1102 and a blade cavity 1103.

The e-cigarette 1000 can also include one or more processors, wave generators/wave sensors, to allow the e-cigarette to perform the methods as described above (e.g., communicate with the internet, transmit sensor data, process sensor data, make authentication determination, and other method/method steps as described above, for example, in FIGS. 5A through 5D).

During operation the mouthpiece 1100 is inserted into cavity 1040 and skewered on the structure that includes heating blade 1012. In some embodiments this causes the sensor 1060, to be positioned within blade cavity 1103 of the mouthpiece 1100 and come into an activator such as activator 916 of FIG. 9B, which is located on an inner wall of mouthpiece 1100 within blade cavity 1103.

During use the individual can turn e-cigarette 1000 on by pressing on/off switch 905 thereby to provide power to the heating blade 1012 as well as the wave generator exit 902 and/or wave sensor entrance 903. The individual can position the mouthpiece 1100 in or near their mouth to allow the e-cigarette 1000 to proceed to one or more of the registration/authentication/age sorting/access essentially as described above. Once access is granted, heating of the reservoir (e.g. tobacco), for example via the blade, can be allowed to pass a threshold temperature and/or substance may be allowed to flow to the individual carried by inhaled air.

Figure 10A:
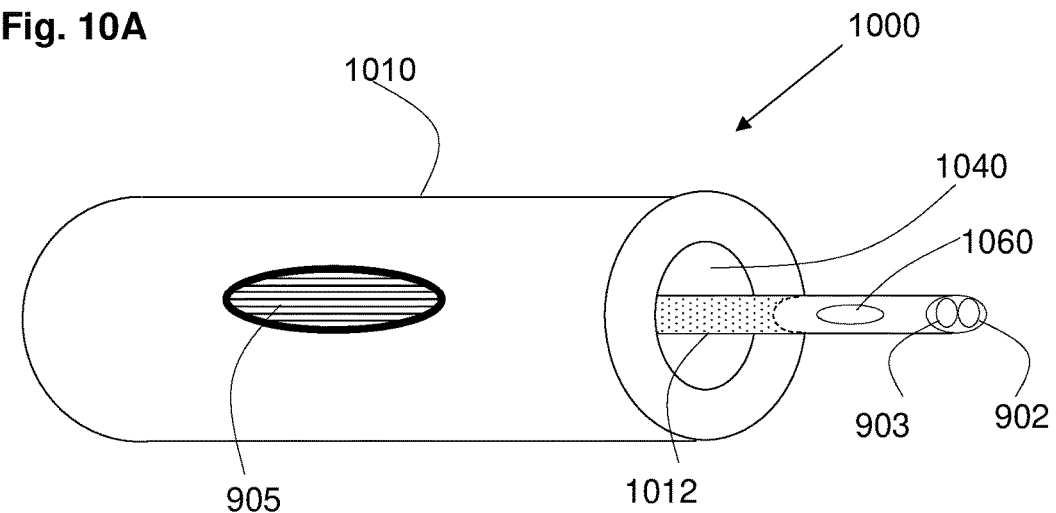
FIG. 10A, FIG. 10B, FIG. 10C, 10D, and FIG. 10E are, respectively, schematic diagrams of a fluid delivery device, a mouthpiece, the fluid delivery device with the mouthpiece positioned on the fluid delivery device for use, and a longitudinal cross section in the fluid delivery device according to some embodiments of the invention.
Figure 10B:
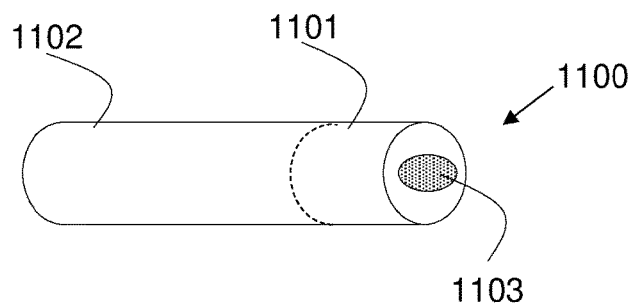
Figure 10C:
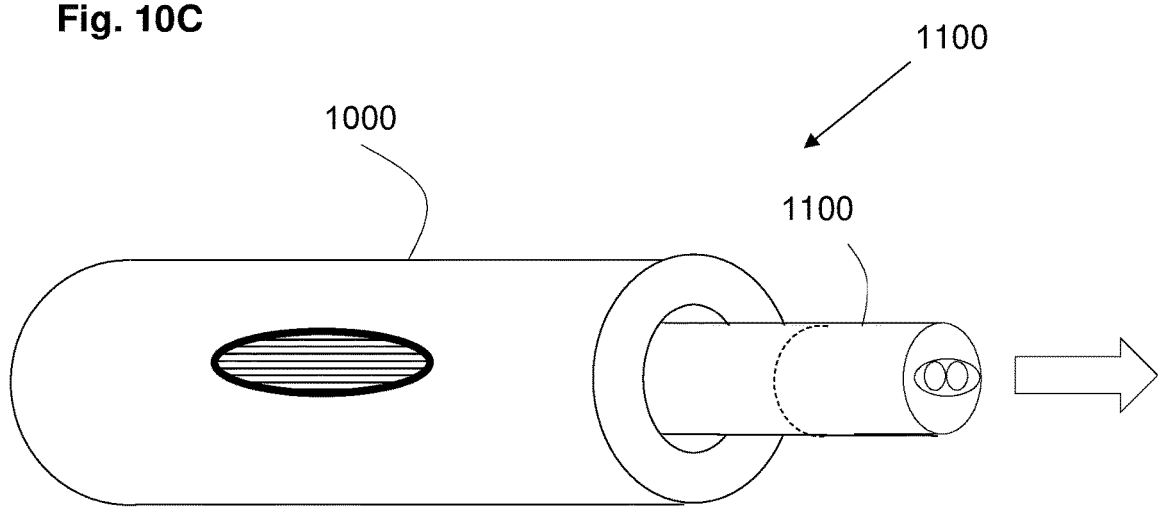
Figure 10D:
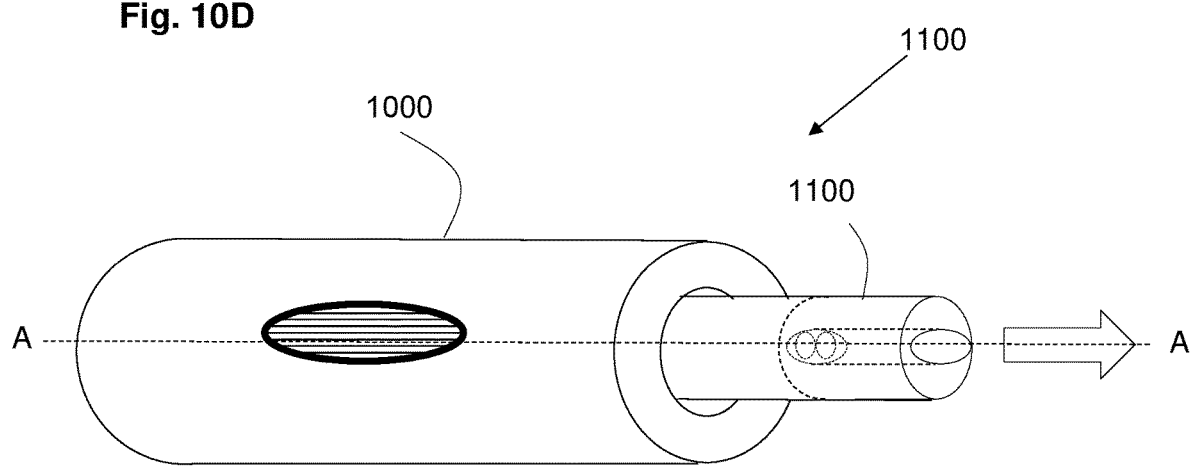

In some embodiments, e-cigarette 1000 and mouthpiece 1100 are or relative proportions such that when mouthpiece 1100 is in cavity 1040 the wave generator exit 902 and wave sensor entrance 903 abut an end of replaceable mouthpiece 1100 as shown in FIG. 10C. In some embodiments, e-cigarette 1000 and mouthpiece 1100 are or relative proportions such that when mouthpiece 1100 is in cavity 1040 the wave generator exit 902 and wave sensor entrance 903 are positioned within the blade cavity 1103 such that they do not abut the end of the e-cigarette 1000 as shown in FIG. 10D. In such embodiments, a portion of the mouthpiece 1100 (e.g. filter 1101) can serve as an enclosure for one or more of wave generator exit 902 and wave sensor entrance 903. In some embodiments (not shown) this portion the mouthpiece 1100 contains one or more media within blade cavity 1103. In some embodiments, blade cavity 1103 includes a dividing member extending along the cavity from the free edge of the filter 1101 to the location of wave generator 902 and wave sensor entrance 903, thereby providing separated enclosures to each of them. Optionally, a groove between wave generator 902 and wave sensor entrance 903 is configured to engage an edge of the dividing member.

Figure 10E:
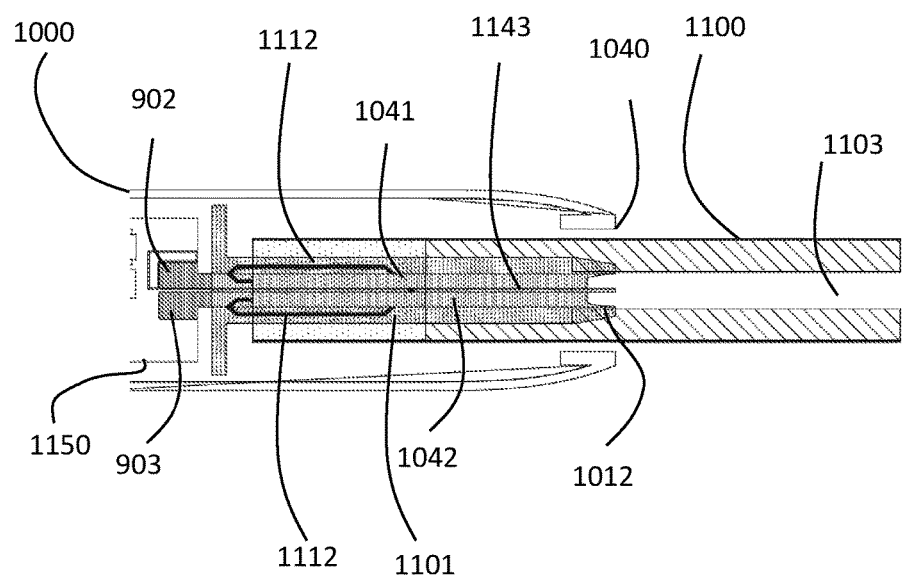

Turning to FIG. 10E, a longitudinal cross-section view along line A-A of an e-cigarette 1000 is shown. Blade 1102 is configured to be inserted into mouthpiece 1100. In carious embodiments, blade 1102 comprises a heat conductive portion 1112 (e.g. comprising an electrically resistive material, for example metal, heated by driving an electric current). As shown, when in use, heat conductive portion 1112 can be inserted into the reservoir 1101 portion of mouthpiece 1100. In some embodiments, blade 1102 comprises a waveguide (e.g. sound guide) 1041 and a receiver waveguide 1042 formed within the blade body. At their first end, waveguides 1041 and 1042 are coupled to a wave generator 902 and a sensor 903 respectively. At their second end waveguides 1041 and 1042 have, respectively, a wave exit and a wave entrance into blade cavity 1103 of mouthpiece 1100. Blade cavity 1103 is optionally a cylindrical element or otherwise provides pathway for wave propagation for transmission into and the mouth of an individual and sensing reflections therefrom, once positioned in their mouth. In the example shown, blade 1102 extends beyond the end of reservoir 1101 reaching partially into blasé cavity 1103. In some embodiments (as depicted for example in FIG. 1-C blade 1102 extends beyond the end of reservoir 1101 reaching essentially the end of mouthpiece 1100. As shown, waveguides 1041 and 1042 are separated by blade partition 1043, which may provide mechanical support and durability, to allow replacement of mouthpiece 1100 without damaging blade 1012 and any part thereof.

In some breath actuated inhalation devices, a period of time typically lapses between the commencement of inhalation and substance delivery. During such period of time the authentication can be performed until vaporization begins. In some embodiments of breath actuated thermal inhalation devices, heating commences at a delay after inhalation begins. Authentication may take place during this delay, such that only if the individual is authenticated, heating is allowed to pass a predefined threshold (e.g. a vaporization temperature of the substance to be delivered). In some embodiments wave transmission and reflection capturing occur at least once between the beginning of inhalation and the beginning of substance delivery, for example, 2 or more times, 5 or more times, 7 or more times or even 10 or more times, etc. In some embodiments, the number of authentication iterations (transmission/reflections cycles) is between 1-7 or even between 1-5.

In some embodiments, wave sensor entrance 903 and/or wave generator exit 902 are incorporated in fluid delivery device 900 or 1000. In some embodiments, wave sensor entrance 903 and/or wave generator exit 902 are incorporated in a mouthpiece 1100 of fluid delivery device 900 or 1000. In some embodiments, the wave sensor 903 and/or wave generator 902 are incorporated in a probe (not shown), operative to be coupled to the fluid delivery device 900 or 1000. In some embodiments the probe includes any of wave sensor 903, wave generator 902, and any of the components of authentication unit, such as described in FIG. 1B, element number 12. In some embodiments, the probe includes or may access registration data of an individual, and operative to serve as an identification object. Optionally, the identification object may be coupled to one or more devices in order to perform authentication and receive access to the fluid delivery device 900 or 1000 and/or to other devices.

Experiment 1:

Thirteen (13) individuals were tested for inhalation device identification. The individuals were told to sit in a comfortable constant position and hold a mouthpiece in their mouth in an inhaling position. Individuals were requested to avoid major changes in facial expression and mouth motions. A sinusoidal sound wave pulse was generated at an amplitude of 0.5 [V] p2p, 0.5 [V] offset, 5 [kHz] frequency and sent to the buzzer for 5 [ms], i.e., 25 cycles. Once the microphone analog output crosses a certain trigger value, the oscilloscope recorded total data window of 20 [ms], 7 [ms] before the trigger value crossing and 13 [ms] thereafter. Each recording is a sample. The data output of the oscilloscope was saved for each sample as a .CSV file format. Each sample consists of approximately 2000 data points. The samples were separated into classes. Each class represents a specific individual. For each class 50 samples were taken.

Figure 11A:
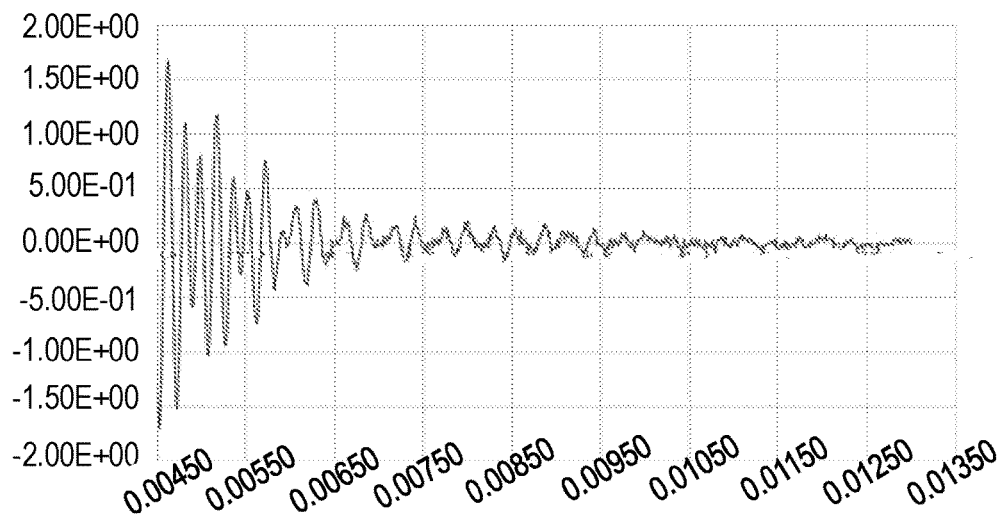
FIGS. 11A and 11B show a diagram visualization of a sample sound wave produced in a subject experiment with (11A) and without (11B) the filtration of the transmitted wave source section.
Figure 11B:
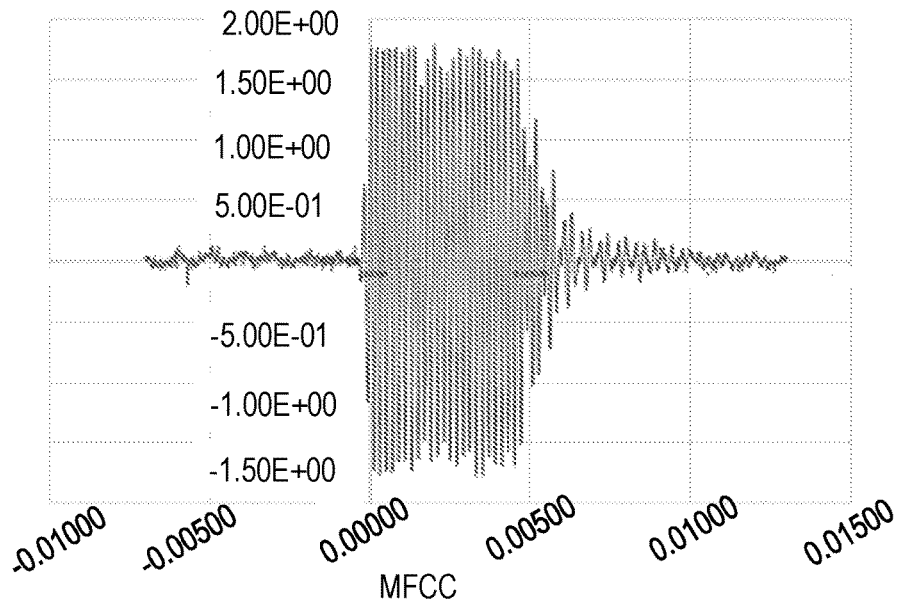
Figure 11C:
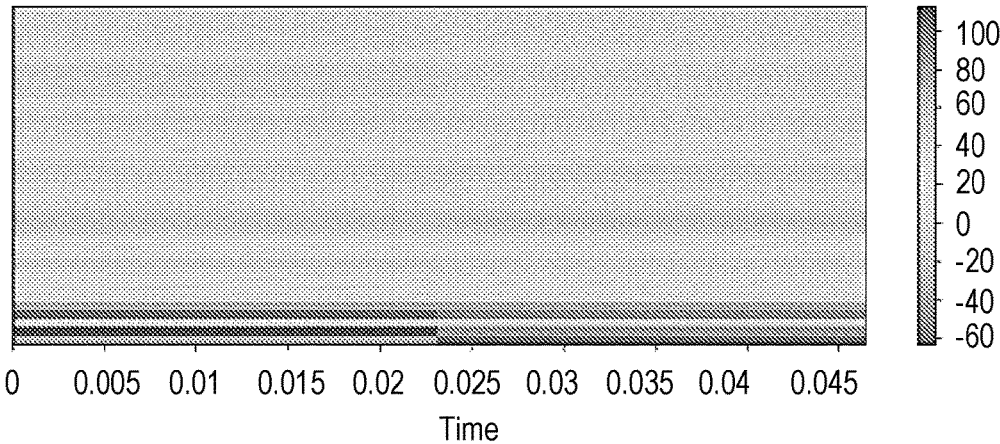
FIG. 11C is a Mel-frequency cepstrum coefficients (MFCC) visualization of a sample sound wave produced in a subject experiment.

The data was prepared, classified and normalized for training and testing in eight different models. Preparation included transformation, cleansing of background noise and visualization of the recorded waves. It was found that better results were achieved by filtering almost all of the transmitted wave source section and comparing only the echo sections, which showed greater variability. To do so, the 7 [ms] before the trigger value, along with 4.5 [ms] out of the 5 [ms] generated wave were cut from the data files. What was left for analysis was almost purely echo phenomena. Some visualizations are shown by way of example in FIGS. 11A-11C. FIGS. 11A and 11B show a diagram visualization of a sample sound wave produced in the subject experiment with (11A) and without (11B) the filtration of the transmitted wave source section. FIG. 11C is a Mel-frequency cepstrum coefficients (MFCC) visualization of a sample sound wave produced in the subject experiment, suitable to some of the testing methods listed below.

The data was divided so a random portion of 75% of the data was defined as training set and a random portion of 25% as a testing set. The data was randomized prior to the division in order to prevent bias.

Testing was performed with the following eight common classification algorithms: Logistic Regression; Support Vector Classification (SVC); K-Neighbors Classifier; Decision Tree Classifier; Extra Tree Classifier; Random Forest Classifier; Extra Trees Classifier; and Multi-layer Perceptron classifier (MLP) Neural Net Classifier.

Training (registration) was applied on each of the eight classifiers, using the training set. During training, the system was entered the true classification of each sample, in order to determine threshold classification rules.

Figure 11D:
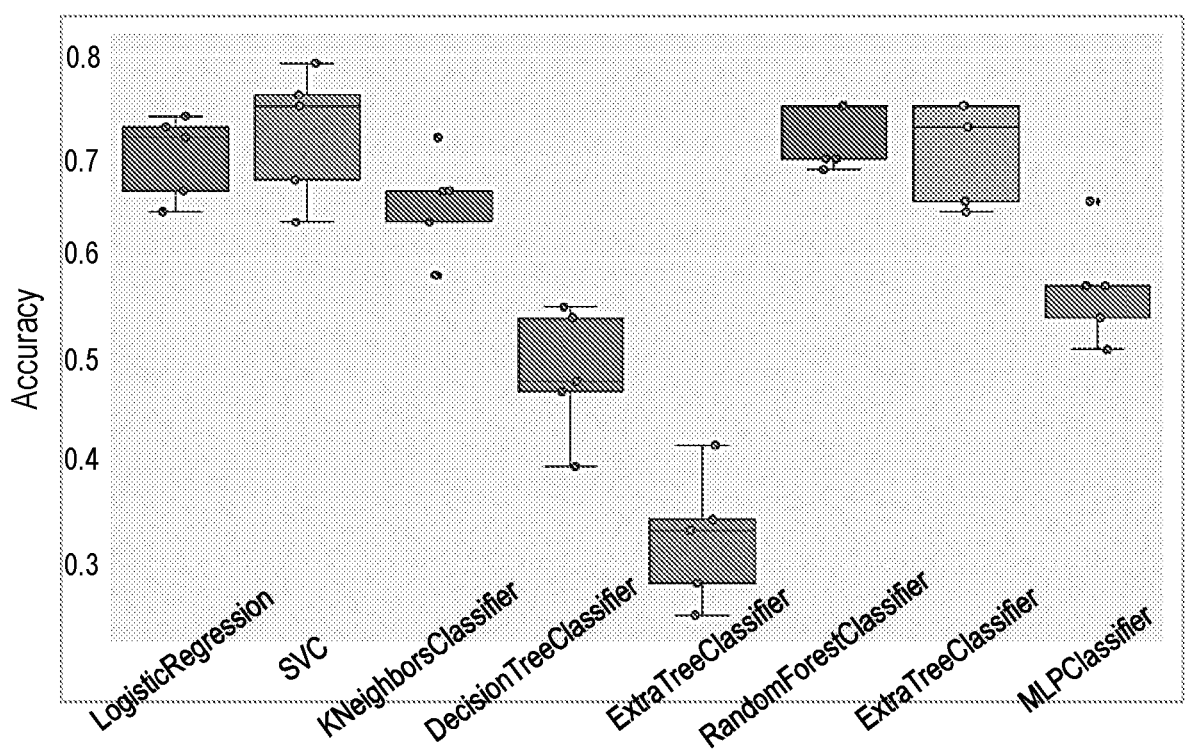
FIG. 11D is a diagram showing an accuracy comparison of the eight classifier algorithms based on sample testing of training module of an authentication module, according to some embodiments.

The testing set was used for measuring the performance for each one of the classifiers. The criteria for success was based on accuracy, precision, recall, and F-1 score of the model. The two highest preforming algorithms were found to be the Extra Trees Classifier and the MLP Neural Net Classifier. An example of accuracy comparison of the eight algorithms based on sample testing is shown in FIG. 11D. The outstanding results that were achieved indicated the following scores:

Mean Precision obtained in the experiment: 0.8276064213564213;

Mean Recall: 0.8333333333333334; and

Mean F1 Score: 0.8268792897275871.

The authentication and/or identification methods and systems described herein (such as shown for example in FIG. 1A) can be used in conjunction with a device that is not necessarily a fluid delivery device.

For example, the identification methods and system can be used with a breathalyzer (e.g., a device that receives exhaled air from an individual and detects the presence of a substance in the exhaled air). Typically, breathalyzers are used to estimate the amount of alcohol in the exhaling individual's blood and thus determine whether or not he is legally drunk or is capable of performing tasks such as driving a motor vehicle. At times, a car cannot be driven (e.g. shift into gear or turn on the ignition) such that it is unlocked only subject to confirmation via a breathalyzer that the exhaling individual is legally sober. In some embodiments of the invention, in order to ensure that a breathalyzer estimates the blood alcohol of the proper individual, the system and methods as described above can be used to register an individual on the breathalyzer. Thereafter, unlocking the car can require wave authentication of the exhaling individual taken together or in close proximity that will not allow transfer of the breathalyzer to a second individual post authorization and prior to exhalation. In some embodiments, movement or repositioning of the breathalyzer by a distance greater than a predefined minimal range from a location or position where an authorization occurred prevents successful unlocking and/or can require a repeated authentication and exhaled air for analysis.

In some embodiments, a device used in conjunction with the authentication and/or identification methods and systems described herein (such as shown for example in FIG. 1A) is an oral thermometer comprising a wave generator and a wave sensor. An individual can be registered on a hospital management system. Thereafter, when a thermometer is used for taking the individual's temperature, the individual's oral signature can be concomitantly taken and authenticated. Optionally, the authentication provides a healthcare professional automatically with conformation of the individual's identity and/or access to the individual's hospital file. Optionally, based on the authentication, the temperature taken and other individual properties are automatically logged in the file.

In some embodiments, a replaceable mouthpiece (e.g., replaceable mouthpiece 450 as described above in FIG. 4) or a protective cover transparent to waves (e.g., an oral thermometer probe cover) is be provided for each individual. In some embodiments the same device is used by a plurality of authorized individuals. In some embodiments a fluid delivery device or system includes a centralized inhalation mechanism, for example designed for use in a hospital (e.g., an ER or in a group of rooms) linked to delivery conduits at each bedside and a centralized device that may be configured to administer different substances (e.g., vaporized) based on personal prescriptions prescribed to each authorized individual.

In some embodiments, the fluid delivery device with an authentication module (e.g., authentication module 12 as described above in FIG. 1B) is configured to allow different individuals to receive different substances, by identifying and/or authenticating an authorized individual from a set of authorized individuals and/or causing the fluid delivery device to operate under a specific operation regime, as prescribed for that individual.

In some embodiments, authentication is performed on each individual of a group of individuals and/or activating the fluid delivery device at a determined pattern for each individual that is authenticated in the group. In some embodiments, the fluid delivery device is configured to authenticate each individual separately (e.g., by binary classification). In some embodiments, when an individual intends to use a fluid delivery device that requires authentication, the individual is required to make a claim regarding their identity and/or the fluid delivery device uses a binary method to confirm the claim before permitting use.

In some embodiments, the fluid delivery device restricts specific total dosage amounts per session and/or day. Such restriction may be based for example on an individual's age, an individual's input, and/or specific prescription to, for example, prevent abuse by the individual that has the prescription (e.g., even if unintentional). In some embodiments, the fluid delivery device restricts specific total dosage amounts per session or day based on individual-defined conditions (e.g., when an authorized individual wants to reduce personal dosage below a personal prescribed dosage). In some embodiments, the fluid delivery device prevents administration of excessive quantity (e.g., overdose) of the substance by restricting specific total dosage for an inhalation or a period of time based on either one or a combination of previous usage, medical data, professional and/or other instruction or recommendation. In some embodiments the device provides a notification to the individual as he nears and/or exceeds a predefined dose. Such notification can be provided, for example, by transmitting a sound within his mouth. Optionally the sound is of such volume that the individual can hear it but others who are not in close proximity or even contact with his head, cannot The volume may be defined in advance and/or in real time according to any of the frequency of the transmitted wave, the properties of the individual and according to the surrounding noise. In some embodiments, a property of the sound may be selected or adjusted by the individual. Optionally, the sound changes as the individual continues to inhale the substance. For example—an increase in one or more of sound periodicity (moving from a single sharp beep to a chain of sharp beeps optionally up to a constant sound), volume (from a sound barely heard by the individual to a sound heard by others), and/or pitch.

In some embodiments, the fluid delivery device sounds within the individual's mouth at one or more times during inhalation. Such sounds can be selected by the individual to be pleasing, as part of his user experience and/or to be annoying so as to facilitate reduced usage (e.g. smoking). The sound can include a short melody or a recorded message. In some embodiments, the sound switches from pleasing to annoying as the delivered dose of a substance nears or exceeds a predefined amount.

Figure 12:
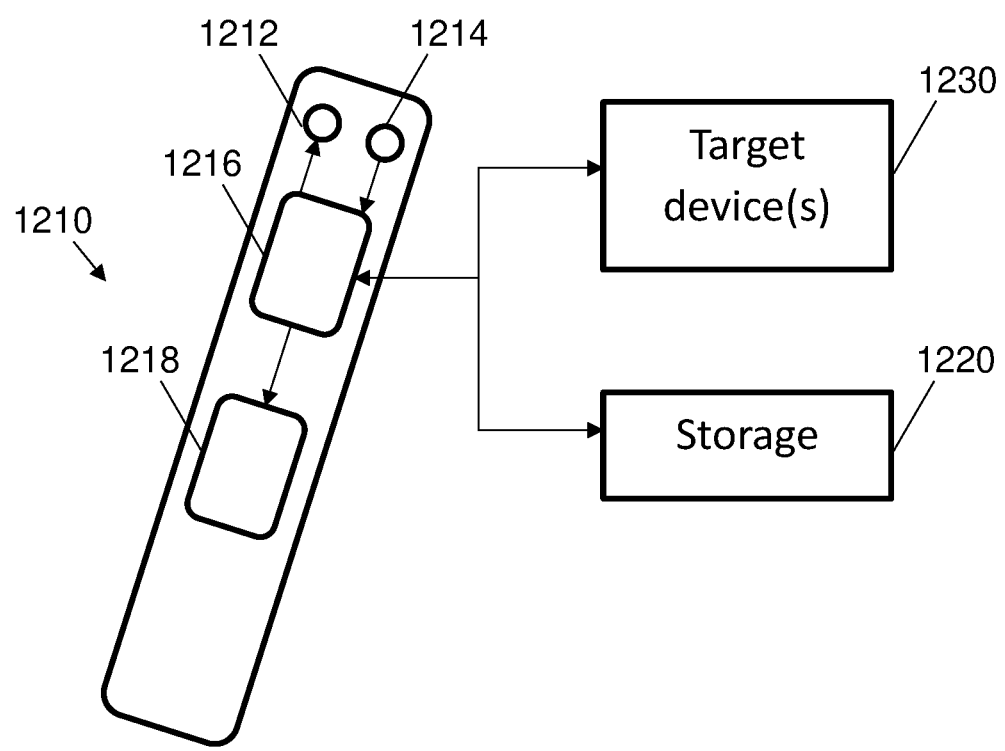
FIG. 12 is a block diagram of a system for obtaining an oral signature of an individual and for storing the oral signature, according to some embodiments of the invention.

FIG. 12 is a block diagram of a system 1200 for obtaining an oral signature of an individual and for using the oral signature for authentication with at least one device, according to some embodiments of the invention.

System 1200 can include a probe 1210. The probe 1210 can include a wave generator 1212 and a wave sensor 1214. Wave generator 1212 may transmit waves towards an individual and wave sensor 1214 may detect at least a portion of reflections of the waves from the individual (e.g., as described above with respect to FIGS. 1A and 1B).

In some embodiments, probe 1210 includes a processor 1216. Processor 1216 may to extract and record from the received at least portion of reflections of the waves an oral signature of the individual, and register the oral signature (e.g., as described above with respect to FIGS. 1A and 1B). The oral signature can be associated with indication(s) of one or more of: personal details of the individual, one or more properties of the individual (e.g., age, allergies, disorders, diseases, etc.), or any authorization indication. In some embodiments, probe 1210 includes a memory 1218. Memory 1218 may store the oral signature. In some embodiments, an oral signature being included in a database is in itself an indication of authorization.

In various embodiments, processor 1216 and/or memory 1218 are part of an external computing device (e.g., a smartphone of the individual). In these embodiments, the external computing device can control probe 1210 to transmit and detect waves.

In various embodiments, processor 1216 and/or memory 1218 are part of probe 1200 (e.g., a smartphone of the individual). In these embodiments, probe 1200 can be or be a part of a dongle, a substance delivery device, a fluid delivery device, an e-cigarette, a vaporizer, an electronic device or any other device configured to perform at least one function based on authentication of an individual via the individual's oral signature.

In various embodiments, system 1200 includes or may be in communication with an external storage device 1220. External storage device 1220 may store the oral signature. External storage device 1220 may, for example, be a remote database, a dongle, etc.

In some embodiments, processor 1216 extracts and records a number of oral signatures or derivations thereof of the same individual, e.g., with different wave patterns, applicable to specific applications, devices, usage regimes, etc. All these oral signatures or derivations thereof may be stored in memory 1218 and/or in external storage device 1220.

Once the individual has been registered with the oral signature or the derivation thereof, the individual can now use the oral signature or the derivation thereof to authenticate individual's identity, authorization and/or property with one or more target devices 1230 and/or uses, in which authentication with the oral signature or the deviation thereof is applicable. For example, the oral signature or the derivation thereof can be used to authenticate individual's identity, authorization and/or property for logging into a bank account, gaining access to places or data, e-cigarettes, inhalers, etc.

Processor 1216 may communicate with target device(s) 1230 by wired and/or wireless communication (e.g., Bluetooth, USB, code scanner, etc.). In some embodiments, processor 1216 controls target device(s) 1230 remotely. For example, probe 1210 can obtain the oral signature of the individual and authenticate the individual via communication with memory 1218 and/or external storage device 1220. In another example, probe 1210 can obtain the oral signature of the individual and transferring data to target device(s) 1230 (e.g., e.g., probe 1210 can provide a new e-cigarette with the individual's oral signature as being of age and the e-cigarette can store this data and later can operate independently of probe 1210). In some embodiments, probe 1210 is used to confirm/update the data from time to time (e.g., the e-cigarette may store the data or use it for a limited duration).

In some embodiments, system 1200 may operate based on reflections of soundwaves produced by the individual. The sound waves produced by the individual may, for example, be soundwaves caused by inhalation causing airflow in the direction of the oral cavity of the individual via at least one of the individual's nose and the fluid delivery device or sounds of inhalation or exhalation or any other non-vocal sounds transmitted in the direction of the individual's mouth, optionally excluding speech and other vocalizations. For example, the reflections may be reflections of soundwaves produced by the individual without making a voice. Examples include the airflow sounds of one or more of inhalation via the mouth, nose and/or via the fluid delivery device and/or exhalation. In some embodiments, probe 1200 includes at least two sensors positioned to detect at least a portion of reflections of the soundwaves from the individual, especially if the generated sound is not predetermined In various embodiments, system 1200 may operate based solely on reflections of soundwaves produced by the individual, based solely on reflection of soundwaves produced by the wave generator 1212 or both.

Figure 13:
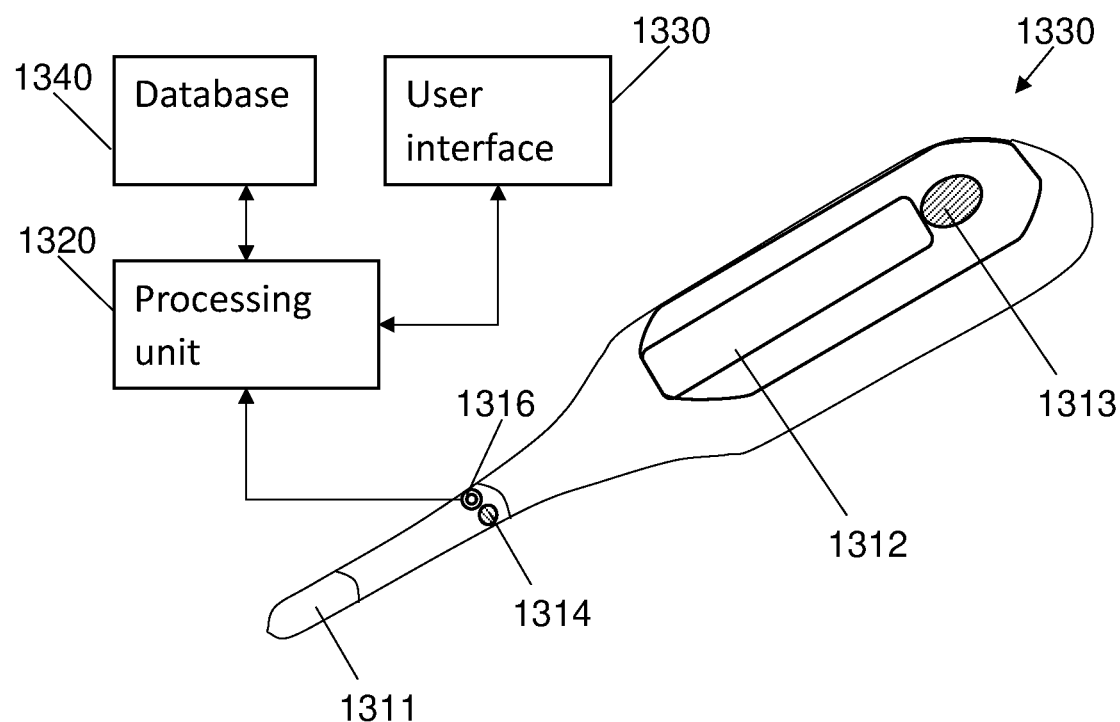
FIG. 13 is a block diagram of a system for obtaining an oral signature of an individual using an oral thermometer, according to some embodiments of the invention.

FIG. 13 is a block diagram of a system 1300 for obtaining an oral signature of an individual using an oral thermometer 1310, according to some embodiments of the invention.

System 1300 may include an oral thermometer 1310. Oral thermometer 1310 may, for example, include a thermal head 1311, a display screen 1312 and an actuator 1313. Oral thermometer may include a wave generator 1314 and a wave sensor 1316. Wave generator 1314 may transmit waves towards an individual and wave sensor 1316 may detect at least a portion of reflections of the waves from the individual (e.g., as described above with respect to FIGS. 1A and 1B). Wave sensor 1316 may be controlled to detect waves while oral thermometer 1310 is within a mouth of the individual. For example, wave sensor 1316 may be controlled to detect waves before, during or after the temperature detection by oral thermometer 1310.

In some embodiments, thermometer 1310 is entered into the individual's mouth, optionally such that at least wave generator 1314 is not covered by an individual's tongue. For example, wave generator 1314 and wave sensor 1316 may be disposed within the individual's mouth behind individual's teeth, exposed to the oral cavity. In some embodiments, oral thermometer 1310 is constructed with dimensions and/or shape to facilitate this position of wave generator 1314 and wave sensor 1316. In some embodiments, wave sensor 1316 is controlled to detect waves while the individual is not responsive and cannot cooperate.

In some embodiments, system 1300 includes a processing unit 1320. Processing unit 1320 may be in communication (e.g., wired and/or wireless) with wave sensor 1316 of oral thermometer 1310.

Processor 1320 may extract an oral signature of an individual based on at least portion of reflections of the waves detected by wave sensor 1316 (e.g., as described above with respect to FIGS. 1A and 1B). Processing unit 1320 may authenticate the individual based on the obtained oral signature (e.g., as described above with respect to FIGS. 1A and 1B).

Upon authentication, processing unit 1320 may direct a user (e.g., the individual or another person, such as a caregiver, healthcare worker, etc.) via a user interface 1330 to a database 1340. Database 1340 may, for example, include individual's personal medical information and/or other information. In some embodiments, processing unit 1320 uses the obtained oral signature to automatically enter the temperature measurement in association with the individual's identity (e.g., in a hospital record).

In some embodiments, other devices are associated with oral thermometer 1310 (e.g., wirelessly or by wired association, e.g., by all being associated with the same hospital site, such as a patient's bed and/or via the authentication with the patient's record). In some embodiments, data relation to the individual and/or operation of any associated device/measurement (e.g., oral the thermometer 1310) is recorded in association with the authenticated identity of the individual.

In various embodiments, a different device or dedicated probe is used instead of oral thermometer 1310. For example, a probe, such as described in FIG. 12 may be used by the user in conjunction with an oral signature to access the individual's data. The individual's body temperature may be measured separately and entered manually to the system by the user.

Figure 14:
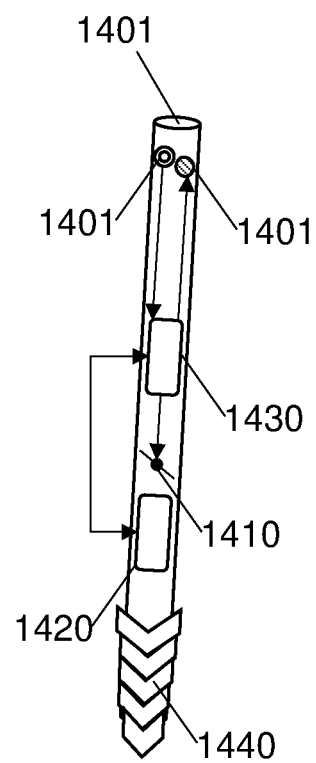
FIG. 14 is a block diagram of a mouthpiece for obtaining an oral signature of an individual in association with liquid consumption, according to some embodiments of the invention.

FIG. 14 is a block diagram of a mouthpiece 1400 for obtaining an oral signature of an individual during a liquid consumption, according to some embodiments of the invention.

In some embodiments, mouthpiece 1400 includes a liquid delivery tract 1401, a wave generator 1402, a wave sensor 1404 and at least one of: a controllable valve 1410, a liquid sensing unit 1420 and a controller 1430. Liquid sensing unit 1420 may include any of a flow rate sensor, a pressure sensor, a substance detector, e.g. pH sensor, and optical sensor, a viscosity sensor and/or any other sensing unit which may provide information about the amount or the type of the liquid flowing in liquid delivery tract 1401.

In various embodiments, a container adapted to contain a liquid includes mouthpiece 1400 or the container be connectable to mouthpiece 1400. In embodiments shown in FIG. 14, mouthpiece 1400 is formed as a straw. In these embodiments, mouthpiece 1400 may include a piercing device 1440, which may be used to couple the mouthpiece to a pierceable container. So that the individual may sip the liquid by suction. In some embodiments, suction is not required. For example, in some embodiments, mouthpiece 1400 is a delivery tract through which liquid may flow by gravitation, while generally no pressure changes are applied (e.g., a neck of a bottle, etc.).

Controller 140 may control wave generator 1402 to transmit waves towards an individual and control wave sensor 1404 to detect at least a portion of reflections of the waves from the individual (e.g., as described above with respect to FIGS. 1A and 1B). Controller 1430 may include a processor. The processor may authenticate the individual based on the at least portion of reflections of the received waves (e.g., as described above with respect to FIGS. 1A and 1B).

In some embodiments, upon authentication of the individual, controller 1430 may control controllable valve 1410 to enable flow of the liquid through delivery tract 1401 of mouthpiece 1400. In some embodiments, controller 1430 may control flow of the liquid through delivery tract 1401 based on outputs of liquid sensing unit 1420. For example, the outputs of liquid sensing unit 1420 may include a type, volume, etc. of the liquid being delivered. In some embodiments, controller 1430 records the user in a database. In various embodiments, controller 1430 may detect an attempt to pour the liquid and/or have an unauthorized individual ingest the liquid and prevent the same by closing controllable valve 1410 and/or issuing an alert (e.g., local and/or to a remote location).

Some embodiments may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that when executed cause a processor to execute method steps in accordance with examples. In some examples the instructions stored on the computer readable medium may be in the form of an installed application and in the form of an installation package. Such instructions may be, for example, loaded by one or more processors and get executed.

For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

Some embodiments are described hereinabove with reference to flow charts and/or block diagrams depicting methods, systems and computer program products according to various embodiments.

Features of various embodiments discussed herein may be used with other embodiments discussed herein. The foregoing description of the embodiments has been presented for the purposes of illustration and description. It is not intended to be exhaustive or limiting to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes that fall within the true spirit.

One skilled in the art will realize the invention can be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

The invention claimed is:

1. A personal device configured for registration and later on authentication of an individual, the device comprising:
    (i) a wave generator for transmitting waves towards the mouth of the individual or a portion thereof;
    (ii) a sensor to detect at least a portion of reflections of the waves transmitted by the wave generator;
    (iii) a memory configured to store at least one oral signature of the individual, and
    (iv) a processor coupled to the sensor and configured to receive waves from the sensor, the processor configured to:
    register an individual by: extracting from the received waves at least one oral signature, recording and storing the at least one oral signature of the individual on said memory, and associating the recorded and stored at least one oral signature with the individual;
    upon an attempted use of the device by a subject, compare at least a portion of the received waves with an oral signature of at least one registered individual; and
    authenticate the subject based on the comparison.

2. The device of claim 1, wherein the device is a substance delivery device comprising:
    a reservoir region for housing a reservoir of the substance; and
    a conduit for delivery of the substance to or through the mouth of the individual.

3. The device of claim 2, comprising an actuator associated with the reservoir, the actuator being configured to control at least one of: release of the substance from the reservoir, and delivery of the substance to the individual based on the authentication of the individual by the processor.

4. The device of claim 2, comprising at least one of:
    a motion detection sensor configured to detect movement of the device and wherein the processor is configured to determine, after a successful authentication, whether the device has moved beyond a predefined minimal range; and
    electric contacts for engaging electric contacts associated with the reservoir and positioned to deliver an electric current to a heating element associated with the reservoir and configured to heat the substance within the reservoir.

5. The device of claim 2, comprising a sensor configured to detect inhalation of the individual via the device; and wherein the processor is configured to authenticate each time an inhalation via the device is performed by the individual.

6. The device of claim 2, wherein the processor is configured to control delivery of the substance to the individual based on the authentication.

7. The device of claim 1, wherein the waves include sound waves.

8. The device of claim 1,
    wherein the oral signature comprises a wave transmission data or a result of analysis thereof indicative of the individual or the individual's property including age, disorders, allergies, diseases.

9. The device of claim 1, wherein the processor is configured to require a security token for registering the individual.

10. The device of claim 1, configured to measure movement of the individual during use of the device.

11. The device of claim 10, wherein the device comprises an inhaler device and wherein the typical movement is measured during inhalation of the individual from the inhaler device; wherein the processor is configured to compare measured movement with typical movement for the authenticated individual, and to prevent or stop use if a predefined range of movement is exceeded.

12. The device of claim 1, wherein the device comprises an inhaler device and wherein the processor is configured to obtain the oral signature by selecting a portion of the received waves which conforms to inhalation dynamics of an inhaling individual.

13. The device of claim 12, wherein the processor is configured to select a portion of the received waves based on commencement of inhalation or once a stable inhalation is detected.

14. The device of claim 1, wherein the oral signature is associated with one or more of: personal details of the individual, usage restriction or permission data, personal properties of the individual.

15. The device of claim 1, wherein the device is operatable in one of the following operation modes:
  registration mode, in which said processor extracts at least one oral signature from said received waves, stores the at least one oral signature and associates the oral signature with an individual;
  authentication mode, in which said processor extracts at least one wave signal sample comprising at least a portion of the received waves, makes a comparison between the at least one wave signal sample and the at least one oral signature and authenticates the subject based on the comparison.

16. The device of claim 15, wherein in said registration mode said wave generator transmits waves to a plurality of locations and/or angles inside the mouth of the individual and wherein said processor extracts said least one oral signature from received waves from said plurality of locations and/or angles.

17. The device of claim 16, wherein in said authentication mode said wave generator transmits waves towards a sample location and/or sample angles inside the mouth of the subject.

18. A method for registering and later on authenticating an individual using a device, the method comprising:
  transmitting waves towards at least a portion of the individual's mouth via at least one of the individual's mouth and nose;
  receiving, using a sensor, reflected waves comprising at least a portion of reflections of the waves from the individual;
  registering the individual by extracting from the received waves at least one oral signature, storing the oral signature on a memory and associating the oral signature with the individual;
  upon an attempted use of the device by a subject, comparing at least a portion of the received waves of the subject with an oral signature of at least one registered individual which is stored on said memory; and
  authenticating the subject based on the comparison.

19. The method of claim 18, wherein the device comprises a substance delivery device and wherein the method comprises delivering a substance to the individual upon successful authentication.

20. The method of claim 19, wherein the device comprises an inhaler device and wherein authenticating and delivering are performed within a single inhalation by the individual from the inhaler device.

21. The method of claim 20, comprising controlling a pressure dependent flow valve such that flow through the valve occurs during inhalation only when a generated pressure exceeds a threshold and wherein transmitting of waves performed partially or only as long as the valve is closed.

22. The method of claim 19, comprising at least one of:
  preventing substance delivery until the authentication is valid;
  permitting substance delivery only after the authentication is valid;
  stopping substance delivery once the authentication is reset; and
  locking the device once authentication is invalid.

23. The method of claim 19, comprising at least one of:
  preventing a heating element used to heat the substance for delivery from heating above a predefined threshold until the authentication is performed;
  permitting the heating element to heat above a predefined threshold only after the authentication is successful;
  reducing or stopping the heating element's heat emission once the authentication indication is reset;
  controlling a flow path of a fluid within the device to the individual such that the fluid reaching the individual will carry the substance only once the authentication indication is successful; and
  upon successful authentication, restricting delivery of the substance to the individual based on a permitted total amount of the substance for a defined period.

24. The method of claim 18, wherein the authenticating comprises determining whether an age of the individual is at least one of above or below one or more age thresholds.

25. The method of claim 18, wherein the authentication is based on biometric data entered to the system including at least one of gender, ethnicity, geographical origin, or any combination thereof.

26. The method of claim 18, comprising normalizing one or more of the detected waves with respect to a predetermined reference wave signal of the sound of the environment.

* * * * *